US012398200B2

(12) United States Patent
Aguzzi et al.

(10) Patent No.: US 12,398,200 B2
(45) Date of Patent: Aug. 26, 2025

(54) ANTI-ALLERGEN ANTIBODIES

(71) Applicants: MABYLON AG, Schlieren (CH); UNIVERSITAET ZUERICH PROREKTORAT MNW, Zurich (CH)

(72) Inventors: Adriano Aguzzi, Zurich (CH); Natascha Wuillemin, Zurich (CH); Tiziana Sonati, Zurich (CH); Dimitri Bieli, Basel (CH)

(73) Assignees: MABYLON AG, Schlieren (CH); UNIVERSITAET ZUERICH PROREKTORAT MNW, Zurich (CH)

( * ) Notice: Subject to any disclaimer, the term of this patent is extended or adjusted under 35 U.S.C. 154(b) by 255 days.

(21) Appl. No.: 17/714,507

(22) Filed: Apr. 6, 2022

(65) Prior Publication Data
US 2022/0372117 A1    Nov. 24, 2022

Related U.S. Application Data

(63) Continuation of application No. 16/625,085, filed as application No. PCT/EP2018/066430 on Jun. 20, 2018, now abandoned.

(30) Foreign Application Priority Data

Jun. 23, 2017 (GB) ...................................... 1710059
Mar. 9, 2018 (EP) ..................................... 18160974

(51) Int. Cl.
    *C07K 16/16* (2006.01)
    *A61K 39/395* (2006.01)
    *A61P 37/08* (2006.01)

(52) U.S. Cl.
    CPC ............ *C07K 16/16* (2013.01); *A61K 39/395* (2013.01); *A61P 37/08* (2018.01); *C07K 2317/21* (2013.01); *C07K 2317/34* (2013.01)

(58) Field of Classification Search
    None
    See application file for complete search history.

(56) References Cited

U.S. PATENT DOCUMENTS

| 6,372,716 B1 | 4/2002 | Bush et al. |
| 6,566,329 B1 | 5/2003 | Meyn et al. |
| 6,685,940 B2 | 2/2004 | Andya et al. |
| 2003/0202980 A1 | 10/2003 | Caplan et al. |
| 2020/0199207 A1 | 6/2020 | Aguzzi et al. |
| 2020/0255503 A1 | 8/2020 | Orengo |

FOREIGN PATENT DOCUMENTS

| EP | 0239400 A2 | 9/1987 |
| EP | 0619323 A1 | 10/1994 |
| EP | 1403280 A1 | 3/2004 |
| EP | 1440979 A1 | 7/2004 |
| EP | 2295076 A1 | 3/2011 |
| WO | WO-8809344 A1 | 12/1988 |
| WO | WO-8909622 A1 | 10/1989 |
| WO | WO-9007861 A1 | 7/1990 |
| WO | WO-9404686 A1 | 3/1994 |
| WO | WO-9724139 A1 | 7/1997 |
| WO | WO-0030680 A1 | 6/2000 |
| WO | WO-0136621 A2 | 5/2001 |
| WO | WO-0139799 A2 | 6/2001 |
| WO | WO-2007134350 A2 | 11/2007 |
| WO | WO-2008127105 A1 | 10/2008 |
| WO | WO-2008156704 A2 | 12/2008 |
| WO | WO-2018234383 A1 | 12/2018 |

OTHER PUBLICATIONS

Javaloyes, G., et al., "Performance of Different in Vitro Techniques in the Molecular Diagnosis of Peanut Allergy," J. Invest. Allergol. Clin. Immunol. 22(7):508-513, Esmon Publicidad S.A., Spain (2012).
Al-Lazikani, B., et al., "Standard conformations for the canonical structures of immunoglobulins," J. Mol. Biol. 273(4):927-948, Elsevier, Netherlands (1997).
Bublin, M., et al. "Cross-Reactivity of Peanut Allergens," Curr. Allergy Asthma Rep. 14(426), 12 pages, Springer, Germany (2014).
Codreanu, F., et al., "A novel immunoassay using recombinant allergens simplifies peanut allergy diagnosis," Int. Arch. Allergy Immunol. 154(3), 216-226, S. Karger AG, Switzerland (2010).
Eberlein, B., et al., "Basophil activation testing in diagnosis and monitoring of allergic disease—an overview," Allergo Journal International 25(4): 18 pages, Springer, Germany (2016).
Ebo, D.G., et al., "Basophil Activation Test by Flow Cytometry: Present and Future Applications in Allergology," Cytometry Part B: Clinical Cytometry 74B: 201-210, Clinical Cytometry Society, United States (2008).
Gernez, Y., et al., "Basophil CD203c Levels Are Increased at Baseline and Can Be Used to Monitor Omalizumab Treatment in Subjects with Nut Allergy," Int. Arch. Allergy Immunol. 154:318-327, S. Karger AG, Switzerland (2011).
Hausmann, O.V., et al., "Robust expression of CCR3 as a single basophil selection marker in flow cytometry," Allergy 66(1): 85-91, John Wiley and Sons A/S, United States (2011).
Hoh, R.A., et al., "Single B Cell Deconvolution of Peanut-specific Antibody Responses in Allergic Patients," Journal of Allergy and Clinical Immunology 137(1): 157-167, Elsevier, Netherlands (2016).
Huang, J., et al., "Isolation of human monoclonal antibodies from peripheral blood B cells," Nature Protocols 8:1907-1915, Nature Publications, London, United Kingdom (2013).

(Continued)

*Primary Examiner* — Nora M Rooney
(74) *Attorney, Agent, or Firm* — STERNE, KESSLER, GOLDSTEIN & FOX P.L.L.C.

(57) ABSTRACT

The present invention generally relates to antibodies or binding fragments thereof capable of binding an allergen, in particular a food allergen as well as pharmaceutical compositions comprising such antibodies or binding fragments thereof for the treatment of allergy, in particular food allergy. In addition the invention relates to methods for evaluating the capacity of a candidate antibody or binding fragment thereof to inhibit allergen binding/and/or allergen-induced activity in a human and methods of detecting or quantifying whether an allergen is present in a sample.

13 Claims, 6 Drawing Sheets

Figure 1:
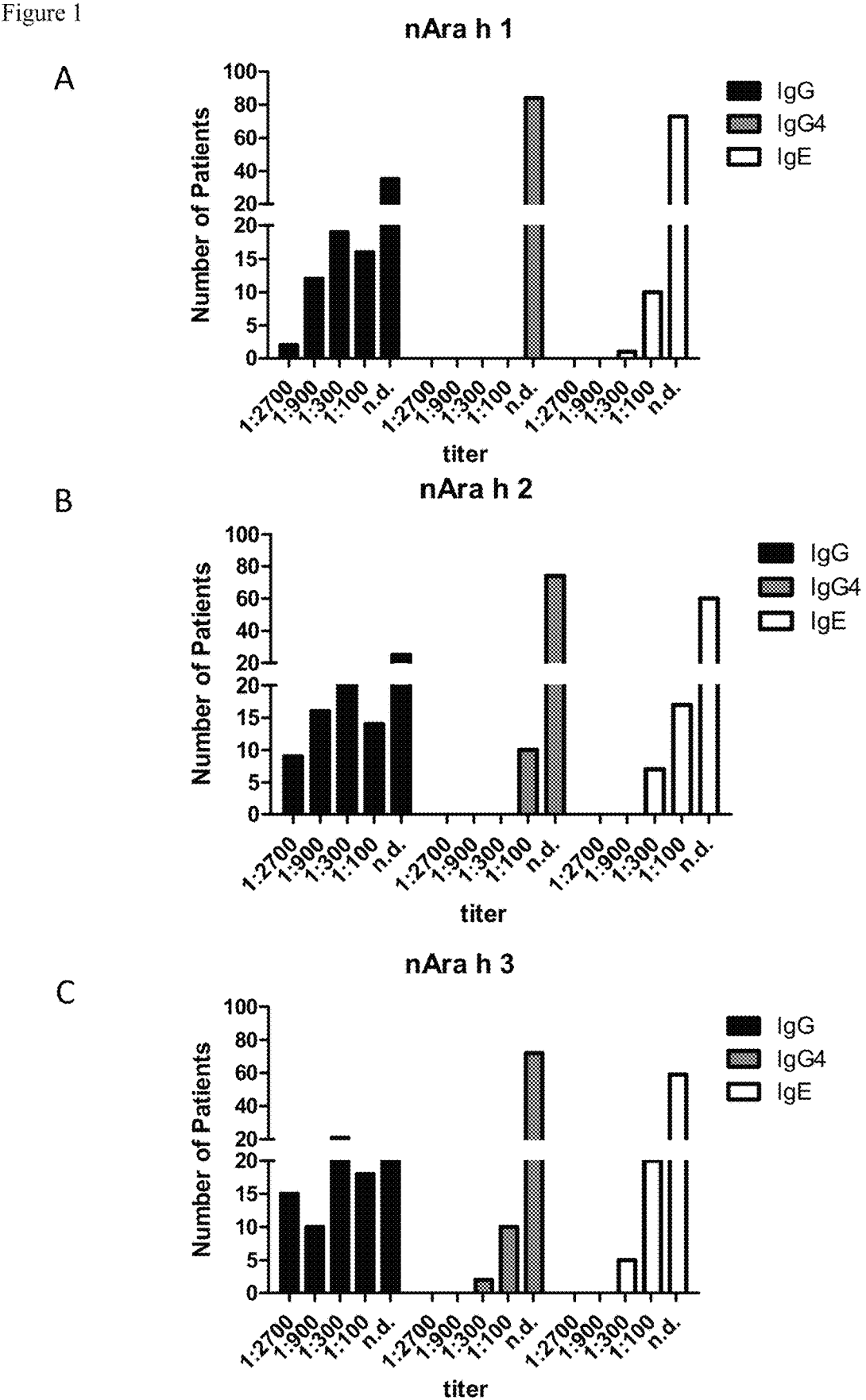

Specification includes a Sequence Listing.

(56) References Cited

OTHER PUBLICATIONS

International Search Report and Written Opinion for International Application No. PCT/EP2018/066430, European Patent Office, Netherlands, mailed on Nov. 29, 2018, 19 pages.

MacGlashan, D.W., "Basophil activation testing," Journal of Allergy and Clinical Immunology 132(4): 777-787, American Academy of Allergy, Asthma & Immunology, United States (2013).

Malmborg, A., "BIAcore as a tool in antibody engineering," J. Immunol. Methods 183(1): 7-13, Elsevier, Netherlands (1995).

Martin, A., et al., "Modeling antibody hypervariable looks: A combined algorithm," Proc. Natl. Acad. Sci. USA 86:9268-9272, United States National Academy of Sciences, United States (1989).

Santos, A.F. and Lack, G., "Basophil activation test: food challenge in a test tube or specialist research tool?" Clinical and Translational Allergy 6(10), 9 pages, BioMed Central Ltd., United Kingdom (2016).

Shreffler, W. G., et al. "Microarray immunoassay: Association of clinical history, in vitro IgE function, and heterogeneity of allergenic peanut epitopes," J. Allergy Clin. Immunol. 113, 776-782, American Academy of Allergy, Asthma and Immunology, United States (2004).

Schier, R. and Marks, J.D., "Efficient in vitro affinity maturation of phage antibodies using BIAcore guided selections," Human Antibodies Hybridomas 7(3): 97-105, Butterworth-Heinemann, United States (1996).

Thompson, J.D., et al., "Clustal W: improving the sensitivity of progressive multiple sequence alignment through sequence weighting, position-specific gap penalties and weight matrix choice," Nucl. Acids Res. 22(22): 4673-4680, Oxford University, United Kingdom (1994).

Uermösi, C., et al., "Mechanism of allergen-specific desensitization," J. Allergy Clin. Immunol. 126: 375-383, American Academy of Allergy, Asthma & Immunology, United States (2010).

Vazquez-Lombardi, R., et al., "Challenges and opportunities for non-antibody scaffold drugs," Drug Discovery Today 20(10): 1271-1283, Elsevier, Netherlands (2015).

"Vector NTI Advance™ 10 User's Manual," pp. 389-662, Invitrogen Corporation, United States (2004).

Wardemann, H., et al., "Predominant Autoantibody Production by early Human B Cell Precursors," Science 301:1374-1377, American Association for the Advancement of Science, United States (2003).

Mariuzza, R.A., et al., "The structural basis of antigen-antibody recognition," Annu. Rev. Biophys. Biophys. Chem. 16:139-159, Annual Reviews, United States (1987).

MacCallum, R.M., et al., "Antibody-antigen Interactions: Contact Analysis and Binding Site Topography," J. Mol. Biol. 262:732-745, Elsevier, Netherlands (1996).

De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," J. Immunol. 169:3076-3084, American Association of Immunologists, United States (2002).

Goel, M., et al., "Plasticity within the Antigen-Combining Site May Manifest as Molecular Mimicry in the Humoral Immune Response," J. Immunol. 173(12):7358-7367, American Association of Immunologists, United States (2004).

Kahn, T., et al., "Adjustable locks and flexible keys: plasticity of epitope-paratope interactions in germline antibodies," J. Immunol. 192(11):5398-5405, American Association of Immunologists, United States (2014).

Poosarla, V.G., et al., "Computational de novo design of antibodies binding to a peptide with high affinity," Biotech. Bioeng. 114(6):1331-1342, Wiley, United States (Jun. 2017).

Flicker, S., et al., "Passive immunization with allergen-specific IgG antibodies for treatment and prevention of allergy," Immunobiol. 218(6):884-891, Elsevier, Netherlands (2012).

Dodev, T.S., et al., "Inhibition of allergen-dependent IgE activity by antibodies of the same specificity but different class," Allergy 70(6):720-724, Wiley, United States (2015).

Office Action mailed Oct. 6, 2021 in U.S. Appl. No. 16/625,085, Aguzzi, A., et al., 371(c) Date: Dec. 20, 2019, 18 pages.

Ball, T., et al., "Reducing allergenicity by altering allergen fold: a mosaic protein of Phl p 1 for allergy vaccination," Allergy 64(4):569-580, Wiley, United States (Apr. 2009).

Chen, K.-W., et al., "Carrier-bound nonallergenic Der p 2 peptides induce IgG antibodies blocking allergen-induced basophil activation in allergic patients," Allergy 67(5):609-621, Wiley, United States (May 2012).

Gadermaier, E., et al., "Possible therapeutic potential of a recombinant group 2 grass pollen allergen-specific antibody fragment," Allergy 69(2):261-264, Wiley, United States (Feb. 2014).

Flicker, S., et al., "Conversion of grass pollen allergen-specific human IgE into a protective $IgG_1$ antibody," European Journal of Immunology 32(8):2156-2162, Wiley-VCH Verlag GmbH, Germany (Aug. 2002).

Lebecque, S., et al., "Immunologic characterization of monoclonal antibodies that modulate human IgE binding to the major birch pollen allergen Bet v 1," The Journal of Allergy and Clinical Immunology 99(3):374-384, Elsevier, Netherlands (Mar. 1997).

Stanley, J.S., et al., "Identification and Mutational Analysis of the Immunodominant IgE Binding Epitopes of the Major Peanut Allergen Ara h 2," Archives of Biochemistry and Biophysics 342(2):244-253, Elsevier, Netherlands (Jun. 1997).

Van Ree, R., and Aalberse, R.C., "Rabbit IgG Directed to a Synthetic C-Terminal Peptide of the Major Grass Pollen Allergen Lol p I Inhibits Human Basophil Histamine Release Induced by Natural Lol p I," International Archives of Allergy and Immunology 106(3):250-257, Karger Publishers, Switzerland (Mar. 1995).

Stone, K., et al., "IgE, Mast Cells, Basophils, and Eosinophils," The Journal of Allergy and Clinical Immunology 125(2 Suppl 2): S73-S80, Elsevier, Netherlands (Feb. 2010).

Mora, J., et al., "Expression of the High Affinity IgE Receptor by Neutrophils of Individuals with Allergic Asthma is Both Minimal and Insensitive to Regulation by Serum IgE," Clinical Immunology 132(1): 132-140, Elsevier, Netherlands (Jul. 2009).

ANTI-ALLERGEN ANTIBODIES

CROSS REFERENCE TO RELATED APPLICATIONS

This application is a continuation of U.S. application Ser. No. 16/625,085, § 371(c) Date: Dec. 20, 2019, which is a national phase entry of International Application No. PCT/EP2018/066430, filed Jun. 20, 2018, which claims the priority benefit of EP Application No. 18160974.4, filed Mar. 9, 2018, and GB Application No. 1710059.5, filed Jun. 23, 2017, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 4532_0010003_Seqlisting_ST25.txt; Size: 59,623 bytes; and Date of Creation: Mar. 31, 2022) is herein incorporated by reference in its entirety.

FIELD OF THE INVENTION

The present invention generally relates to antibodies or binding fragments thereof capable of binding an allergen, in particular a food allergen as well as pharmaceutical compositions comprising such antibodies or binding fragments thereof for the treatment of allergy, in particular food allergy. In addition the invention relates to methods for evaluating the capacity of a candidate antibody or binding fragment thereof to inhibit allergen binding/and/or allergen-induced activity in a human and methods of detecting or quantifying whether an allergen is present in a sample.

BACKGROUND OF THE INVENTION

Food allergies are reactions to ingested foods that may lead to clinical manifestations from skin, respiratory and gastrointestinal symptoms up to severe and life-threatening reactions, i.e. systemic anaphylaxis. Allergic reactions to many different types of foods have been described, but some of the most common are reactions to peanuts and shellfish. Such immediate hypersensitivity reactions are caused by immune responses to environmental antigens, also called allergens. Allergen encounter results in the production of immunoglobulin E (IgE) antibodies by antibody-producing cells of the blood, the so-called B cells. IgE antibodies specific for the allergens bind to FcεRI receptors on mast cells and basophils, and upon critical food intake the allergens are binding to pre-bound IgE on the surface of mast cells and basophils. When these cell-associated IgE antibodies are cross-linked by the allergen, mast cells and basophils are activated to rapidly release a variety of mediators (e.g. histamine, leukotriene, lipid mediators), thereby triggering symptoms of allergy.

Systemic anaphylaxis, as manifested by urticaria, angioedema, bronchospasm, diarrhea, dysrhythmias, and cardiovascular collapse, is responsible for a large number of emergency visits, hospital admissions, and deaths each year. Food allergy is responsible for 20-30% of the emergency visits for anaphylaxis and 100-200 deaths annually in the United States and 50-60% of these are caused by peanut allergy.

Indeed, allergy to peanuts is the most frequent cause of food-related death. Compared to other food allergies, peanut allergy is less likely to be outgrown. Individuals may be so sensitive to peanut allergens that severe systemic reactions can occur in response to minute contaminants of the allergen introduced accidentally during food preparation. Accidental ingestions of peanuts may result in severe and fatal reactions and occur in up to 25-75% of patients over a 5-year period, causing significant anxiety in patients and in families of children with peanut allergy.

Ara h 2 was described as the most important peanut allergen, as it was identified as a predictor of clinical reactivity to peanut. Polysensitization to Ara h 2 and Ara h 1 and/or Ara h 3 appeared to be predictive of more severe reactions (Bublin, M. et al. Cross-reactivity of peanut allergens. Curr. Allergy Asthma Rep. 14, 426 (2014)). In addition, Ara h 6 has recently emerged as a major peanut allergen (Codreanu F, et al. A novel immunoassay using recombinant allergens simplifies peanut allergy diagnosis. Int. Arch. Allergy Immunol. 154, 216-226 (2011)). Ara h 1 (cupin) contributes to 12-16% of the total protein content of a peanut; Ara h 2 (2S albumin) to 5.9-9.3%. Together, Ara h 1, 2 and 3 account for 75% of total protein content. All known peanut allergen classes comprise 85% of the total peanut protein content (Bublin et al.). Mono-sensitization to a single peanut allergen is very rare, but sensitization occurs with a high degree of heterogeneity to a number of peanut allergens (Shreffler, W. G., et al. Microarray immunoassay: Association of clinical history, in vitro IgE function, and heterogeneity of allergenic peanut epitopes. J. Allergy Clin. Immunol. 113, 776-782 (2004)).

Allergen immunotherapy, also known as desensitization, involves exposing the patient to increasing amounts of allergen and is commonly used to treat patients allergic to many seasonal and perennial allergens. In contrast, in peanut allergic patients allergen immunotherapy has not been established, primarily due to the safety risk of treating patients with highly allergenic peanut proteins. In contrast to symptomatic medication such as epinephrine, antihistamines, β-adrenergic agonist and corticosteroid, effective allergen immunotherapy causes an increased immunological tolerance to the allergen or leads to a protective immunity against allergens.

OBJECTIVES AND SUMMARY OF THE INVENTION

In order to meet the above needs, it is one objective of the invention to provide antibodies or binding fragments thereof for the effective treatment of allergies, in particular food allergies, such as peanut allergy.

The antibodies or binding fragments thereof described herein may be capable of reducing, inhibiting or neutralizing allergen-mediated biological activity. In particular, the antibodies may be capable of reducing or inhibiting the binding of an IgE antibody to the food allergen. Thus, the antibodies or binding fragments thereof according to the invention decrease or inhibit the activation of the mast cells or basophils and therefore decrease or prevent the release of mediators (e.g. histamine, lipid mediators, leukotriene). Thereby, the antibodies described herein may inhibit allergy symptoms that would usually occur in the patient after contact with the allergen (e.g. contact with the eyes, nose or mouth or food uptake).

The inventors found that treatment of patients suffering from peanut allergy with human-derived antibodies could be highly effective. Since human-derived antibodies underwent the natural "evolution" in the human body, these antibodies are highly effective for the treatment of a patient.

The food allergen may be a peanut allergen. In an specific embodiment the peanut allergen is selected from the group consisting of Ara h 1, Ara h 2, Ara h 3, Ara h 4, Ara h 5, Ara h 6/7, Ara h 8, Ara h 9 and Ara h 10/11. Preferably, the allergen is selected from the group consisting of Ara h 1, Ara h 2, Ara h 3 and Ara h 6, or a combination thereof. Typically, the peanut allergen is of peanut origin, recombinantly expressed or is a synthetic peanut peptide.

Typically, the antibody may be a monoclonal antibody. In some embodiments, the antibody may be a recombinant antibody.

The antibody may be an IgG or IgA antibody. IgG and IgA compete with IgE for binding sites on the allergen and thereby prevent recognition of allergens by IgE bound to Fcε receptors on the surface of mast cells and basophils. This may include direct competition by binding to the same epitope or competition through steric hindrance. Furthermore, IgG antibodies bound to the allergen can lead to cross-linking of Fcε and inhibitory FcγRIIB receptors, resulting in the decrease of effector cell activity. Thereby the IgG and IgA antibodies or binding fragments thereof according to the invention can be used for the effective prevention or treatment of allergies.

In some embodiments, the variable regions, portions thereof or the CDRs are human-derived. For example, the variable regions, portions thereof or the CDRs are derived from an IgE antibody and grafted in a scaffold of an IgG or IgA antibody. In one embodiment, the peptide sequence of the antibody or binding fragment thereof is identical or at least 60% identical to the sequence of the antibody extracted from the human. The human from which the antibody is extracted may be a human suffering from peanut allergy, a peanut-sensitized human without clinical relevant allergy, a human suffering from peanut allergy that underwent immunotherapy, a human that has outgrown peanut allergy and a human of unknown clinical history for peanut allergy.

In some embodiments, the antibody or binding fragment thereof has an EC50 of at most 270 ng/ml, preferably at most 70 ng/ml, at most 40 ng/ml, at most 25 ng/ml, at most 15 ng/ml, at most 4.9 ng/ml, at most 1.3 ng/ml for at least one of the peanuts allergens selected from the group consisting of Ara h 2, Ara h 1, Ara h 3 and Ara h 6. Preferably, the antibody has an EC50 of at most 10 ng/ml, preferably at most 7 ng/ml, more preferably at most 4.8 ng/ml, most preferably at most 2.8 ng/ml for peanut extract.

The antibodies described herein may be capable of reducing, inhibiting or neutralizing allergen-mediated biological activity. In particular, the antibodies may be capable of reducing or inhibiting the binding of an IgE antibody to the food allergen.

In one embodiment, the antibody or binding fragment thereof comprises a light chain variable region and/or a heavy chain variable region, wherein the light chain variable region comprises a CDR1 set forth in SEQ ID No: 1 or sequences at least 65% identical thereto, a CDR2 set forth in SEQ ID No: 2 or sequences at least 65% identical thereto, a CDR3 set forth in SEQ ID No: 3 or sequences at least 65% identical thereto; wherein the heavy chain variable region comprises a CDR1 set forth in SEQ ID No: 4 or sequences at least 65% identical thereto, a CDR2 set forth in SEQ ID No: 5 or sequences at least 65% identical thereto, and a CDR3 set forth in SEQ ID No: 6 or sequences at least 65% identical thereto.

In another embodiment refers to an antibody or binding fragment thereof comprising a light chain variable region and/or a heavy chain variable region, wherein the light chain variable region comprises a CDR1 set forth in SEQ ID No: 15 or sequences at least 65% identical thereto, a CDR2 set forth in SEQ ID No: 16 or sequences at least 65% identical thereto, a CDR3 set forth in SEQ ID No: 17 or sequences at least 65% identical thereto; wherein the heavy chain variable region comprises a CDR1 set forth in SEQ ID No: 18 or sequences at least 65% identical thereto, a CDR2 set forth in SEQ ID No: 19 or sequences at least 65% identical thereto, a CDR3 set forth in SEQ ID No: 20 or sequences at least 65% identical thereto.

A further embodiment refers to an antibody or binding fragment comprising a light chain variable region and/or a heavy chain variable region, wherein the light chain variable region comprises a CDR1 set forth in SEQ ID No: 29 or sequences at least 65% identical thereto, a CDR2 set forth in SEQ ID No: 30 or sequences at least 65% identical thereto, a CDR3 set forth in SEQ ID No: 31 or sequences at least 65% identical thereto; wherein the heavy chain variable region comprises a CDR1 set forth in SEQ ID No: 32 or sequences at least 65% identical thereto, a CDR2 set forth in SEQ ID No: 33 or sequences at least 65% identical thereto, a CDR3 set forth in SEQ ID No: 34 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 43 or sequences at least 65% identical thereto, a CDR2 set forth in SEQ ID No: 44 or sequences at least 65% identical thereto, a CDR3 set forth in SEQ ID No: 45 or sequences at least 65% identical thereto; and/or wherein the heavy chain variable region comprises a CDR1 set forth in SEQ ID No: 46 or sequences at least 65% identical thereto, a CDR2 set forth in SEQ ID No: 47 or sequences at least 65% identical thereto, a CDR3 set forth in SEQ ID No: 48 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 57 or sequences at least 65% identical thereto, a CDR2 set forth in SEQ ID No: 58 or sequences at least 65% identical thereto, a CDR3 set forth in SEQ ID No: 59 or sequences at least 65% identical thereto; and/or wherein the heavy chain variable region comprises a CDR1 set forth in SEQ ID No: 60 or sequences at least 65% identical thereto, a CDR2 set forth in SEQ ID No: 61 or sequences at least 65% identical thereto, a CDR3 set forth in SEQ ID No: 62 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 71 or sequences at least 65% identical thereto, a CDR2 set forth in SEQ ID No: 72 or sequences at least 65% identical thereto, a CDR3 set forth in SEQ ID No: 72 or sequences at least 65% identical thereto; and/or wherein the heavy chain variable region comprises a CDR1 set forth in SEQ ID No: 74 or sequences at least 65% identical thereto, a CDR2 set forth in SEQ ID No: 75 or sequences at least 65% identical thereto, a CDR3 set forth in SEQ ID No: 76 or sequences at least 65% identical thereto.

The antibodies are described in more detail below.

Preferably, the antibody is selected from the group consisting of a full length antibody, multispecific antibody, a single chain Fv fragment (scFv), a F(ab') fragment, a F(ab')2 fragment, a F(ab)c fragment, a single domain antibody fragment (sdAB) or a multispecific antibody fragment.

Another aspect of the invention refers to an antibody or binding fragment thereof which competes with an antibody as described herein for specific binding to the allergen.

A further aspect refers to a polynucleotide encoding the antibody or binding fragment thereof as described herein. Another embodiment refers to a vector comprising a polynucleotide encoding the antibody or binding fragment thereof as described herein. Another embodiment refers to a cell comprising a polynucleotide encoding the antibody or binding fragment thereof as described herein or a vector comprising a polynucleotide encoding the antibody or binding fragment thereof as described.

A further aspect refers to a method for preparing an anti-allergen antibody or allergen-binding fragment thereof, consisting of culturing the cell comprising a polynucleotide encoding the antibody or binding fragment thereof as described herein and isolating the antibody or allergen binding fragment thereof from the cell or culture medium of the cell.

Moreover, the invention relates to an antibody composition comprising at least two antibodies, wherein at least one of the antibodies is selected from the antibodies as defined herein. In one embodiment the antibody composition comprises at least two of the antibodies selected from the antibodies as defined herein. In one embodiment the antibody composition comprises at least three of the antibodies selected from the antibodies as defined herein.

Another aspect of the invention refers to a pharmaceutical composition comprising at least one of the compounds selected from the group consisting of antibody or binding fragment as described herein, the antibody composition as described herein, the polynucleotide as described herein, the vector as described herein and the cell as described herein.

In one embodiment, the pharmaceutical comprises the antibody or binding fragment of any as described herein or the antibody composition as described herein.

Another embodiment the pharmaceutical composition further comprises an additional agent useful for treating peanut allergy. The additional agent useful for treating peanut allergy may be a β-adrenergic agonist (e.g. epinephrine), antihistamine, corticosteroid, anti-IgE antibody, anti-IgE antibody binding fragment, peptide vaccine and further antibodies capable of binding to a peanut allergen. Preferably, the pharmaceutical composition comprises epinephrine.

Typically, the pharmaceutical composition may comprise a pharmaceutical acceptable carrier.

Preferably, the pharmaceutical composition is intended for subcutaneous, intravenous, intramuscular, intraperitoneal, intranasal and/or inhalative administration. The antibody or binding fragment thereof, in particular the pharmaceutical composition comprising the antibody or binding fragment, may be administered once or more times.

Other aspects of the invention refer to the antibodies or binding fragments, antibody composition, polynucleotide, vector, cell or pharmaceutical composition as described herein for use in the treatment of allergy. The allergy may be a food allergy, such as peanut allergy.

In particular, the invention refers to the antibodies or binding fragments as described herein, the antibody composition as described herein and the pharmaceutical composition as described herein for use in the treatment of food allergy, such as peanut allergy. The treatment may be prophylactic or therapeutic.

Another aspect refers to a method of evaluating the capacity of a candidate antibody or binding fragment thereof to inhibit allergen binding/and/or allergen-induced activity in a human,
wherein the method comprises
(i) incubating the candidate antibody or binding fragment thereof with a composition comprising IgEs derived from the human and a food allergen;
(ii) evaluating whether the candidate antibody inhibits allergen binding/and/or allergen-induced activity in the composition comprising IgEs derived from the human.

Thus, the method of the invention allows to tailor the therapy to the patient based on the predicted response to the antibodies or fragments thereof according to the invention. This approach is also referred as "personalized medicine" approach thereby allows to identify the most effective antibody or antibody combination.

In one embodiment the method further comprises the step of
(iii) determining whether the administration of the candidate antibody is a suitable treatment for a patient suffering from food allergy based on the result of step (ii).

In other words, the present application refers to methods for determining whether a patient suffering from food allergy is responsive to a candidate antibody, comprising the steps of
(i) incubating the candidate antibody or binding fragment thereof with a composition comprising IgEs derived from the human and a food allergen;
(ii) evaluating whether the candidate antibody inhibits allergen binding and/or allergen-induced activity in the composition comprising IgEs derived from the human;
(iii) determining whether the administration of the candidate antibody is a suitable treatment for the patient suffering from food allergy based on the result of step (ii).

Preferably the candidate antibody is an antibody of the invention as described herein.

Preferably, in step (i) the composition comprising IgEs from the allergic patient comprises basophils. Typically, the basophils are derived from the patient. Alternatively, the basophils are donor-derived IgE-stripped basophils.

In one embodiment, basophils are identified based on the low side-scattered light (SSC) and the expression of CCR3. In addition, activated basophils are identified by measuring surface expression of CD63 and/or surface expression of CD203c. Typically, in activated basophils the surface expression of CD63 and/or CD203c is high.

In another embodiment, the secretion of a mediator from leukocytes, in particular basophils, is measured. In a preferred embodiment the mediator is leukotriene, such as sulfidoleukotriene.

The measurement of secreted mediators, in particular leukotriene is advantageous, since the measurement of the mediators, preferably leukotriene, released from the leukocytes, in particular basophils, can be detected by ELISA and therefore can be easily carried out in high-throughput format. Leukotriene is released from the basophils in a dose dependent manner. Thus, it is particularly suitable for highly sensitive assays.

The composition comprising IgEs derived from the human may be plasma, sera, blood, saliva, peripheral blood mononuclear cell (PBMC), leukocytes, basophils or IgEs stripped from basophils.

When measuring secreted mediators, preferably leukotriene, leukocytes may be used as composition comprising IgEs. This makes the assay straight forward, since it is not necessary to distinguish or isolate the basophils from the other cell fractions (such as neutrophils, eosinophils, lymphocytes and monocytes) of the leukocyte pool for measuring secreted mediators.

Another aspect of the invention refers to a method of detecting or quantifying whether an allergen is present in a sample comprising the following steps:

i) incubation of the sample with an antibody of the invention as described herein or with an antibody composition of the invention as described herein, ii) detecting the antibody which is bound to allergen in the sample.

The antibody may be detectably labeled. Alternatively, the antibody is used with a second antibody that is detectably labeled. Preferably, the antibody is unlabeled and used in combination with a second antibody that is detectably labeled. The detectable label may be selected from the group consisting of an enzyme, a radioisotope, a fluorophore, a peptide and a heavy metal.

FIGURE LEGENDS

FIG. 1. histogram distribution of the 84 allergic patients enrolled in the clinical trial described in example 1, total IgG, IgG4, IgE antibody reactivities against major peanut allergens (Ara h 1, 2 and 3). Seroreactivities are expressed as titer, which is defined as OD450 value over background.

Figure 2:
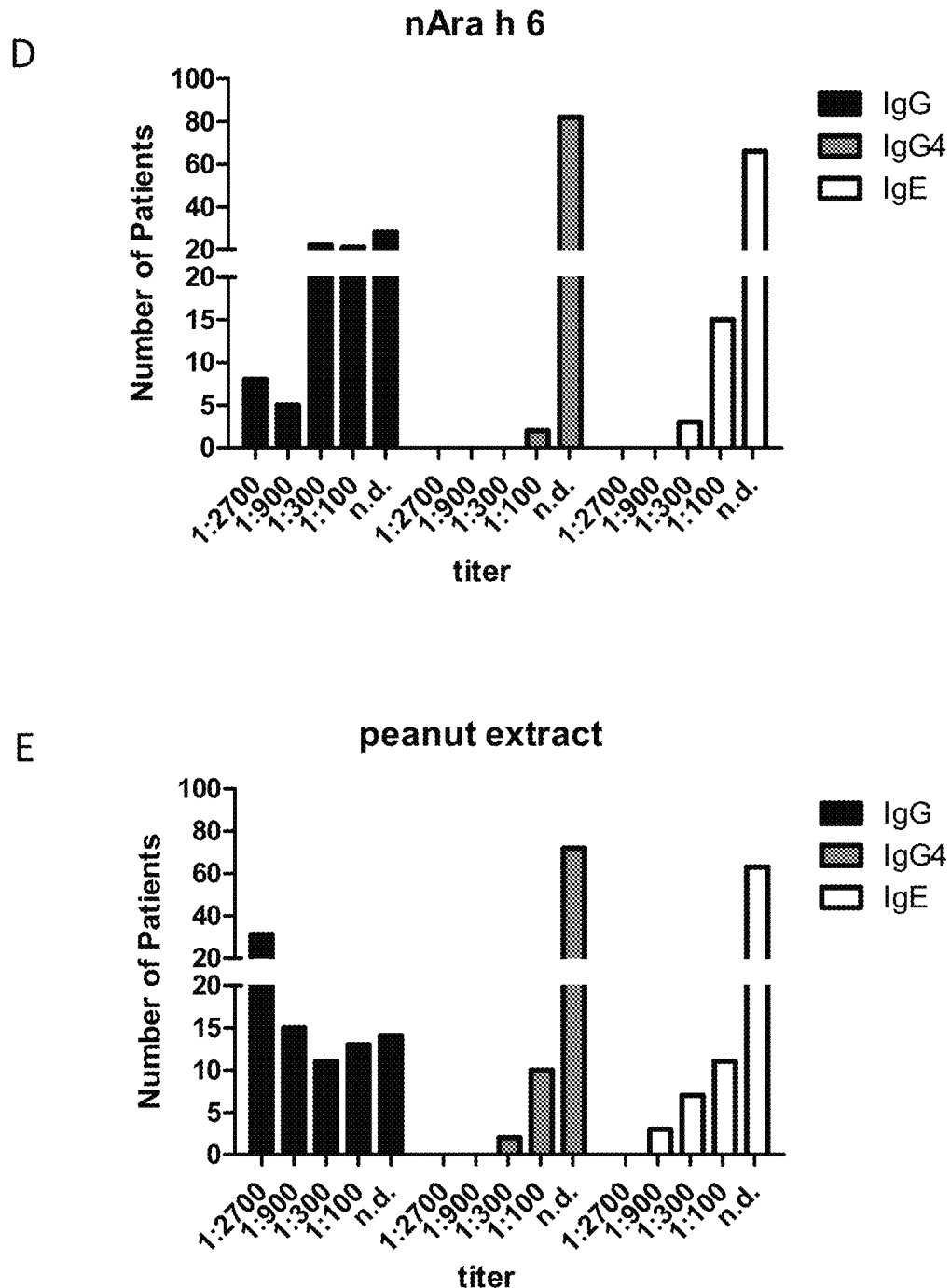

FIG. 2. histogram distribution of the 84 allergic patients enrolled in the clinical trial described in example 1, total IgG, IgG4, IgE antibody reactivities against major peanut allergen Ara h 6 and peanut extract. Seroreactivities are expressed as titer, which is defined as OD450 value over background.

Figure 3:
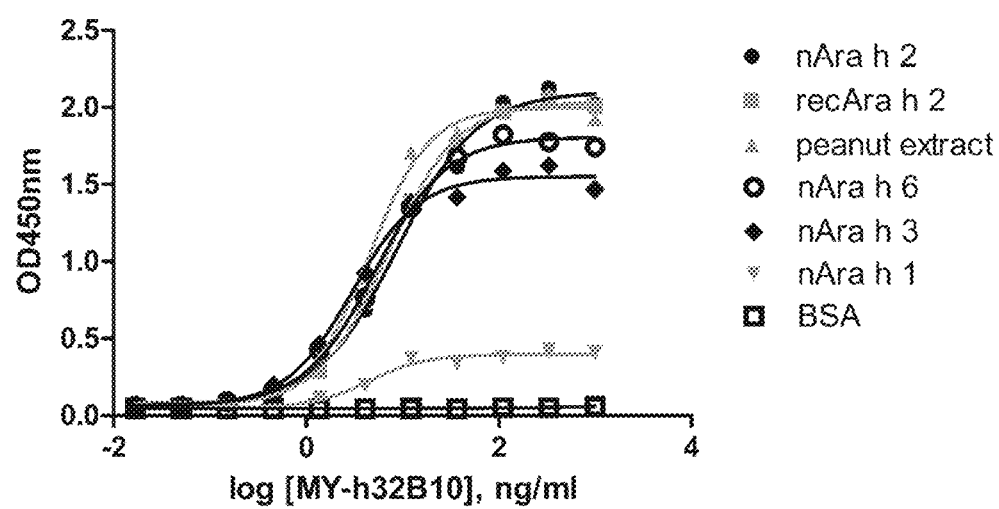

FIG. 3. EC50 ELISA determination of binding of exemplary anti-Ara h 2 antibody 32B10 to naturally extracted peanut allergens (nAra h 1, nAra h 2, nAra h 3, nAra h 6, Indoor Biotechnologies, Cardiff, UK), recombinantly expressed Ara h 2 (rAra h 2, Indoor Biotechnologies, Cardiff, UK) and natural peanut extract. Bovine serum albumin (BSA) serves as control. Similar binding was detected for the antibodies 37D5, 12G10, 4B2, 2F8 and 7G6.

Figure 4:
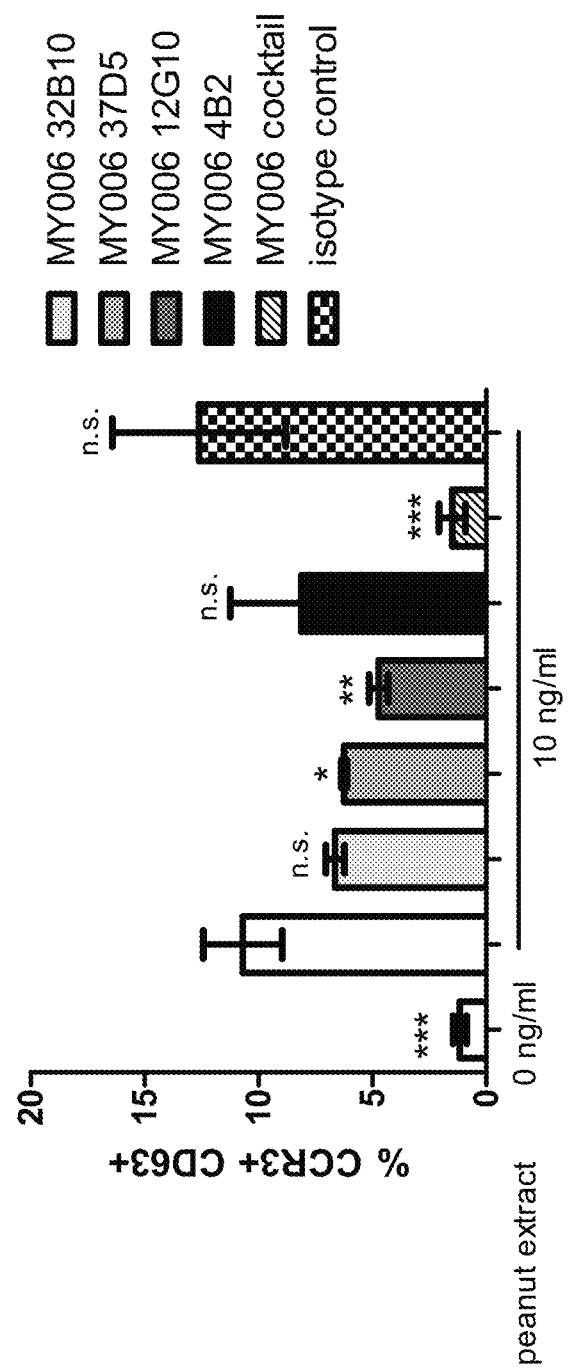

FIG. 4. Human-derived anti-peanut allergen monoclonal antibodies inhibit allergen-mediated activation of basophils derived from allergic patients. Basophils were either left untreated or stimulated with peanut extract in the presence of human-derived antibodies or an isotype control. A. Bars indicate activation of basophils expressed as % CD63+ cells (mean±s.d, n=3). Pre-incubation of peanut extract with exemplary antibodies (32B10, 37D5, 12G10, 4B2) or a combination of them (MY006 cocktail) decreased basophil degranulation, whereas isotype control did not have any effect. White bars: no addition of antibody.

Figure 5:
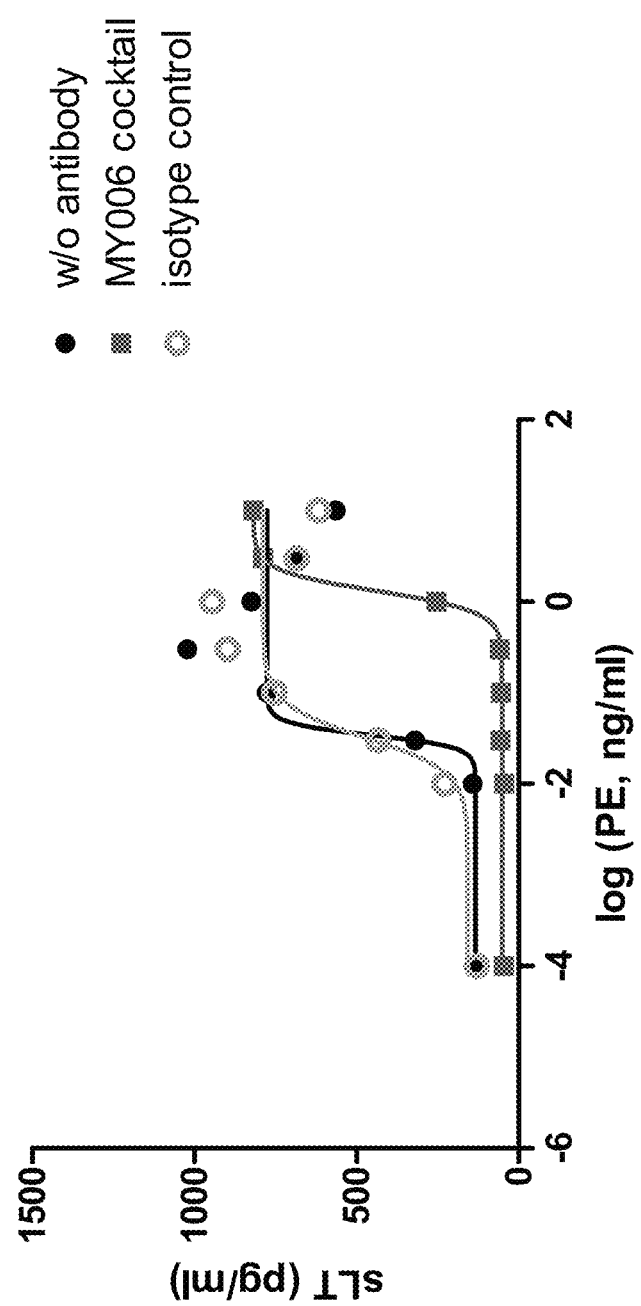

FIG. 5. Human-derived anti-peanut allergen monoclonal antibodies inhibit allergen-mediated release of leukotriene (sLT) from leukocytes derived from allergic patients. Leukocytes were stimulated with increasing concentrations of peanut extract (PE; 0-30 ng/ml) in the presence of a cocktail of human-derived antibodies (MY006) or an isotype control. Pre-incubation of peanut extract with MY006 cocktail inhibited leukotriene release (curve shift to the right), whereas isotype control did not have any effect.

Figure 6:
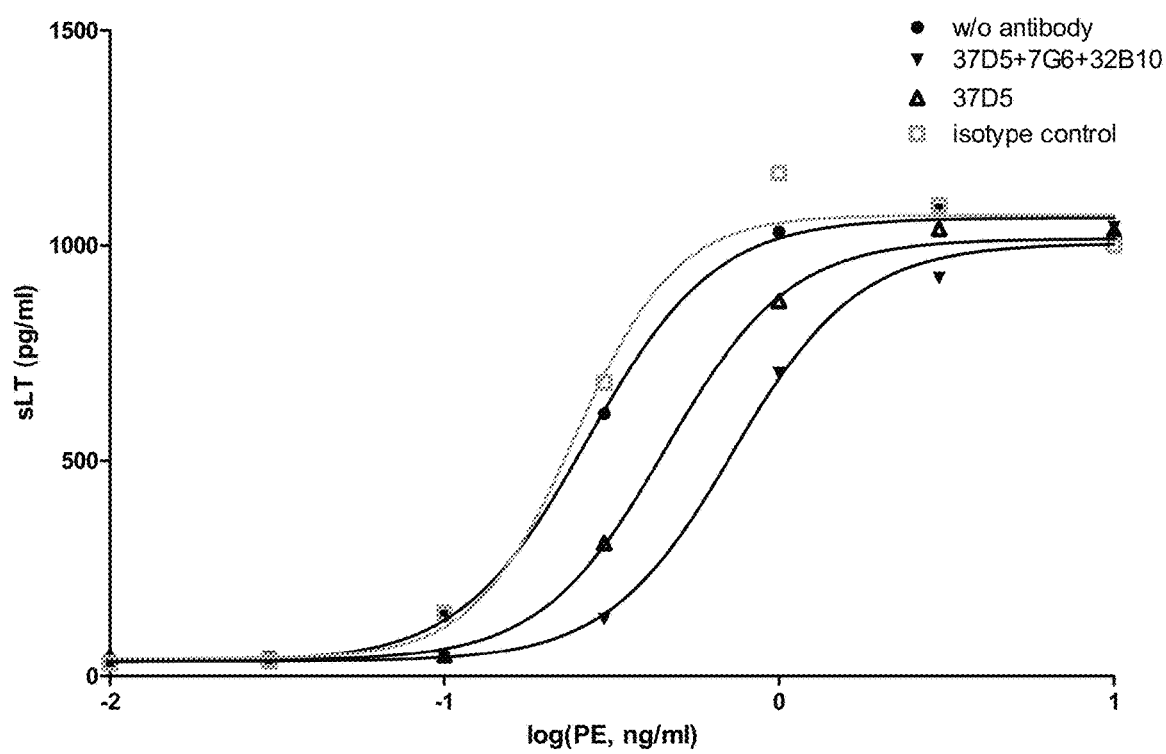

FIG. 6. Effect of different anti-peanut allergen antibody combinations can be evaluated by leukotriene (sLT) release assay. Leukocytes from healthy blood donors were isolated and surface IgE was removed by incubation with lactic acid. Leukocytes were re-sensitized with IgE by incubation with plasma from allergic patients. Re-sensitized leukocytes were stimulated with peanut extract (0-30 ng/ml) in the presence of different human-derived monoclonal anti-peanut allergen antibodies or an isotype control. Pre-incubation of peanut extract (PE) with human-derived anti-peanut allergen antibodies inhibited leukotriene release to different extents, whereas isotype control did not have any effect.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. an antibody is defined to be obtainable from a specific source, this is also to be understood to disclose an antibody which is obtained from this source.

Where an indefinite or definite article is used when referring to a singular noun, e.g. "a", "an" or "the", this includes a plural of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±10%, and preferably of ±5%.

Technical terms are used by their common sense. If a specific meaning is conveyed to certain terms, definitions of terms will be given in the following in the context of which the terms are used.

A first aspect relates to an antibody or binding fragment thereof capable of binding to a food allergen.

The term "capable of binding to a food allergen" as used herein means that the antibody is specific for the allergen, i.e. it recognizes the allergen. Preferably, the antibody has a higher affinity for the specific allergen, i.e. the specific food allergen, such as the peanut allergen Ara h 1, Ara h 2, Ara h 3, Ara h 6 than for other allergens.

The affinity or avidity of an antibody for an antigen can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. The measured affinity of a particular antibody-antigen interaction can vary if measured under different conditions, e.g., salt concentration, pH. Thus, measurements of affinity and other antigen-binding parameters, e.g., $K_D$, IC50, EC50 are preferably made with standardized solutions of antibody and antigen, and a standardized buffer.

Preferably the antibody or binding fragment thereof is human-derived.

The CDRs, the variable and/or the constant regions may stem from the same human-derived antibody. Alternatively, the variable regions, portions thereof or the CDRs are human-derived and are grafted in an antibody framework. This antibody framework may be of human origin. Typically, the human-derived portions of the variable regions that are grafted into the antibody framework comprise the CDRs.

The antibody or binding fragment thereof may comprise a CL and/or CH constant region comprising an amino acid sequence selected from the CL amino acid sequences SEQ ID NOS: 9, 23, 37, 51 and 65 or an amino acid sequence with at least 60% identity and an amino acid sequence selected from the CH amino acid sequences SEQ ID NOS: 10, 24, 38, 52 and 66 or an amino acid sequence with at least 60% identity.

The term "allergen" in the context of the invention is a compound that is recognized by the immune system as foreign so that an immunoreaction to the allergen is evoked. In other words it refers to molecules that are not present in the human body and may produce an abnormal immune response by the activation of mast cells and basophils triggering symptoms of allergy. The skilled person understands that in the context of the invention "autoantigens", i.e. molecules that are produced by the human body are not considered as allergen.

The antibody may be capable of binding a food allergen. Food allergen may be any food that that causes allergy or ingredient thereof, in particular protein. The food allergen may be for example milk, eggs, crustacean, shellfish, tree nuts, peanuts, wheat or soybean or ingredients thereof. In one embodiment the food allergen is peanut or tree nut. In a specific embodiment the food allergen is a legume, such as soybean or peanut. Patients with peanut allergy may have a greater chance of being allergic to other legumes such as soy.

In one embodiment, the allergen is a peanut allergen. The peanut allergen may be untreated or treated peanut, such as roasted peanut. The peanut allergen may be a peanut protein, such as Ara h 1, Ara h 2, Ara h 3, Ara h 4, Ara h 5, Ara h 6/7, Ara h 8, Ara h 9 and Ara h 10/11. In a specific embodiment the peanut protein may be in particular selected from Ara h 1, Ara h 2, Ara h 3 and Ara h 6, or a combination thereof. The peanut allergen may be of peanut origin, recombinantly expressed or is a synthetic peanut peptide.

Typically, the antibody is a monoclonal antibody. In some embodiments, the antibody is a recombinant antibody.

Antibody or binding fragment thereof according to any one of the preceding claims, wherein the antibody is an IgG, such as an IgG1, IgG2, IgG3 or IgG4 antibody, or IgA antibody.

In one embodiment the IgG may be an IgG1, IgG2 or IgG4 antibody.

The term "human-derived" in the context of the present invention means that at least the CDRs are derived from a human antibody. The "human-derived" antibody may contain further elements that are derived from the human antibody, such as parts or the complete framework of the heavy and/or light chain variable regions and/or the parts or the complete of the heavy and/or light chain constant region. For example, the variable regions, portions thereof or the CDRs may be derived from an IgE antibody and grafted in a scaffold of an IgG or IgA antibody. The peptide sequence of the human-derived antibody may be at least 60%, at least 65%, at least 70%, at least 75%, at least 80%, at least 85%, at least 90%, at least 95% or at least 97% identical to the sequence of the antibody extracted from the human. Preferably, the peptide sequence of the human-derived antibody may be at least 90%, at least 95%, at least 97%, at least 98% or at least 99% identical to the sequence of the antibody extracted from the human.

The human from which the antibody is extracted may be selected from the group of a human suffering from peanut allergy, a peanut-sensitized human without clinical relevant allergy, a human suffering from peanut allergy that underwent immunotherapy, a human that has outgrown peanut allergy and a human of unknown clinical history for peanut allergy.

The antibodies of the invention may be used for the prevention or treatment of allergy.

Allergy symptoms may be skin rash, itching skin, itching or tingling sensation in or around the mouth or throat, headache, sneezing, swelling, nausea, diarrhea or anaphylaxis.

In some embodiments, the antibody or binding fragment thereof has an EC50 of at most 270 ng/ml, preferably at most 70 ng/ml, at most 40 ng/ml, at most 25 ng/ml, at most 15 ng/ml, at most 4.9 ng/ml, at most 1.3 ng/ml for at least one of the peanut allergens selected from the group consisting of Ara h 2, Ara h 1, Ara h 3 and Ara h 6. Preferably, the antibody has an EC50 of at most 10 ng/ml, preferably at most 7 ng/ml, more preferably at most 4.8 ng/ml, most preferably 2.8 ng/ml for peanut extract. The EC50 may be measured by an ELISA assay as described herein.

In one embodiment, the antibody or binding fragment thereof comprises a light chain variable region and/or a heavy chain variable region, wherein the light chain variable region comprises a CDR1 set forth in SEQ ID No: 1 or sequences at least 65% identical thereto, a CDR2 set forth in SEQ ID No: 2 or sequences at least 65% identical thereto, a CDR3 set forth in SEQ ID No: 3 or sequences at least 65% identical thereto; wherein the heavy chain variable region comprises a CDR1 set forth in SEQ ID No: 4 or sequences at least 65% identical thereto, a CDR2 set forth in SEQ ID No: 5 or sequences at least 65% identical thereto, and a CDR3 set forth in SEQ ID No: 6 or sequences at least 65% identical thereto.

Another embodiment refers to an antibody or binding fragment thereof comprising a light chain variable region and/or a heavy chain variable region, wherein the light chain variable region comprises a CDR1 set forth in SEQ ID No: 15 or sequences at least 65% identical thereto, a CDR2 set forth in SEQ ID No: 16 or sequences at least 65% identical thereto, a CDR3 set forth in SEQ ID No: 17 or sequences at least 65% identical thereto; wherein the heavy chain variable region comprises a CDR1 set forth in SEQ ID No: 18 or sequences at least 65% identical thereto, a CDR2 set forth in SEQ ID No: 19 or sequences at least 65% identical thereto, a CDR3 set forth in SEQ ID No: 20 or sequences at least 65% identical thereto.

A further embodiment refers to an antibody or binding fragment comprising a light chain variable region and/or a heavy chain variable region, wherein the light chain variable region comprises a CDR1 set forth in SEQ ID No: 29 or sequences at least 65% identical thereto, a CDR2 set forth in SEQ ID No: 30 or sequences at least 65% identical thereto, a CDR3 set forth in SEQ ID No: 31 or sequences at least 65% identical thereto; wherein the heavy chain variable region comprises a CDR1 set forth in SEQ ID No: 32 or sequences at least 65% identical thereto, a CDR2 set forth in SEQ ID No: 33 or sequences at least 65% identical thereto, a CDR3 set forth in SEQ ID No: 34 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 43 or sequences at least 65% identical thereto, a CDR2 set forth in SEQ ID No: 44 or sequences at least 65% identical thereto, a CDR3 set forth in SEQ ID No: 45 or sequences at least 65% identical thereto; and/or wherein the heavy chain variable region comprises a CDR1 set forth in SEQ ID No: 46 or sequences at least 65% identical thereto, a CDR2 set forth in SEQ ID No: 47 or sequences at least 65% identical thereto, a CDR3 set forth in SEQ ID No: 48 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 43 or sequences at least 65% identical thereto, a CDR2 set forth in SEQ ID No: 44 or sequences at least 65% identical thereto, a CDR3 set forth in SEQ ID No: 45 or sequences at least 65% identical thereto; and/or wherein the heavy chain variable region comprises a CDR1 set forth in SEQ ID No: 46 or sequences at least 65% identical thereto, a CDR2 set forth in SEQ ID No: 47 or sequences at least 75% identical thereto, a CDR3 set forth in SEQ ID No: 48 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 57 or sequences at least 65% identical thereto, a CDR2 set forth in SEQ ID No: 58 or sequences at least 65% identical thereto, a CDR3 set forth in SEQ ID No: 59 or sequences at least 65% identical thereto; and/or wherein the heavy chain variable region comprises a CDR1 set forth in SEQ ID No: 60 or sequences at least 65% identical thereto, a CDR2 set forth in SEQ ID No: 61 or sequences at least 65% identical thereto, a CDR3 set forth in SEQ ID No: 62 or sequences at least 65% identical thereto.

A further embodiment refers to an antibody or binding fragment thereof comprising a light chain variable region and/or a heavy chain variable region, wherein the light chain variable region comprises a CDR1 set forth in SEQ ID No: 71 or sequences at least 65% identical thereto, a CDR2 set forth in SEQ ID No: 72 or sequences at least 65% identical thereto, a CDR3 set forth in SEQ ID No: 73 or sequences at least 65% identical thereto; and/or wherein the heavy chain variable region comprises a CDR1 set forth in SEQ ID No: 74 or sequences at least 65% identical thereto, a CDR2 set forth in SEQ ID No: 75 or sequences at least 65% identical thereto, a CDR3 set forth in SEQ ID No: 76 or sequences at least 65% identical thereto.

One embodiment refers to an antibody or binding fragment thereof comprising a light chain variable region and/or a heavy chain variable region, wherein the light chain variable region comprises a CDR1 set forth in SEQ ID No: 1 or sequences at least 91% identical thereto, a CDR2 set forth in SEQ ID No: 2 or sequences at least 71% identical thereto, a CDR3 set forth in SEQ ID No: 3; wherein the heavy chain variable region comprises a CDR1 set forth in SEQ ID No: 4 or sequences at least 80% identical thereto, a CDR2 set forth in SEQ ID No: 5 or sequences at least 82% identical thereto, a CDR3 set forth in SEQ ID No: 6 or a sequence at least 94% identical thereto.

A further embodiment refers to an antibody or binding fragment thereof comprising a light chain variable region and/or a heavy chain variable region, wherein the light chain variable region comprises a CDR1 set forth in SEQ ID No: 71 or sequences at least 91% identical thereto, a CDR2 set forth in SEQ ID No: 72 or sequences at least 71% identical thereto, a CDR3 set forth in SEQ ID No: 73; wherein the heavy chain variable region comprises a CDR1 set forth in SEQ ID No: 74 or sequences at least 80% identical thereto, a CDR2 set forth in SEQ ID No: 75 or sequences at least 82% identical thereto, a CDR3 set forth in SEQ ID No: 76 or sequences at least 94% identical thereto.

A further embodiment refers to an antibody or binding fragment thereof, comprising a light chain variable region and/or a heavy chain variable region, wherein the light chain variable region comprises a sequence set forth in SEQ ID No: 7 or sequences at least 70% identical thereto, and/or wherein the heavy chain variable region comprises a sequence set forth in SEQ ID No: 8 or sequences at least 70% identical thereto.

A further embodiment refers to an antibody or binding fragment thereof, comprising a light chain variable region and/or a heavy chain variable region, wherein the light chain variable region comprises a sequence set forth in SEQ ID No: 21 or sequences at least 70% identical thereto, and/or wherein the heavy chain variable region comprises a sequence set forth in SEQ ID No: 22 or sequences at least 70% identical thereto.

A further embodiment refers to an antibody or binding fragment thereof, comprising a light chain variable region and/or a heavy chain variable region, wherein the light chain variable region comprises a sequence set forth in SEQ ID No: 35 or sequences at least 70% identical thereto, and/or wherein the heavy chain variable region comprises a sequence set forth in SEQ ID No: 36 or sequences at least 70% identical thereto.

A further embodiment refers to an antibody or binding fragment thereof, comprising a light chain variable region and/or a heavy chain variable region, wherein the light chain variable region comprises a sequence set forth in SEQ ID No: 49 or sequences at least 70% identical thereto, and/or wherein the heavy chain variable region comprises a sequence set forth in SEQ ID No: 50 or sequences at least 70% identical thereto.

A further embodiment refers to an antibody or binding fragment thereof, comprising a light chain variable region and/or a heavy chain variable region, wherein the light chain variable region comprises a sequence set forth in SEQ ID No: 63 or sequences at least 70% identical thereto, and/or wherein the heavy chain variable region comprises a sequence set forth in SEQ ID No: 64 or sequences at least 70% identical thereto.

A further embodiment refers to an antibody or binding fragment thereof, comprising a light chain variable region and/or a heavy chain variable region, wherein the light chain variable region comprises a sequence set forth in SEQ ID No: 77 or sequences at least 70% identical thereto, and/or wherein the heavy chain variable region comprises a sequence set forth in SEQ ID No: 78 or sequences at least 70% identical thereto.

A further embodiment refers to an antibody or binding fragment thereof, comprising a light chain variable region and/or a heavy chain variable region, wherein the light chain variable region comprises a sequence set forth in SEQ ID No: 7 or sequences at least 91% identical thereto, and/or wherein the heavy chain variable region comprises a sequence set forth in SEQ ID No: 8 or sequences at least 88% identical thereto.

A further embodiment refers to an antibody or binding fragment thereof, comprising a light chain variable region and/or a heavy chain variable region, wherein the light chain variable region comprises a sequence set forth in SEQ ID No: 77 or sequences at least 91% identical thereto, and/or wherein the heavy chain variable region comprises a sequence set forth in SEQ ID No: 78 or sequences at least 88% identical thereto.

A further embodiment refers to an antibody or binding fragment thereof, comprising in its variable region at least one CDR of the light chain variable region comprising the amino acid sequence SEQ ID NO: 7 and/or the heavy chain variable region comprising the amino acid sequence SEQ ID NO: 8.

A further embodiment refers to an antibody or binding fragment thereof, comprising in its variable region the CDR1, CDR2 and CDR3 of the light chain variable region comprising the amino acid sequence SEQ ID NO: 7 and the heavy chain variable region comprising the amino acid sequence SEQ ID NO: 8.

A further embodiment refers to an antibody or binding fragment thereof, comprising in its variable region at least one CDR of the light chain variable region comprising the amino acid sequence SEQ ID NO: 21 and/or the heavy chain variable region comprising the amino acid sequence SEQ ID NO: 22.

A further embodiment refers to an antibody or binding fragment thereof, comprising in its variable region the CDR1, CDR2 and CDR3 of the light chain variable region comprising the amino acid sequence SEQ ID NO: 21 and the heavy chain variable region comprising the amino acid sequence SEQ ID NO: 22.

A further embodiment refers to an antibody or binding fragment thereof, comprising in its variable region at least one CDR of the light chain variable region comprising the amino acid sequence SEQ ID NO: 35 and/or the heavy chain variable region comprising the amino acid sequence SEQ ID NO: 36.

A further embodiment refers to an antibody or binding fragment thereof, comprising in its variable region the CDR1, CDR2 and CDR3 of the light chain variable region comprising the amino acid sequence SEQ ID NO: 35 and the heavy chain variable region comprising the amino acid sequence SEQ ID NO: 36.

A further embodiment refers to an antibody or binding fragment thereof, comprising in its variable region at least one CDR of the light chain variable region comprising the amino acid sequence SEQ ID NO: 49 and/or the heavy chain variable region comprising the amino acid sequence SEQ ID NO: 50.

A further embodiment refers to an antibody or binding fragment thereof, comprising in its variable region the CDR1, CDR2 and CDR3 of the light chain variable region comprising the amino acid sequence SEQ ID NO: 49 and the heavy chain variable region comprising the amino acid sequence SEQ ID NO: 50.

A further embodiment refers to an antibody or binding fragment thereof, comprising in its variable region at least one CDR of the light chain variable region comprising the amino acid sequence SEQ ID NO: 63 and/or the heavy chain variable region comprising the amino acid sequence SEQ ID NO: 64.

A further embodiment refers to an antibody or binding fragment thereof, comprising in its variable region the CDR1, CDR2 and CDR3 of the light chain variable region comprising the amino acid sequence SEQ ID NO: 63 and the heavy chain variable region comprising the amino acid sequence SEQ ID NO: 64.

A further embodiment refers to an antibody or binding fragment thereof, comprising in its variable region at least one CDR of the light chain variable region comprising the amino acid sequence SEQ ID NO: 77 and/or the heavy chain variable region comprising the amino acid sequence SEQ ID NO: 78.

A further embodiment refers to an antibody or binding fragment thereof, comprising in its variable region the CDR1, CDR2 and CDR3 of the light chain variable region comprising the amino acid sequence SEQ ID NO: 77 and the heavy chain variable region comprising the amino acid sequence SEQ ID NO: 78.

The person skilled in the art knows that each variable domain (the heavy chain $V_H$ and light chain $V_L$) of an antibody comprises three hypervariable regions, sometimes called complementarity determining regions or "CDRs" flanked by four relatively conserved framework regions or "FRs" and refer to the amino acid residues of an antibody which are responsible for antigen-binding. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), J. Mol. Biol. 273:927-948; and Martin et al., (1989), Proc. Natl. Acad. Sci. USA 86:9268-9272. For example, the hypervariable regions or CDRs of the human IgG subclass of antibody comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al., and/or those residues from a hypervariable loop, i.e. residues 26-32 (L1), 50-52 (L2) and 91-96 (L3) in the light chain variable domain and 26-32 (H1), 53-55 (H2) and 96-101 (H3) in the heavy chain variable domain as described by Chothia et al., J. Mol. Biol. 196 (1987), 901-917. Framework or FR residues are those variable domain residues other than and bracketing the hypervariable regions. Accordingly, the term "CDR" refers to the complementarity determining region or hypervariable region amino acid residues of an antibody that participate in or are responsible for antigen-binding. The CDRs as described herein are defined according to Kabat et al. (1991) as described in *Sequences of Proteins of Immunological Interest.*

Binding fragments may thus include portions of an intact full length antibody, such as an antigen binding or variable region of the complete antibody. Examples of antibody fragments include F(ab'), F(ab')2, F(ab)c, and Fv fragments; diabodies; linear antibodies; single-Fv fragments (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), binding-domain immunoglobulin fusion proteins; camelized antibodies; VHH containing antibodies; chimeric antigen receptor (CAR); and any other polypeptides formed from antibody fragments. The skilled person is aware that the antigen-binding function of an antibody can be performed by fragments of a full-length antibody. The binding fragment may have a length of at least 5, at least 8, at least 10, at least 11, at least 12, at least 13, at least 14, at least 15 or more amino acids. The fragment may have the antigen-binding function of the antibody.

The skilled person is aware that also binding molecules capable of binding to a food allergen, in particular a peanut allergen and epitopes thereof, as defined herein, are encompassed by the invention. In particular encompassed are binding molecules capable of binding to a food allergen as defined herein and capable of preventing recognition of food allergens by IgE bound to FCC receptors. Hence the invention also includes all aspects relating to these binding molecules, such as pharmaceutical compositions, kits, therapeutic and diagnostic uses as well as methods relating to these binding molecules. Thus, the term "binding molecule" includes not only antibodies and binding fragments thereof but also includes non-antibody protein scaffold drugs, such as DARPins (for example reviewed in "Challenges and opportunities for non-antibody scaffold drugs", Vazquez-Lombardi R. et al Drug Discovery Today 20 (10): 1271-1283) and other molecules that are not related to peptide structures.

The term "antibody" and "immunoglobulin" are used interchangeably herein. Preferably, the antibody is a full length antibody, multispecific antibody, a single chain Fv fragment (scFv), a F(ab') fragment, a F(ab')2 fragment, a F(ab)c fragment, a single domain antibody fragment (sdAB) or a multispecific antibody fragment.

A Fab fragment consists of the $V_L$, $V_H$, $C_L$ and $C_H1$ domains. An F(ab')2 fragment comprises two Fab fragments linked by a disulfide bridge at the hinge region. An Fd is the $V_H$ and $C_H1$ domains of a single arm of an antibody. An Fv fragment is the $V_L$ and $V_H$ domains of a single arm of an antibody. An F(ab')c fragment comprises two F(ab') fragments plus part of the Fc domain. It is generated e.g. by plasmin digestion.

Binding fragments also encompass monovalent or multivalent, or monomeric or multimeric (e.g. tetrameric), CDR-derived binding domains.

A bispecific antibody comprises two different binding specificities and thus binds to two different antigens or two different epitopes of the same antigen. In one embodiment, the bispecific antibody comprises a first antigen recognition domain that binds to a first antigen and a second antigen recognition domain that binds to a second antigen. In another embodiment the bispecific antibody comprises a first antigen recognition domain that binds to a first epitope of the antigen and a second antigen recognition domain that binds to a second epitope of the antigen.

The determination of percent identity between multiple sequences is preferably accomplished using the AlignX application of the Vector NTI Advance™ 10 program (Invitrogen Corporation, Carlsbad CA, USA). This program uses a modified Clustal W algorithm (Thompson et al., 1994. Nucl Acids Res. 22:pp. 4673-4680; Invitrogen Corporation; Vector NTI Advance™ 10 DNA and protein sequence analysis software. User's Manual, 2004, pp.389-662). The determination of percent identity is performed with the standard parameters of the AlignX application.

In these embodiments the sequence identity may be at least 65%, at least 70%, at least 75%, at least 80%, at least 85%, at least 90%, at least 95% or at least 97%. Preferably, in all these embodiments the sequence identity is at least about 85%, more preferably at least about 90%, even more preferably at least about 95% and most preferably at least about 98% or about 99%. Sequence identity may be determined over the whole length of the respective sequences.

Another aspect of the invention refers to an antibody or binding fragment thereof which competes with an antibody as described herein for specific binding to the allergen. The skilled person is aware of methods for testing the capability of the antibody or binding fragment thereof to compete for specific binding to the allergen, such as the competition ELISA assay as described elsewhere herein.

Some embodiments refer to an antibody which is capable of binding to at least one of the Ara h 2 epitopes selected from the group consisting of the amino acid sequences set forth in SEQ ID NOs: 84, 88, 89, 90 and 91 or fragments thereof.

A particular embodiment refers to an antibody which is capable of binding to the Ara h 2 epitope defined by the amino acid sequence set forth in SEQ ID NO: 84 or fragments thereof.

Another embodiment refers to an antibody which is capable of binding to at least one of the Ara h 2 epitopes selected from the group consisting of the amino acid sequences set forth in SEQ ID NOs: 88, 89, 90 and 91 or fragments thereof.

The fragment of the epitope may comprise at least 5, at least 8, at least 10, at least 11, at least 12, at least 13, at least 14, at least 15, at least 17 or more amino acids.

Another embodiment refers to an antibody which is capable of binding all of the Ara h 2 epitopes selected from the group consisting of the amino acid sequences set forth in SEQ ID NOs: 88, 89, 90 and 91.

Some embodiments refer to an antibody which is capable of binding to at least one of the Ara h 2 epitopes selected from the group consisting of the amino acid sequences set forth in SEQ ID NOs: 84, 88, 89, 90 and 91.

A particular embodiment refers to an antibody which is capable of binding to the Ara h 2 epitope defined by the amino acid sequence set forth in SEQ ID NO: 84.

Another embodiment refers to an antibody which is capable of binding to at least one of the Ara h 2 epitopes selected from the group consisting of the amino acid sequences set forth in SEQ ID NOs: 88, 89, 90 and 91.

Another embodiment refers to an antibody which is capable of binding to all of the Ara h 2 epitopes defined by the amino acid sequences set forth in SEQ ID NOs: 88, 89, 90 and 91.

The antibody or its encoding cDNAs may be further modified. Thus, in a further embodiment the method of the present invention comprises any one of the step(s) of producing a chimeric antibody, single-chain antibody, Fab-fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to the same epitope as that of any one of the antibodies described herein (Schier, Human Antibodies Hybridomas 7 (1996), 97-105; Malmborg, J. Immunol. Methods 183 (1995), 7-13). The production of chimeric antibodies is described, for example, in international application WO89/09622. Methods for the production of humanized antibodies are described in, e.g., European application EP-Al 0 239 400 and international application WO90/07861. As discussed above, the antibody of the invention may exist in a variety of forms besides complete antibodies; including, for example, Fv, Fab and F(ab)2, as well as in single chains; see e.g. international application WO88/09344.

The antibodies of the present invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Modifications of the antibody of the invention include chemical and/or enzymatic derivatizations at one or more constituent amino acids, including side chain modifications, backbone modifications, and N- and C-terminal modifications including acetylation, hydroxylation, methylation, amidation, and the attachment of carbohydrate or lipid moieties, cofactors, and the like. Likewise, the present invention encompasses the production of chimeric proteins which comprise the described antibody or some fragment thereof at the amino terminus fused to heterologous molecule such as an immunostimulatory ligand at the carboxyl terminus; see, e.g., international application WO00/30680 for corresponding technical details.

A further aspect refers to a polynucleotide encoding the antibody or binding fragment thereof as described herein. Another embodiment refers to a vector comprising a polynucleotide encoding the antibody or binding fragment thereof as described herein. Another embodiment refers to a cell comprising a polynucleotide encoding the antibody or binding fragment thereof as described herein or a vector comprising a polynucleotide encoding the antibody or binding fragment thereof as described.

In this respect, the person skilled in the art will readily appreciate that the polynucleotides encoding at least the variable domain of the light and/or heavy chain may encode the variable domains of both immunoglobulin chains or only one. Likewise, said polynucleotides may be under the control of the same promoter or may be separately controlled for expression. Possible regulatory elements permitting expression in prokaryotic host cells comprise, e.g., the $P_L$, lac, trp or tac promoter in *E. coli,* and examples for regulatory elements permitting expression in eukaryotic host cells are the AOX1 or GAL1 promoter in yeast or the CMV-, SV40-, RSV-promoter, CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including a C- or N-terminal identification peptide imparting desired characteristics, e.g., stabilization or simplified purification of expressed recombinant product. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the immunoglobulin light chains, heavy chains, light/heavy chain dimers or intact antibodies, binding fragments or other immunoglobulin forms may follow; see, Beychok, Cells of Immunoglobulin Synthesis, Academic Press, N.Y., (1979).

Furthermore, the present invention relates to vectors, particularly plasmids, cosmids, viruses and bacteriophages used conventionally in genetic engineering that comprise a polynucleotide encoding the antigen or preferably a variable domain of an immunoglobulin chain of an antibody of the invention; optionally in combination with a polynucleotide of the invention that encodes the variable domain of the other immunoglobulin chain of the antibody of the invention. Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells. The vectors containing the polynucleotides of the invention (e.g., the heavy and/or light variable domain(s) of the immunoglobulin chains encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

The present invention furthermore relates to host cells transformed with a polynucleotide or vector of the invention. Said host cell may be a prokaryotic or eukaryotic cell. The polynucleotide or vector of the invention which is present in the host cell may either be integrated into the genome of the host cell or it may be maintained extrachromosomally. The host cell can be any prokaryotic or eukaryotic cell, such as a bacterial, insect, fungal, plant, animal or human cell. Preferred fungal cells are, for example, those of the genus *Saccharomyces,* in particular those of the species *S. cerevisiae.* The term "prokaryotic" is meant to include all bacteria which can be transformed or transfected with a DNA or RNA molecules for the expression of an antibody of the invention or the corresponding immunoglobulin chains. Prokaryotic hosts may include gram negative as well as gram positive bacteria such as, for example, *E. coli, S. typhimurium, Serratia marcescens* and *Bacillus subtilis.* The term "eukaryotic" is meant to include yeast, higher plant, insect and preferably mammalian cells, most preferably HEK293, NSO and CHO cells. Depending upon the host employed in a recombinant production procedure, the antibodies or immunoglobulin chains encoded by the polynucleotide of the present invention may be glycosylated or may be non-glycosylated. Antibodies of the invention or the corresponding immunoglobulin chains may also include an initial methionine amino acid residue. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, NY, 1989). The genetic constructs and methods described therein can be utilized for expression of the antibody of the invention or the corresponding immunoglobulin chains in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Maryland, U.S.A., which is incorporated herein by reference). Furthermore, transgenic animals, preferably mammals, comprising cells of the invention may be used for the large scale production of the antibody of the invention.

A further aspect refers to a method for preparing an anti-allergen antibody or allergen-binding fragment thereof, consisting of culturing the cell comprising a polynucleotide encoding the antibody or binding fragment thereof as described herein and isolating the antibody or allergen binding fragment thereof from the cell or culture medium of the cell.

In a further embodiment, the present invention relates to a method for the production of an antibody or a binding fragment thereof, said method comprising
(a) culturing a cell as described herein; and
(b) isolating said antibody or binding fragment thereof from the culture.

The transformed hosts can be grown in fermentors and cultured according to techniques known in the art to achieve optimal cell growth. Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or its corresponding immunoglobulin chain(s) of the invention can then be isolated from the growth medium, cellular lysates, or cellular membrane fractions. The isolation and purification of the, e.g., recombinantly expressed antibodies or immunoglobulin chains of the invention may be by any conventional means such as, for example, preparative chromatographic separations and immunological separations such as those involving the use of monoclonal or polyclonal antibodies directed, e.g., against the constant region of the antibody of the invention. It will be apparent to those skilled in the art that the antibodies of the invention can be further coupled to other moieties for, e.g., drug targeting and imaging applications. Such coupling may be conducted chemically after expression of the antibody or antigen to site of attachment or the coupling product may be engineered into the antibody or antigen of the invention at the DNA level. The DNAs are then expressed in a suitable host system, and the expressed proteins are collected and renatured, if necessary.

Substantially pure immunoglobulins of at least about 90 to 95% homogeneity are preferred, and 98 to 99% or more homogeneity most preferred, for pharmaceutical uses. Once purified, partially or to homogeneity as desired, the antibodies may then be used therapeutically (including extracorporally) or in developing and performing assay procedures.

The present invention also involves a method for producing cells capable of expressing an antibody of the invention or its corresponding immunoglobulin chain(s) comprising genetically engineering cells with the polynucleotide or with the vector of the invention.

Moreover, the invention relates to an antibody composition comprising at least two antibodies, wherein at least one of the antibodies is selected from the antibodies as defined herein. In one embodiment the antibody composition comprises at least two of the antibodies selected from the antibodies as defined herein. In one embodiment the antibody composition comprises at least three of the antibodies selected from the antibodies as defined herein.

In one embodiment, the antibody composition comprises the antibodies 32B10, 37D5 and 7G6.

Another aspect of the invention refers to a pharmaceutical composition comprising at least one of the compounds selected from the group consisting of antibody or binding fragment as described herein, or the antibody composition as described herein, the polynucleotide as described herein, the vector as described herein and the cell as described herein.

In one embodiment, the pharmaceutical comprises the antibody or binding fragment of any as described herein or the antibody composition as described herein.

In another embodiment the pharmaceutical composition further comprises an additional agent useful for treating peanut allergy. The additional agent useful for treating peanut allergy may be a β-adrenergic agonist, such as epinephrine, antihistamine, corticosteroid, anti-IgE antibody, anti-IgE antibody binding fragment, peptide vaccine and further antibodies capable of binding to a peanut allergen. Preferably, the pharmaceutical composition comprises epinephrine.

Such compositions pharmaceutical comprise a therapeutically or prophylactically effective amount of an antibody or binding fragment thereof in admixture with a suitable pharmaceutical acceptable carrier, e.g., a pharmaceutically acceptable agent.

Pharmaceutically acceptable agents for use in the present pharmaceutical compositions include carriers, excipients, diluents, antioxidants, preservatives, coloring, flavoring and diluting agents, emulsifying agents, suspending agents, solvents, fillers, bulking agents, buffers, delivery vehicles, tonicity agents, co-solvents, wetting agents, complexing agents, buffering agents, antimicrobials, and surfactants.

The composition can be in liquid form or in a lyophilized or freeze-dried form and may include one or more lyoprotectants, excipients, surfactants, high molecular weight structural additives and/or bulking agents (see for example U.S. Pat. Nos. 6,685,940, 6,566,329, and 6,372,716).

Compositions can be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically will be a sterile, pyrogen-free, isotonic aqueous solution, optionally containing pharmaceutically acceptable preservatives. Preferably the pharmaceutical composition is intended for subcutaneous, intravenous, intramuscular, intraperitoneally intranasal and/or inhalative administration.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980, which is incorporated herein by reference.

Pharmaceutical compositions described herein can be formulated for controlled or sustained delivery in a manner that provides local concentration of the product (e.g., bolus, depot effect) and/or increased stability or half-life in a particular local environment. The compositions can include the formulation of antibodies, binding fragments, nucleic acids, or vectors of the invention with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection.

Both biodegradable and non-biodegradable polymeric matrices can be used to deliver compositions of the present invention, and such polymeric matrices may comprise natural or synthetic polymers. Biodegradable matrices are preferred. The period of time over which release occurs is based on selection of the polymer. Typically, release over a period ranging from between a few hours and three to twelve months is most desirable.

Alternatively or additionally, the compositions can be administered locally via implantation into the affected area of a membrane, sponge, or other appropriate material on to which an antibody, binding fragment, nucleic acid, or vector of the invention has been absorbed or encapsulated. Where an implantation device is used, the device can be implanted into any suitable tissue or organ, and delivery of an antibody, binding fragment, nucleic acid, or vector of the invention can be directly through the device via bolus, or via continuous administration, or via catheter using continuous infusion.

A pharmaceutical composition comprising a binding antibody or binding fragment thereof can be formulated for inhalation, such as for example, as a dry powder. Inhalation solutions also can be formulated in a liquefied propellant for aerosol delivery. In yet another formulation, solutions may be nebulized.

Certain formulations containing antibodies or binding fragments thereof can be administered orally. Formulations administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of a selective binding agent. Diluents, flavorings, low melting point waxes, vegetable oils, lubricants, suspending agents, tablet disintegrating agents, and binders also can be employed.

The phrase "therapeutically or prophylactically effective amount" as used herein refers to an amount that produces the desired effect for which it is administered. The exact amount will depend on the purpose of the treatment, and will be ascertainable by one skilled in the art using known techniques (see, for example, Lloyd (2012) The Art, Science and Technology of Pharmaceutical Compounding).

Other aspects of the invention refer to the antibodies or binding fragments, antibody composition, polynucleotide, vector, cell or pharmaceutical composition as described herein for use in the treatment of allergy. The allergy may be a food allergy, such as peanut allergy.

In particular, the invention refers to the antibodies or binding fragments as described herein, the antibody composition as described herein and the pharmaceutical composition as described herein for use in the treatment of food allergy, such as peanut allergy. The treatment may be prophylactic or therapeutic.

Correspondingly, the application relates to methods of treating allergies, in particular food allergies, such as peanut allergy by administering the antibodies or binding fragments, antibody composition, polynucleotide, vector, cell or pharmaceutical composition according to the invention. Preferably, antibodies or binding fragments thereof, the antibody composition and the pharmaceutical composition according to the invention are administered.

Further, the application relates to an antibody or binding fragment thereof, antibody composition, polynucleotide, vector, cell or pharmaceutical composition according to the invention in the manufacture of a medicament for the treatment of allergies, in particular food allergies, such as peanut allergy.

Another aspect refers to a method of evaluating the capacity of an candidate antibody or binding fragment thereof to inhibit allergen binding/and/or allergen-induced activity in an human, wherein the method comprises (i) incubating the candidate antibody or binding fragment thereof, a composition comprising IgEs derived from the human and a food allergen;

(ii) evaluating whether the candidate antibody inhibits allergen binding to IgEs/and/or allergen-induced activity in the composition comprising IgEs derived from the human.

The term "evaluating" comprises "detecting" or "determining" which lead yes or no output and to "measuring" which gives numerical values, such as continuous data values, as output.

In one embodiment the method further comprises the step of (iii) determining whether the administration of the candidate antibody is a suitable treatment for a patient suffering from food allergy based on the result of step (ii).

The administration of the candidate antibody is considered as suitable treatment for a patient suffering from food allergy, if the candidate antibody inhibits allergen binding to IgEs and/or inhibits allergen-induced activity in the composition comprising IgEs derived from the human.

In other words, the invention refers to an in vitro method for determining efficacy of treatment of a subject suffering from food allergy, in particular peanut allergy by treatment with an antibody or fragment thereof according to the invention, comprising determining in vitro whether the candidate antibody inhibits allergen binding to the IgEs and/or inhibits allergen-induced activity in the composition comprising IgEs derived from the human.

Therefore, the present application refers to methods for determining whether a patient suffering from food allergy is responsive to a candidate antibody, comprising the steps of
(i) incubating the candidate antibody or binding fragment thereof, a composition comprising IgEs derived from the patient and an allergen;
(ii) evaluating whether the candidate antibody inhibits allergen binding/and/or allergen-induced activity in the composition comprising IgEs derived from the patient;
(iii) determining whether the administration of the candidate antibody is a suitable treatment for the patient suffering from food allergy based on the result of step (ii).

In a specific embodiment, the present application refers to a method for determining whether a patient suffering from food allergy is responsive to a candidate antibody, comprising the steps of
(i) incubating the candidate antibody or binding fragment thereof, a composition comprising IgEs derived from the patient and an allergen;
(ii) evaluating whether the candidate antibody inhibits allergen binding and/or allergen-induced activity in the composition comprising IgEs derived from the patient by measuring the level of activated leukocytes;
(iii) determining whether the administration of the candidate antibody is a suitable treatment for the patient suffering from food allergy based on the result of step (ii).
wherein decreased levels of activated leukocytes compared to a control indicate that the antibody is capable of inhibiting allergen binding and/or allergen induced activity in the human patient;

Thus, the invention refers to the antibody or binding fragment thereof according to the invention for use in the treatment of food allergy, in particular peanut allergy, of a human wherein the antibody is administered if the antibody or binding fragment thereof inhibits allergen binding to the IgEs and/or inhibits allergen-induced activity in the composition comprising IgEs derived from the human. The skilled person understands that the test whether or not the antibody or binding fragment thereof inhibits allergen binding to the IgEs and/or inhibits allergen-induced activity in the composition comprising IgEs derived from the human is carried out in vitro.

The skilled person is aware of methods for testing the capability of the antibody or binding fragment thereof to compete for the allergen (as described for example in Uermösi et al., Mechanism of allergen-specific desensitization, Allergy, 2010) For example a competition ELISA assay as described in example 4 could be used. In brief, allergen coated plates are incubated with increasing concentration of the antibodies to be tested, e.g. for 1 h at room temperature. Subsequently plates are incubated with the composition comprising the IgEs derived from the human. Total IgE levels can be detected using an appropriate antibody that specifically binds to IgE.

Thus, one embodiment refers to a method of evaluating the capability of a candidate antibody or binding fragment thereof to inhibit allergen binding, comprising the following steps:
(i) incubating the candidate antibody or binding fragment thereof together with a composition comprising IgEs derived from the human and a food allergen;
(ii) measuring the level of IgE bound to antigen;
wherein decreased levels of IgE bound to antigen compared to a control indicate that the antibody is capable of inhibiting allergen binding.

Thereby, decreased levels of IgE bound to antigen compared to the control indicated that the antibody is suitable for the treatment of a patient suffering from food allergy.

Typically, the control comprises IgEs derived from the human and a food allergen but does not contain the candidate antibody. The candidate antibody is an antibody or binding fragment thereof as defined herein.

The skilled person is aware of methods for testing the capability of the antibody or binding fragment thereof to bind to the allergen (see example 2). For example a binding ELISA assay could be used. In brief, allergen coated plates are incubated with increasing concentration of the antibodies to be tested, e.g. for 1 h at room temperature. An appropriate detection antibody is used to measure concentrations/levels of anti-allergen antibody.

The determination whether the antibodies or fragments thereof of the invention inhibit allergen-induced activity in the composition comprising IgEs derived from the human will be ascertainable by one skilled in the art using known techniques (see, for example Hausmann et al., Robust expression of CCR3 as single basophil marker', Allergy, 2011).

For example the Basophil activation test could be used. In brief the allergen was preincubated with one or serial dilutions of the candidate antibody. Afterwards, 100 µl of whole blood of the patient were stimulated with the allergen or stimulation buffer (negative control) in the presence/absence of the candidate antibody or isotype control for 30 minutes at 37° C., 5% CO2. Cells are simultaneously stained with anti-CCR3-APC, anti-CD203c-PE and anti-CD63-FITC (Biolegend, San Diego, CA, USA). Basophils are gated as SSClow, CCR3high lymphocytes. At least 500 basophils are acquired using e.g. a FACSCalibur (Becton Dickinson AG, Allschwil, Switzerland). Activation of basophils is quantified using % of CD63+ CCR3+ basophils.

The term "isotype control" as used herein refers to an antibody of the same isotype and having the same constant region as the candidate antibody but being not specific for the allergen.

Thus, one embodiment refers to a method of evaluating the capability of a candidate antibody or binding fragment thereof to inhibit allergen binding and/or allergen-induced activity in a human, comprising the following steps:
(i) incubating the candidate antibody or binding fragment thereof together with basophils derived from the human and a food allergen;
(ii) measuring the level of activated basophils;
wherein decreased levels of activated basophils compared to a control indicate that the antibody is capable of inhibiting allergen binding and/or allergen induced activity in a human.

Thereby, decreased levels of activated basophils compared to the control indicated that the antibody is suitable for the treatment of a patient suffering from food allergy.

Typically, the control comprises basophils derived from the human and a food allergen but does not contain the candidate antibody.

Preferably the candidate antibody is an antibody or binding fragment thereof according to the invention.

The skilled person understands that the step of determining whether candidate antibody inhibits allergen binding to the IgEs and/or inhibits allergen-induced activity in the composition comprising IgEs also encompasses that several candidate antibodies or fragments thereof are tested on the same sample together (are pooled) in a first step, and if the result is positive (i.e. that the allergen binding and/or allergen-induced activity is inhibited), then in a second step the candidate antibodies or fragments thereof are tested individually. Alternatively, the candidate antibodies are already tested individually in the first step.

Preferably, in step (i) the composition comprising IgEs from the human, in particular the allergic patient comprises basophils. Typically, the basophils are derived from the allergicpatient. Alternatively, the basophils are donor-derived IgE-stripped basophils.

"IgE-stripped basophils" may be produced by incubating basophils with lactic acid, in order to strip off the IgEs from the donor. In order to furnish the stripped basophils with patient derived IgEs, the IgE-stripped basophils may be incubated with plasma from an allergic patient.

For the identification of basophils, in particular activated basophils, cell sorting such as fluorescent activated cell sorting could be used. In one embodiment, basophils are identified based on the low side-scattered light (SSC) and the expression of CCR3. In addition, activated basophils are identified by measuring surface expression of CD63 and/or surface expression of CD203c. Typically, in activated basophils the surface expression of CD63 and/or CD203c is high.

The composition comprising IgEs derived from the human may be plasma, sera, blood, saliva, peripheral blood mononuclear cell (PBMC), leukocytes, basophils or IgEs stripped from basophils.

In a specific embodiment, evaluating the capability of a candidate antibody or binding fragment thereof to inhibit allergen binding and/or allergen-induced activity is accomplished by an assay measuring an inflammatory mediator released from the basophil, preferably leukotriene. This assay is advantageous, since the measurement of the leukotriene released from the basophils can be detected by ELISA and therefore can be easily carried out in high-throughput format. The leukotriene release assay allows to evaluate the capability of a candidate antibody or binding fragment thereof to inhibit allergen binding and/or allergen-induced activity with high sensitivity, reliability and cost effectiveness.

In assays which determine the basophil activation by measuring the secretion of the inflammatory mediator, in particular leukotriene, from the basophils, the IgE containing composition may be isolated leukocytes. The leukocytes may be either derived from an allergic patient or may be donor-derived leukocytes, from which the IgEs from the donor are stripped-off and replaced by IgEs derived from an allergic patient.

The skilled person understands that leukotrienes may be secreted also by mast cells, eosinophils, neutrophils. However, in this experimental set-up, the leukotriene secretion from these cell types is neglectable in comparison to the secretion of leukotrienes by basophils.

The leukotriene assay is described in detail in the examples. In brief, leukocytes may be isolated by dextran sedimentation from whole blood of allergic patients. Titrations of peanut extract are preincubated with purified antibody samples. Afterwards, leukocytes are stimulated with titrated peanut extract or stimulation buffer (negative control) in the presence/absence of different anti-peanut allergen antibodies or isotype control. Activation of leukocytes, in particular, basophils is quantified using CAST®ELISA (Bühlmann, Schönenbuch, Switzerland).

"Leukotriene" as used herein refers to a family of eicosanoid inflammatory mediators. In particular, the term "leukotriene" refers to sulfidoleukotrienes, also termed cysteinyl leukotrienes, such as LTC4 and its metabolites LTD4 and LTE4.

Leukotriene is released by activated basophils. Thus decreased leukotriene levels detected for the candidate antibody or binding fragment thereof compared to a control sample indicate that the antibody is capable of inhibiting allergen binding and/or allergen induced activity in a human.

Leukotriene is released from the basophils in a dose dependent manner. Thus, it is particularly suitable for highly sensitive assays.

Therefore, the methods described above can be used to compare the different candidate antibodies for the capability to treat peanut allergy, wherein a first candidate antibody leading to a lower activation of the basophils, e.g. indicated by a lower secretion of leukotriene in comparison to a second candidate antibody, indicates that the first candidate antibody is particularly suited for treating peanut allergy.

Accordingly, one embodiment refers to a method of evaluating the capability of a candidate antibody or binding fragment thereof to inhibit allergen binding and/or allergen-induced activity in a human, comprising the following steps:

(i) incubating the candidate antibody or binding fragment thereof together with a composition comprising IgEs derived from the human and a food allergen;

(ii) evaluating whether the candidate antibody inhibits allergen binding/and/or allergen-induced activity in the composition comprising IgEs derived from the patient by measuring the leukotriene secretion;

wherein decreased levels of leukotriene secretion compared to a control indicate that the antibody is capable of inhibiting allergen binding and/or allergen induced activity in a human.

In another preferred embodiment, the present application refers to a method for determining whether a patient suffering from food allergy is responsive to a candidate antibody, comprising the steps of (i) incubating the candidate antibody or binding fragment thereof, a composition comprising IgEs derived from the patient and an allergen;

(ii) evaluating whether the candidate antibody inhibits allergen binding/and/or allergen-induced activity in the composition comprising IgEs derived from the patient by measuring the leukotriene secretion;

(iii) determining whether the administration of the candidate antibody is a suitable treatment for the patient suffering from food allergy based on the result of step (ii).

wherein decreased levels of leukotriene secretion compared to a control indicate that the antibody is capable of inhibiting allergen binding and/or allergen induced activity in the human patient;

Another aspect of the invention refers to a method of detecting or quantifying whether an allergen is present in a sample comprising the following steps:

i) incubation of the sample with an antibody of the invention as described herein or with an antibody composition of the invention as described herein, ii) detecting the antibody which is bound to allergen in the sample.

The antibody may be detectably labeled. Alternatively, the antibody is used with a second antibody that is detectably labeled. Preferably, the antibody is unlabeled and used in combination with a second antibody that is detectably labeled. The detectable label may be selected from the group consisting of an enzyme, a radioisotope, a fluorophore, a peptide and a heavy metal.

Labeling agents can be coupled either directly or indirectly to the antibodies or antigens of the invention. One example of indirect coupling is by use of a spacer moiety. Furthermore, the antibodies of the present invention can comprise a further domain, said domain being linked by covalent or non-covalent bonds. The linkage can be based on genetic fusion according to the methods known in the art and described above or can be performed by, e.g., chemical cross-linking as described in, e.g., international application WO94/04686. The additional domain present in the fusion protein comprising the antibody of the invention may preferably be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the antibody of the invention or vice versa. The therapeutically or diagnostically active agent can be coupled to the antibody of the invention or an antigen-binding fragment thereof by various means. This includes, for example, single-chain fusion proteins comprising the variable regions of the antibody of the invention coupled by covalent methods, such as peptide linkages, to the therapeutically or diagnostically active agent. Further examples include molecules which comprise at least an antigen-binding fragment coupled to additional molecules covalently or non-covalently include those in the following non-limiting illustrative list.

EXPERIMENTS

Examples

The following examples further illustrate the invention, but should not be construed to limit the scope of the invention in any way. Detailed descriptions of conventional methods, such as those employed herein can be found in the cited literature. The practice of the present invention will employ, unless otherwise indicated, conventional techniques of cell biology, cell culture, molecular biology, transgenic biology, microbiology, recombinant DNA, and immunology, which are within the skill of the art.

Material and Methods

Patients Selection and Disease Associations of the Invention

As starting material for the cloning of fully human antibodies, human lymphocytes were obtained from peripheral blood of 84 voluntary allergic patients. All patients gave their written informed consent and the study has been approved by the ethical Committee of Zurich. Clinical reactivity was defined based on anamnesis of signs of allergic reactions (e.g. oral allergy syndrome, angioedema, dyspnea, nausea, emesis, diarrhea, shock) and/or positive skin prick test or presence of serum IgE antibodies (ImmunoCAP, Phadia, Uppsala, Sweden).

Isolation of Memory B Cells Reactive to Peanut Allergens

Antibodies specific to major peanut allergens were isolated by molecular cloning of immunoglobulin genes obtained from single-cell sorted cells derived from short term oligoclonal cultures of activated memory B cells producing the antibodies of interest.

Isolation of PBMC and Memory B Cell Culture

Peripheral blood mononuclear cells (PBMCs) were isolated from heparinized peripheral blood using Lympholyte H according to manufacturer's instruction (Cedarlane, Burlington, Ontario, Canada) and cryopreserved prior to use.

Cells were stained on ice with monoclonal antibodies phycoerythrin-conjugated anti-human IgD and IgA, APC-conjugated mAbs anti-human IgM, CD3, CD56, CD8, and FITC-conjugated mAb anti-human CD22 (Becton Dickinson, Basel, Switzerland). Cells sorting was carried out using a MoFlo XDP cell sorter (Beckman Coulter, Krefeld, Germany). CD22 positive and IgM, IgD, IgA negative B cells were seeded at 5-10 cells per well on irradiated CD40L-expressing feeder cells stimulated with a cytokine cocktail, as described in Huang et al., Isolation of human monoclonal antibodies from peripheral blood cells', Nature Protocols, 2012.

After 10-14 days of stimulation, culture supernatants were screened for the presence of IgG or IgE antibodies specific for the target of interest (e.g. Ara h 1, Ara h 2, Ara h 3, Ara h 6, peanut extract). The screening process comprised for binding on recombinant or naturally extracted peanut allergens of the particular molecule of interest (e.g. by ELISA). Detection of peanut-specific IgE or IgG antibodies is performed using anti-human HRP-conjugated Fc-epsilon-specific secondary antibody (Abcam, Cambridge, UK) or anti-human HRP-conjugated goat Fc-gamma-specific antibody (Jackson ImmunoResearch, West Grove, PA, USA) followed by measurement of the HRP activity using a tetramethylbenzidine substrate solution (TMB, Sigma-Aldrich Chemie GmbH, Buchs, Switzerland). Subsequently the antibody for which binding is detected or the cell producing said antibody is isolated.

Molecular Cloning of Human Antibodies Specific to Peanut Allergens

Molecular cloning of human antibodies specific to peanut allergens is carried out according to Huang et al., Isolation of human monoclonal antibodies from peripheral blood cells', Nature Protocols, 2012. In particular, single cells obtained from peanut allergen-reactive memory B cell cultures are sorted into a 96 well PCR plate, containing reverse-transcription buffer (Invitrogen, Carlsbad, Calif., United States). cDNA preparation is done using Random Hexamer Primer (Invitrogen, Carlsbad, CA, United States) according to the supplier's protocol. Immunoglobulin heavy and light chain variable regions ($V_H$ and $V_L$, respectively) are PCR amplified according to standard protocols (Wardemann et al, Science 301, 2003, 1374-1377). To increase the PCR efficiency, a nested PCR is performed. The first round PCR is performed with primers specific for the IgG and IgE constant region and primer mixes specific to all leader sequences from $V_H$ and $V_L$ families (Wardemann et al, Science 301, 2003, 1374-1377). Subsequently, a nested PCR is performed using primer mixes specific to the 5' region of framework 1 of $V_H$ and $V_L$ families (V-region) and the immunoglobulin J-regions. Sequence analysis is carried out to identify individual antibody clones present in the selected B cell culture. Afterwards, the $V_H$ and $V_L$ of each unique antibody clone are cloned into expression vectors providing the constant regions of human IgG1, human Ig-Kappa or human Ig-Lambda. Upon co-transfection of the Ig-heavy- and light expression vectors into HEK293T cells, the respective antibody clones are produced. Identification of the antibody clone presumably responsible for the anti-peanut reactivity of the parental B cell culture is performed upon re-screening of the recombinant antibodies for reactivity to peanut allergens in an ELISA.

In order to identify and to correct primer encoded sequence mismatches in the Ig-variable regions, an additional PCR amplification on original cDNA of the reactive clone is performed using a semi-nested PCR. Therefore, primer mixes specific for the Ig heavy and light chain leader sequences (5'-primers) and two primer pairs specific for a conserved region of the Ig heavy and light chain constant regions (3'-primers) are used. PCR products are cloned into pCR™2.1-TOPO® vector (Invitrogen, Carlsbad, CA, United States) and subsequently sequenced using standard primers. Alternatively, PCR products are directly subjected to sequencing using internal primers specific to conserved regions of the constant domains of heavy and light chains. Sequence determination and annotation of the complete antibody is carried out and this information is used to design specific primers for the cloning of the authentic human $V_H$ and $V_L$ sequence into antibody (IgG) expression vectors. This approach also allows the identification of Ig isotype (and subclass) of each isolated, reactive monoclonal antibody. These $V_H$ and $V_L$ sequences are then used for the production of recombinant antibodies which are subsequently characterized in more detail.

The sequences of the antibodies are set out in Table 1.

TABLE 1

Antibody sequences. Underlined, bold nucleotides or amino acids indicate the CDRs in the sequence of the variable domain. Italic nucleotides or amino acids indicate sequences which have not been sequenced but obtainedfrom database.

| Antibody | Nucleotide and amino acid sequences of variable heavy (VH) and variable light (VL), constant heavy (CH) and constant light (CL) chains. | Seq. ID |
|---|---|---|
| 37D5 VH DNA | gaggaacagctggtggagtctggggacgtttattacggcctggggagtccctgagcctctcctgt gcagccgttggattcaacttcggtgattttggcatggcctgggtccgccaacctccagggaaggg gctggagtgggtcgctggcatcaattggagtggccatagtacaggttttgtagactccatgaa gggtcgactcaccatctccagagacagcgccaagagttccctgtttctgcaaatgaacagtctgcg aggcgaggacacggccgtgtattactgtgcgagagtcgggagactttgtagtggagatatttgc gactcaatgggtgcttttgatctgtggggcaggggacaatggtcaccgtctcttca | 12 |
| 37D5 VH amino acid | EEQLVESGGRLLRPGESLSLSCAAVGFNFGDFGMAWVRQPPG KGLEWVAINWSGHSTGFVDSMKGRLTISRDSAKSSLFLQM NSLRGEDTAVYYCARVGRLCSGDICDSMGAFDLWGQGTMV TVSS | 8 |
| 37D5 VL kappa-type DNA | gacatccagatgacccagtctcctccaccctgtctgcatctataggagacagagtcaccatcactt gtcggggccagtcagaccattgacaactggttggcctggtatcaacagagaccagggaaagcc cctaaactcctgatctatcaggcgtctagtctacaaagtggggtctcatcaaggttcagaggcagt ggatctggcacagaattcactctcaccatcaccagcctgcagcctgatgactttgctacttattattgt cagaagtctaatggctattctcgtactttcggccaggggaccaaggtggagatcaaa | 11 |
| 37D5 VL kappa-type amino acid | DIQMTQSPSTLSASIGDRVTITCRASQTIDNWLAWYQQRPGK APKLLIYQASSLQSGVSSRFRGSGSGTEFTLTITSLQPDDFATY YCQKSNGYSRTFGQGTKVEIK | 7 |
| 37D5 CH IgG1 subclass DNA | gcctccaccaagggcccatcggtcttccccctggcaccctcctccaagagcacctctgggggcac agcggccctgggctgcctggtcaaggactacttccccgaaccggtgacggtgtcgtggaactca ggcgccctgaccagcggcgtgcacaccttcccggctgtcctacagtcctcaggactctactccctc agcagcgtggtgaccgtgccctccagcagcttgggcacccagacctacatctgcaacgtgaatca caagcccagcaacaccaaggtggacaagaaagttgagcccaaatcttgtgacaaaactcacacat gcccaccgtgcccagcacctgaactcctggggggaccgtcagtcttcctcttccccccaaaaccc aaggacaccctcatgatctcccggacccctgaggtcacatgcgtggtggtggacgtgagccacg aagaccctgaggtcaagttcaactggtacgtggacggcgtggaggtgcataatgccaagacaaa gccgcgggaggagcagtacaacagcacgtaccgtgtggtcagcgtcctcaccgtcctgcaccag gactggctgaatggcaaggagtacaagtgcaaggtctccaacaaagcccctcccagccccatcg agaaaaccatctccaaagccaaagggcagccccgagaaccacaggtgtacaccctgcccccat cccgggatgagctgaccaagaaccaggtcagcctgacctgcctggtcaaaggcttctatcccagc gacatcgccgtggagtgggagagcaatgggcagccggagaacaactacaagaccacgcctcc cgtgctggactccgacggctccttcttcctctacagcaagctcaccgtggacaagagcaggtggc agcaggggaacgtcttctcatgctccgtgatgcatgaggctctgcacaaccactacacgcagaag agcctctccctgtctccgggtaaatga | 14 |
| 37D5 CH IgG1 subclass amino acid | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSRDELTKNQVSLTCLVKGF YPSDIAVEWESNGQPENNYKTTPPVLDSDGSFFLYSKLTVDKS RWQQGNVFSCSVMHEALHNHYTQKSLSLSPGK | 10 |
| 37D5 CL kappa-type DNA | cgaactgtggctgcaccatctgtcttcatcttcccgccatctgatgagcagttgaaatctggaactgc ctctgttgtgtgcctgctgaataacttctatcccagagaggccaaagtacagtggaaggtggataac gccctccaatcgggtaactcccaggagagtgtcacagagcaggacagcaaggacagcacctac agcctcagcagcaccctgacgctgagcaaagcagactacgagaaacacaaagtctacgcctgc gaagtcacccatcagggcctgagctcgcccgtcacaaagagcttcaacaggggagagtgttag | 13 |
| 37D5 CL kappa-type amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC | 9 |

TABLE 1-continued

Antibody sequences. Underlined, bold nucleotides or amino acids indicate the CDRs in the sequence of the variable domain. Italic nucleotides or amino acids indicate sequences which have not been sequenced but obtained from database.

| Antibody | Nucleotide and amino acid sequences of variable heavy (VH) and variable light (VL), constant heavy (CH) and constant light (CL) chains. | Seq. ID |
|---|---|---|
| 32B10 VH DNA | caggtgcagctggtgcagtctggggctgaggtgaagaagcctggggcctcagtgaaggtctcct gcagggcttctggatacatcttccgcaactttgatatcaactgggtgcgacaggccactggacaa gggcttgagtggatgggatggatgagccctaagagtggtgacaccggctatgctcagaagtt ccagggcagggtcaccatgaccagggacacctccataaacacagcctacatggaactgagcag cctgacatctgaggattcggccgtctattactgtgcgagaggtgtcgacgggaccaactggggc cagggaacccgggtcaccgtctcctca | 26 |
| 32B10 VH amino acid | QVQLVQSGAEVKKPGASVKVSCRASGYIFRNFDINWVRQAT GQGLEWMGWMSPKSGDTGYAQKFQGRVTMTRDTSINTAY MELSSLTSEDSAVYYCARGVDGTNWGQGTRVTVSS | 22 |
| 32B10 VL kappa-type DNA | gacatcgtgatgacccagtctccagactccctgggtgtgtctctgggcgagagggccaccatcag ctgcaagtccagccagagtattttagataaactccaacaataagaacttcatagcttggttcca gcagaaaccaggacagcccctaagctgctcatttacttgggcatctgcccgggaatccggggtc cctgaccgattcagtggcagcgggtctgggacagaattcactctcaccatcaacagcctgcaggc tgaagatgtggcagtttattactgttaccaatactattctactcctcacacttttggccaggggacc aagctggatctcaga | 25 |
| 32B10 VL kappa-type amino acid | DIVMTQSPDSLGVSLGERATISCKSSQSILDNSNNKNFIAWFQ QKPGQPPKLLIYWASARESGVPDRFSGSGSGTEFTLTINSLQA EDVAVYYCYQYYSTPHTFGQGTKLDLR | 21 |
| 32B10 CH IgG2 subclass DNA | gcttccaccaagggcccatccgtcttccccctggcgccctgctccaggagcacctccgagagcac agccgccctgggctgcctggtcaaggactacttccccgaaccggtgacggtgtcgtggaactcag gcgctctgaccagcggcgtgcacaccttcccagctgtcctacagtctcctaggactctactccctca gcagcgtggtgaccgtgacctccagcaacttcggcacccagacctacacctgcaacgtagatcac aagcccagcaacaccaaggtggacaagacagttgagcgcaaatgttgtgtcgagtgcccaccgt gcccagcaccacctgtggcaggaccgtcagtcttcctcttccccccaaaacccaaggacaccctc atgatctcccggacccctgaggtcacgtgcgtggtggtggacgtgagccacgaagaccccgagg tccagttcaactggtacgtggacggcgtggaggtgcataatgcaaagacaaagccacgggagg agcagttcaacagcacgttccgtgtggtcagcgtcctcaccgttgtgcaccaggactggctgaa cggcaaggagtacaagtgcaaggtctccaacaaaggcctcccagcccccatcgagaaaacc atctccaaaaccaaagggcagccccgagaaccacaggtgtacaccctgccccccatcccggg aggagatgaccaagaaccaggtcagcctgacctgcctggtcaaaggcttctaccccagcgac atcgccgtggagtgggagagcaatgggcagccggagaacaactacaaggccacacctccc atgctggactccgacggctccttcttcctctacagcaagctcaccgtggacaagagcaggtggc agcaggggaacgtcttctcatgctccgtgatgcatgaggctctgcacaaccactacacgcaga gagcctctccctgtctccgggtaaatga | 28 |
| 32B10 CH IgG2 subclass amino acid | ASTKGPSVFPLAPCSRSTSESTAALGCLVKDYFPEPVTVSWNS GALTSGVHTFPAVLQSSGLYSLSSVVTVTSSNFGTQTYTCNVD HKPSNTKVDKTVERKCCVECPPCPAPPVAGPSVFLFPPKPKDT LMISRTPEVTCVVVDVSHEDPEVQFNWYVDGVEVHNA*KTKP REEQFNSTFRWSVLTWHQDWLNGKEYKCKVSNKGLPAPIEKTI SKTKGQPREPQVYTLPPSREEMTKNQVSLTCLVKGFYPSDIAVEW ESNGQPENNYKATPPMLDSDGSFFLYSKLTVDKSRWQQGNVFSC SVMHEALHNHYTQKSLSLSPGK* | 24 |
| 32B10 CL kappa-type DNA | cgaactgtggctgcaccatctgtcttcatcttcccgccatctgatgagcagttgaaatctggaactgc ctctgttgtgtgcctgctgaataacttctatcccagagaggccaaagtacagtggaaggtggataac gccctccaatcgggtaactcccaggagagtgtcacagagcaggacagcaaggacagcacctac agcctcagcagcaccctgacgctgagcaaagcagactacgagaaacacaaagtctacgcctgc gaagtcacccatcagggcctgagctcgcccgtcacaaagagcttcaacaggggagagtgttag | 27 |
| 32B10 CL kappa-type amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC | 23 |
| 2F8 VH DNA | gaagatgtccagtgtgaggtgcagctggtggagtctggggaggcttggtcaagccggggggg tcgctgagactctcctgtgcagcgtctggattcatcttcagcgattataacatgaattgggtccgcc aggctccagggaaggggctggagtgggttttcatccattactagaagtagtaggaccatttact acgcagactctgtgaagggccgattcaccatatccagagacaatgccaagaactcactgcatct gcaaatgaacagtctcagagacgcggacacggctgtgtattattgtgcgagagaggattcgatg tttcgactggcccctactacatggacgtctgggggcaacgggaccacggtcatcgtctcctca | 40 |
| 2F8 VH amino acid | EVQLVESGGGLVKPGGSLRLSCAASGFIFSDYNMNWVRQAP GKGLEWVSSITRSSRTIYYADSVKGRFTISRDNAKNSLHLQM NSLRDADTAVYYCAREDFDVSTGPYYMDVWGNGTTVIVSS | 36 |
| 2F8 VL kappa-type | gaaattgtgttgacgcagtctccaggcacccctgtctttgtctcaggggaaagagccaccctctcct gcagggccagtcagagtgttagcaacatgttcttagtctggtatcagcagaaacctggccagg | 39 |

TABLE 1-continued

Antibody sequences. Underlined, bold nucleotides or amino acids indicate the CDRs in the sequence of the variable domain. Italic nucleotides or amino acids indicate sequences which have not been sequenced but obtained from database.

| Antibody | Nucleotide and amino acid sequences of variable heavy (VH) and variable light (VL), constant heavy (CH) and constant light (CL) chains. | Seq. ID |
|---|---|---|
| DNA | ctcccaggctcctcatgtatggtgcatctaccagggccactgacatcccagacaggttcagtggc agtgggtctgggacagacttcactctcaccatcagcagactggagcctgaagattttgcagtgtatt actgtcagcagaatggtaactcaccatacacttttggccaggggaccaagctggagatcaaa | |
| 2F8 VL kappa-type amino acid | EIVLTQSPGTLSLSPGERATLSCRASQSVSNMFLVWYQQKPG QAPRLLMYGASTRATDIPDRFSGSGSGTDFTLTISRLEPEDFA VYYCQQNGNSPYTFGQGTKLEIK | 35 |
| 2F8 CH IgG1 subclass DNA | gcctccaccaagggcccatcggtcttccccctggcaccctcctccaagagcacctctgggggcac agcggccctgggctgcctggtcaaggactacttccccgaaccggtgacggtgtcgtggaactca ggcgccctgaccagcggcgtgcacaccttcccggctgtcctacagtcctcaggactctactccctc agcagcgtggtgaccgtgccctccagcagcttgggcacccagacctacatctgcaacgtgaatca caagcccagcaacaccaaggtggacaagagagttgagcccaaatcttgtgacaaaactcacaca tgcccaccgtgcccagcacctgaactcctggggggaccgtcagtcttcctcttccccccaaaaccc aaggacaccctcatgatctcccggacccctgaggtcacatgcgtggtggtggacgtgagccacg aagaccctgaggtcaagttcaactggtacgtggacggcgtggaggtgcataatgccaagacaaa gccgcgggaggagcagtacaacagcacgtaccgtgtggtcagcgtcctcaccgtcctgcaccag gactggctgaatggcaaggagtacaagtgcaaggtctccaacaaagccctcccagcccccatcg agaaaaccatctccaaagccaaagggcagccccgagaaccacaggtgtacaccctgcccccat cccgggaggagatgaccaagaaccaggtcagcctgacctgcctggtcaaaggcttctatcccag cgacatcgccgtggagtgggagagcaatgggcagccggagaacaactacaagaccacgcctc ccgtgctggactccgacggctccttcttcctctatagcaagctcaccgtggacaagagcaggtggc agcaggggaacgtcttctcatgctccgtgatgcatgaggctctgcacaaccactacacgcagaag agcctctccctgtccccgggtaaatga | 42 |
| 2F8 CH IgG1 subclass amino acid | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKRVEPKSCDKTHTCPPCPAPELLGGPSVFLFPPK PKDTLMISRTPEVTCVVVDVSHEDPEVKFNWYVDGVEVHNA KTKPREEQYNSTYRVVSVLTVLHQDWLNGKEYKCKVSNKAL PAPIEKTISKAKGQPREPQVYTLPPSREEMTKNQVSLTCLVKG FYPSDIAVEWESNGQPENNYKTTPPVLDSDGSFFLYSKLTVDK SRWQQGNVFSCSVMHEALHNHYTQKSLSLSPGK | 38 |
| 2F8 CL kappa-type DNA | cgaactgtggctgcaccatctgtcttcatcttcccgccatctgatgagcagttgaaatctggaactgc ctctgttgtgtgcctgctgaataacttctatcccagagaggccaaagtacagtggaaggtggataac gcccttccaatcgggtaactcccaggagagtgtcacagagcaggacagcaaggacagcacctac agcctcagcagcaccctgacggctgagcaaaagcagactacgagaaacacaaagtctacgcctgc gaagtcacccatcagggcctgagctcgcccgtcacaaagagcttcaacaggggagagtgttag | 41 |
| 2F8 CL kappa-type amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC | 37 |
| 7G6 VH DNA | caggtgcagctggtggagtctggggaggcgtggtgcagcctggggggtccctgagactctcat gtgcagcctctggcatcgccttcaatgactacactatgcactgggtccgccggtctccagacaag ggcctggagtgggtggcagctatatcatatggtgggactaataaatactacgcagattccgtg aagggccgattcaccatctccagagacagttccaagaacaccctgtttctgcagatggacagcct gagagttgaggacacggctgtgtattactgtgcgagagattctggttatcggagtcttttgcactg gggccaggggaaccctggtcaccgtctcctca | 54 |
| 7G6 VH amino acid | QVQLVESGGGVVQPGRSLRLSCAASGIAFNDYTMHWVRRSP DKGLEWVAAISYGGTNKYYADSVKGRFTISRDSSKNTLFLQ MDSLRVEDTAVYYCARDSGYRSLLHWGQGTLVTSS | 50 |
| 7G6 VL kappa-type DNA | gagattgtgttgactcagtctccactctccctgcccgtcacccctggtgagccggcctccatctcctg caggtcgagtcagagcctcgtgcatagaaatggatacaactatttagattggtacctgcagaa gccagggcagtctccacagctcctgatctatatggcttctaaacgggcctccggggtccctgaca ggttcagtggcagtgggtcaggcacagaattacactgaaaatcagcagagtggaggctgaggat gttggaatttattactgcatgcaagctctacaaacttggacgttcggccaagggaccaaggtgga agtcaac | 53 |
| 7G6 VL kappa-type amino acid | EIVLTQSPLSLPVTPGEPASISCRSSQSLVHRNGYNYLDWYLQ KPGQSPQLLIYMASKRASGVPDRFSGSGSGTEFTLKISRVEAE DVGIYYCMQALQTWTFGQGTKVEVN | 49 |
| 7G6 CH IgG4 subclass DNA | gcttccaccaagggcccatcggtcttccccctggcgccctgctccaggagcacctccgagagcac agccgccctgggctgcctggtcaaggactacttccccgaaccggtgacggtgtcgtggaactcag gcgccctgaccagcggcgtgcacaccttcccggctgtcctacagtcctcaggactctactccctca gcagcgtggtgaccgtgccctccagcagcttgggcacgaagacctacacctgcaacgtagatca caagcccagcaacaccaaggtggacaagagagttgagtccaaatatggtcccccatgcccatcat gcccagcacctgagttcctggggggaccatcagtcttcctgttccccccaaaacccaaggacact | 56 |

TABLE 1-continued

Antibody sequences. Underlined, bold nucleotides or amino acids indicate the CDRs in the sequence of the variable domain. Italic nucleotides or amino acids indicate sequences which have not been sequenced but obtained from database.

| Antibody | Nucleotide and amino acid sequences of variable heavy (VH) and variable light (VL), constant heavy (CH) and constant light (CL) chains. | Seq. ID |
|---|---|---|
| | ctcatgatctcccggaccccctgaggtcacgtgcgtggtggtggacgtgagccaggaagaccccg aggtccagttcaactggtacgtggatggcgtggaggtgcataatgccaagacaaagccgcggga ggagcagttcaacagcacgtaccgtgtggtcagcgtcctcaccgtcctgcaccaggactggctga acggcaaggagtacaagtgcaaggtctccaacaaaggcctcccgtcctccatcgagaaaaccat ctccaaagccaaagggcagccccgagagccacaggtgtacaccctgcccccatcccaggagga gatgaccaagaaccaggtcagcctgacctgcctggtcaaaggcttctaccccagcgacatcgcc gtggagtgggagagcaatgggcagccggagaacaactacaagaccacgcctcccgtgctggac tccgacggctccttcttcctctacagcaggctaaccgtggacaagagcaggtggcaggagggga atgtcttctcatgctccgtgatgcatgaggctctgcacaaccactacacacagaagagcctctccct gtctctgggtaaatga | |
| 7G6 CH IgG4 subclass amino acid | ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPSCPAPEFLGGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK | 52 |
| 7G6 CL kappa-type DNA | cgaactgtggctgcaccatctgtcttcatcttcccgccatctgatgagcagttgaaatctggaactgc ctctgttgtgtgcctgctgaataacttctatcccagagaggccaaagtacagtggaaggtggataac gcccctccaatcgggtaactcccaggagagtgtcacagagcaggacagcaaggacagcacctac agcctcagcagcaccctgacgctgagcaaagcagactacgagaaacacaaagtctacgcctgc gaagtcacccatcagggcctgagctcgcccgtcacaaagagctt*caacaggggagagtgttag* | 55 |
| 7G6 CL kappa-type amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKS*FNRGEC* | 51 |
| 4B2 VH DNA | *caggtgcagctgcaggaggcggggcccacgactggtgaagccttcacagaccctgtcagtcacc* tgcactgtctctggtgcctccatcaccattggcggttactactggagttggatccgccagcaccca gggaagggcctggaatggatggggtacatctattccaatgggaggacctactacaatccgtc cctcaagagtcgaattgccatgtcaatagacacgtctaaaaaccagttctccctgaagctgacttct gtgacagccgcggacacggccatatatttctgtgcgcgggaggcgtgggagacgccactgtgg ggccagggaaccctgatcaccgtctcctcc | 68 |
| 4B2 VH amino acid | *QVQLQEAGPRLVKPSQTLSVTCTVSGASIT*IGGYYWSWIRQHP GKGLEWMGYIYSNGRTYYNPSLKSRIAMSIDTSKNQFSLKLT SVTAADTAIYFCAREAWETPLWGQGTLITVSS | 64 |
| 4B2 VL kappa-type DNA | gacatccagatgactcagtctccatcctccctgtctgcttctgtaggagacagagtcaccatcacttg ccaggcgaatcaggacattgtcaactctttaaattggtttcaacacaaaccagggacagcccct aaagtcctgatctacgatgcatccaaattggaaacaggggtcccatctaggttcagtgaagtg gtctgggacacattttactttcaccataagtgcctgcagcctgaagattttgcaacatatttctgtca acaatatgagaatcttccgcacttttggccaggggaccaagttggagatcaga | 67 |
| 4B2 VL kappa-type amino acid | DIQMTQSPSSLSASVGDRVTITCQANQDIVNSLNWFQHKPGT APKVLIYDASKLETGVPSRFSGSGSTHFTFTISGLQPEDFATY FCQQYENLPHTFGQGTKLEIR | 63 |
| 4B2 CH IgG1 subclass DNA | gcctccaccaagggcccatcggtcttccccctggcaccctcctccaagagcacctctgggggcac agcggccctgggctgcctggtcaaggactacttccccgaaccggtgacggtgtcgtggaactca ggcgccctgaccagcggcgtgcacaccttcccggctgtcctacagtcctcaggactctactccctc agcagcgtggtgaccgtgccctccagcagcttgggcacccagacctacatctgcaacgtgaatca caagcccagcaacaccaaggtggacaagaaagttgagcccaaatcttgtgacaaaactcacacat gcccaccgtgcccagcacctgaactcctggggggaccgtcagtcttcctcttccccccaaaaccc aaggacaccct*catgatctcccggacccctgaggtcacatgcgtggtggtggacgtgagccac gaagaccctgaggtcaagttcaactggtacgtggacggcgtggaggtgcataatgccaagac aaagccgcgggaggagcagtacaacagcacgtaccgtgtggtcagcgtcctcaccgtcctgc accaggactggctgaatggcaaggagtacaagtgcaaggtctccaacaaagccctcccagc ccccatcgagaaaaccatctccaaagccaaagggcagccccgagaaccacaggtgtacac cctgcccccatcccgggatgagctgaccaagaaccaggtcagcctgacctgcctggtcaaag gcttctatcccagcgacatcgccgtggagtgggagagcaatgggcagccggagaacaacta caagaccacgcctcccgtgctggactccgacggctccttcttcctctacagcaagctcaccgtg gacaagagcaggtggcagcaggggaacgtcttctcatgctccgtgatgcatgaggctctgcac aaccactacacgcagaagagcctctccctgtctccgggtaaatga* | 70 |
| 4B2 CH IgG1 subclass amino acid | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPELLGGPSVFLFPPK PKDTL*MISRTPEVTCVVVDVSHEDPEVKFNWYVDGVEVHNAKTK* | 66 |

TABLE 1-continued

Antibody sequences. Underlined, bold nucleotides or amino acids indicate the CDRs in the sequence of the variable domain. Italic nucleotides or amino acids indicate sequences which have not been sequenced but obtained from database.

| Antibody | Nucleotide and amino acid sequences of variable heavy (VH) and variable light (VL), constant heavy (CH) and constant light (CL) chains. | Seq. ID |
|---|---|---|
| | *PREEQYNSTYRWSVLTVLHQDWLNGKEYKCKVSNKALPAPIEKTI SKAKGQPREPQVYTLPPSRDELTKNQVSLTCLVKGFYPSDIAVEW ESNGQPENNYKTTPPVLDSDGSFFLYSKLTVDKSRWQQGNVFSCS VMHEALHNHYTQKSLSLSPGK* | |
| 4B2 CL kappa-type DNA | cgaactgtggctgcaccatctgtcttcatcttcccgccatctgatgagcagttgaaatctggaactgc ctctgttgtgtgcctgctgaataacttctatcccagagaggccaaagtacagtggaaggtggataac gccctccaatcgggtaactcccaggagagtgtcacagagcaggacagcaaggacagcacctac agcctcagcagcaccctgacgctgagcaaagcagactacgagaaacacaaagtctacgcctgc gaagtcacccatcagggcctgagctcgcccgtcacaaagagcttcaacaggggagagtgttag | 69 |
| 4B2 CL kappa-type amino acid | RTVAAPSVFIFPPSDEQLKSGTASVVCLLNNFYPREAKVQWK VDNALQSGNSQESVTEQDSKDSTYSLSSTLTLSKADYEKHKV YACEVTHQGLSSPVTKSFNRGEC | 65 |
| 12G10 VH DNA | *gaggtgcagctgttggagt*ctgggggacgtttattacgccggggggtccctgagcctctcctg tgtagcctctggattctacttcggtgatttggcatgagctgggtccgccaggttccagggaaggg gctggagtgggtctctggcattgactggagtggccgtagtacaggttatgtagactccatgaa gggccgactccaccatctccagagacaacgacaagagttccctgtatttgcaaatgaacgatctgcg cggcgaggacacggccgtctattactgtgcgagggtcgggagactctgtagtggtgattcttgc gactcaatgggcgcttttgacctgtggggccaggggacaatggtcaccgtctcttca | 80 |
| 12G10 VH amino acid | *EVQLLESGGRLLRPGGSLSLSCVASGFYFG*DFGMSWVRQVPG KGLEWVSGIDWSGRSTGYVDSMKGRLTISRDNDKSSLYLQ MNDLRGEDTAVYYCARVGRLCSGDSCDSMGAFDLWGQGT MVTVSS | 78 |
| 12G10 VL kappa-type DNA | *gacatccagttgacccagtctccttccaccctgtctgcatctataggagacagcgtcaccatcactt* gccgggccagtcagaatattgataactggttggcctggtatcaacagaaaccagggaaagccc ctagactcctgatctacaaggcgtctagtctaggaagtggggtctcatcaaagttcagaggcagt ggatttgggacagagttcactctcaccatcaccagcctgcagcctgatgactttgcaacctattattg tcagaagtctaatggctattctcgtacttttggccaggggaccaaagtggatatcaaa | 79 |
| 12G10 VL kappa-type amino acid | *DIQLTQSPSTLSASIGDSVTITC*RASQNIDNWLAWYQQKPGKA PRLLIYKASSLGSGVSSKFRGSGFGTEFTLTITSLQPDDFATYY CQKSNGYSRTFGQGT*KVDIK* | 77 |

Antibody Production and Purification

Recombinant monoclonal human antibodies are expressed upon transfection of antibody-coding expression vectors into HEK293T or Chinese Hamster Ovary cells by the Polyethylenimine transfection method (PEI, Polyscience Warrington, USA). After transfection, cells are cultured in reduced serum medium (OptiMEM® I supplemented with GlutaMAX[198]-I, Gibco) for 3-6 days. Subsequently, supernatants are collected and IgG-antibodies are purified using protein A columns (GE HealthCare, Sweden) on a fast protein liquid chromatography device (FPLC) (ÄKTA, GE HealthCare, Sweden).

Example 1: Detection of Peanut-Specific Antibodies by ELISA Assay

Enzyme linked immunosorbent assay (ELISA) was used to evaluate allergen reactivity in the sera of allergic patients. Allergens (Ara h 2, Ara h 1, Ara h 3, Ara h 6, peanut extract) were coated on plates and anti-peanut antibody levels in sera from allergic patients were detected using HRP-conjugated anti-human antibody. Altogether, sera from 84 allergic patients, were used in the assays. The following protocol describes the experimental procedures for the detection of anti-allergen antibodies by ELISA assay. Allergic patients have shown seroreactivity against several Ara h peanut allergens, implicating the suitability of these antibodies against allergic response induced by several peanut allergens.

ELISA for the Detection of Peanut-Specific Antibodies 96 well microplates (Costar®, Corning Incorporated, Corning, NY, USA) were coated with peanut allergens either extracted and purified from peanuts or recombinantly expressed. Major peanut allergens included in the example are Ara h 1, Ara h 2, Ara h 3 and Ara h 6 (Indoor Biotechnologies, Cardiff, UK). Plates were washed with PBS-Tween 0.05% and blocked 1 h at room temperature with PBS containing 5% Milk (Rapilait, Migros, Zurich, Switzerland) or 2% bovine serum albumin (BSA, Sigma-Aldrich Chemie GmbH, Buchs, Switzerland).

Patient sera, B cell conditioned medium, or recombinant antibody preparations were incubated for 2 h at room temperature. Binding of human IgG4, IgE or total IgG to the antigen of interest was determined using a HRP-conjugated anti human antibody (anti-IgG-HRP from Jackson ImmunoResearch, West Grove, Pa., USA; anti-IgE-HRP from Abcam, Cambridge, UK anti-IgG4-HRP from ThermoFisher Scientific, Carlsbad, CA, USA) followed by measurement of the HRP activity using a tetramethylbenzidine substrate solution (TMB, Sigma-Aldrich Chemie GmbH, Buchs, Switzerland). For the results see FIG. 1-2.

Example 2: EC50 ELISA Determination of the Antibodies of the Present Invention

EC50 binding of exemplary anti-peanut antibodies of the present invention to peanut allergens or peanut extract, was determined by ELISA. Serial dilutions of MAbs (from 1000 ng/ml down to 0.0169 ng/ml) were incubated for 2 hours with antigen-coated plates (coating overnight at 4° C. or 1 h at 37° C. with 1 µg/ml antigen in PBS, followed by wash out and blocking with 2% BSA in PBS). The plates were subsequently washed and binding of MAbs was detected with anti-human HRP-conjugated Fc-gamma-specific secondary antibody (Jackson ImmunoResearch, West Grove, PA, USA). Concentrations of MAb resulting in half of maximal binding to respective antigens (EC50, ng/ml) were calculated using GraphPad Prism 5 software on sigmoidal dose-response curves (variable slope, 4 parameters) obtained by plotting the log of the concentration versus OD450 nm measurements; for the results see FIG. 3 and table 2.

TABLE 2

EC50 ELISA determination of binding of exemplary human anti-peanut allergen antibodies and murinized versions of the antibodies depicted in FIG. 3. n.b. = not binding, n.p. = experiment not performed.

| EC50 [ng/ml], MY006 antibodies [ng/ml], | peanut allergens | | | | | | | other allergens | | |
|---|---|---|---|---|---|---|---|---|---|---|
| | nArah2 | peanut extract | nArah1 | nArah3 | nArah6 | rArah8 | rArah9 | nBetv1 | rAnao3 | nCora9 |
| h12G10 | 6.8 | 8.1 | 242.2 | 33.7 | 17.2 | n.b. | n.b. | n.b. | n.b. | n.b. |
| hm12G10 | 6.7 | 8.5 | 194.7 | 36.8 | 27.8 | n.p. | n.p. | n.p. | n.p. | n.p. |
| h37D5 | 5.6 | 6.5 | 263.8 | 65.2 | 22.1 | n.b. | n.b. | n.b. | n.b. | n.b. |
| hm37D5 | 5.2 | 7.1 | 115.1 | 72.3 | 34.0 | n.p. | n.p. | n.p. | n.p. | n.p. |
| h32B10 | 9.2 | 4.8 | 8.8 | 4.9 | 7.0 | n.b. | n.b. | n.b. | n.b. | n.b. |
| hm32B10 | 9.9 | n.p. | n.p. | n.p. | n.p. | n.p. | n.p. | n.p. | n.p. | n.p. |
| h2F8 | 5.6. | 2.8 | 8.5 | 2.8 | 3.4 | n.b. | n.b. | n.b. | n.b. | n.b. |
| hm2F8 | 8.7 | n.p. | n.p. | n.p. | n.p. | n.p. | n.p. | n.p. | n.p. | n.p. |
| h7G6 | 4.7 | 2.8 | 1.9 | 1.3 | 2.6 | n.b. | n.b. | n.b. | n.b. | n.b. |
| hm7G6 | n.p. | n.p. | n.p. | n.p. | n.p. | n.p. | n.p. | n.p. | n.p. | n.p. |
| h4B2 | 6.7 | n.p. | 5.9 | n.p. | 7.0 | n.b. | n.b. | n.b. | n.b. | n.b. |
| hm4B2 | 10.2 | n.p. | n.p. | n.p. | n.p. | n.p. | n.p. | n.p. | n.p. | n.p. |

Example 3: Cross-Competition With Human-Mouse Chimeric Constructs of Anti-Peanut Antibodies As first step of mapping, differential binding of anti-peanut MAbs of the present invention to distinct antigen binding sites was examined to determine the number of different binding sites.

For this purpose, MAbs were expressed either with human (hMAb) or mouse (hmMab) Fc and cross-competition experiments were carried out by coating antigen on plates and by detecting binding of human Mabs in the presence of titrated amount of hmMabs. Detection of hMAbs bound to the ligand was performed by a HRP conjugated secondary antibody directed against the Fc portion of the primary antibody (Jackson ImmunoResearch, West Grove, PA, USA).

As may be seen from Table 3, exemplary anti-peanut allergens antibodies 37D5 and 12G10 of the present invention compete each other for binding of Ara h 2 but not with antibodies 4B2 and 32B10, indicating that 12G10 and 37D5 bind other sites of Ara h 2 than 4B2 and 32B10.

TABLE 3

The differential binding of exemplary human monoclonal antibodies (hMAbs) of the present invention with the respective MAbs with mouse Fc (hmMAbs) to distinct binding sites was investigated in cross-competition experiments with titrated hmMAbs (0-12'000 ng/ml) and anti-human IgG horseradish peroxidase (HRP)-conjugated detection antibody.

| | 37D5 | 32B10 | 12G10 | 4B2 |
|---|---|---|---|---|
| 37D5 | competing | n.c. | competing | n.c. |
| 32B10 | n.c. | competing | n.c. | n.c. |
| 12G10 | competing | n.c. | competing | n.c. |
| 4B2 | n.c. | n.c. | n.c. | competing |

"n.c.": non-competing antibodies; "competing": competing antibodies.

Example 4: ELISA Inhibition Assay of Allergic Patient IgE Binding to Allergen

Microplates were coated with 0.05m/ml of Ara h 1, Ara h 2, Ara h 3, or Ara h 6, overnight at 4° C. After washing with PBS-Tween 0.05% and blocking with 2% BSA, plates were incubated with increasing concentrations of peanut human IgG antibodies for 1 h at room temperature. Subsequently, plates were incubated with different sera dilutions or different concentrations of murine antibody (as positive control). IgE levels were detected using anti-human HRP-conjugated Fc-epsilon-specific secondary antibody (Abcam, Cambridge, UK) followed by addition of TMB solution (TMB, Sigma, Buchs, Switzerland). Binding of murine antibodies was detected using goat anti-mouse IgG (H+L)-HRP (Jackson ImmunoResearch, West Grove, PA, USA). Results are shown in table 4.

TABLE 4

ELISA competition assay shows inhibition of allergic patient IgE binding to allergen (Ara h 2). 37D5 and 12G10 antibody blocked the binding of allergic patients' polyclonal IgE to Ara h 2 up to 60%. Antibody cocktail containing 32B10, 37D5, 4B2 and 12G10 blocked up to 80% of polyclonal IgE from allergic patients.

|  | 32B10 | 12G10 | 37D5 | 4B2 | cocktail |
|---|---|---|---|---|---|
| Patient A | 27.76 ± 4.85 | 13.82 ± 5.31 | 27.77 ± 3.58 | 39.66 ± 5.95 | 66.21 ± 0.6 |
| Patient B | 26.66 ± 1.63 | 31.16 ± 5.92 | 29.61 ± 1.33 | 30.65 ± 2.48 | 58.75 ± 1.49 |
| Patient C | 21.00 ± 5.17 | 53.81 ± 3.35 | 55.08.42 ± 1.98 | 13.34 ± 5.71 | 64.62 ± 3.41 |
| Patient D | 8.50 ± 7.06 | 35.74 ± 7.96 | 35.51 ± 4.53 | 9.23 ± 3.17 | 71.02 ± 1.48 |
| Patient E | 29.32 ± 2.03 | 36.24 ± 3.25 | 29.30 ± 3.05 | 21.91 ± 5.23 | 73.18 ± 5.29 |
| Patient F | 23.15 ± 4.81 | 45.34 ± 3.10 | 36.25 ± 3.27 | 30.77 ± 0.73 | 75.06 ± 6.91 |
| Patient G | 32.83 ± 6.33 | 25.74 ± 7.00 | 45.32 ± 17.11 | 31.77 ± 2.00 | 80.15 ± 5.73 |
| Healthy donor | 0.00 | 0.00 | 2.27 ± 64.04 | 0.00 | 0.00 |

Example 5: Basophil Activation Test. Human-Derived Anti-Peanut Monoclonal Antibodies Neutralize Natural Ara h 2 and Peanut Extract Mediated Basophil Activation Basophil activation test was performed using whole blood from allergic patients, sampled in Heparin tubes (S-Monovette® 02.1065, Sarstedt, Nümbrecht, Germany). To test the neutralizing capacity of antibodies, the optimal concentration of Ara h 2 or peanut extract was preincubated with one or serial dilutions of serum, supernatant or purified antibody samples (one or a combination of them). Afterwards, 100 µl of whole blood were stimulated with either natural Ara h 2 (10 ng/ml, Indoor Biotechnologies, Cardiff, UK) or peanut extract (10 ng/ml, Indoor Biotechnologies, Cardiff, UK) or stimulation buffer (negative control) in the presence/absence of different anti-peanut allergen antibodies or the combination thereof (MY006 cocktail) or isotype control for 30 minutes at 37° C., 5% CO2. Cells were stained simultaneously with anti-CCR3-APC, anti-CD203c-PE and anti-CD63-FITC (Biolegend, San Diego, CA, USA). Basophils were gated as SSClow, CCR3high lymphocytes. At least 500 basophils were acquired using FACSCalibur (Becton Dickinson AG, Allschwil, Switzerland). Activation of basophils was quantified using % of CD63+ CCR3+ basophils and/or median fluorescence intensity of CD203c CCR3+basophils. Data was analyzed using FlowJo Software (FlowJo, Ashland, OR, USA). Results are shown in FIG. 4.

Example 6: Epitope Mapping of Exemplary Peanut-Specific Antibodies

A competition ELISA was used to evaluate binding of exemplary anti-peanut antibodies of the present invention to linear Ara h 2 epitopes. Serial dilutions of linear Ara h 2 epitopes (100 µM down to 0.19 nM; peptides with a length of 20 amino acids and an overlap of 12 amino acids between the peptides) were pre-incubated with exemplary anti-peanut antibodies (66 pM) for 1 hour at room temperature. The pre-incubated antibody-epitope mixtures were subsequently incubated on plates coated with full length Ara h 2 (coating overnight at 4° C. with 0.05 µg/ml Ara h 2 in PBS, followed by wash out and blocking with 2% BSA in PBS). The plates were subsequently washed and binding of MAbs to Ara h 2 was detected HRP-conjugated goat anti human Fc-gamma-specific antibody (Jackson ImmunoResearch, West Grove, PA, USA) followed by measurement of the HRP activity using a tetramethylbenzidine substrate solution (TMB, Sigma-Aldrich Chemie GmbH, Buchs, Switzerland). As may be seen from Table 5, exemplary anti-peanut allergen antibody 32B10 binds to different linear Ara h 2 epitopes than 12G10 and 37D5. 4B2,7G6 and 2F8 do not bind to any of the 20 linear epitopes suggesting binding to conformational epitopes.

TABLE 5

Epitope binding of exemplary human monoclonal antibodies of the present invention was evaluated in a competition ELISA with serial dilutions of linear Ara h 2 peptides (100 µM down to 0.19 nM). Antibodies 12G10 and 37D5 are binding peptides 8-11, antibody 32B10 binds to peptide 4. Antibodies 4B2, 7G6 and 2F8 do not bind any of the linear Ara h 2 peptides, "n.b.": not binding to peptide; "Binding": binding to peptide.

| SEQ ID | | Sequence/description of pool | 32B10 | 37D5 | 12G10 | 4B2 | 7G6 | 2F8 |
|---|---|---|---|---|---|---|---|---|
|  | POOL 1 | Combination of peptides 1 to 5 | Binding | n.b. | n.b. | n.b | n.b. | n.b. |
| 81 | Peptide 1 | $^{1}$AMALKLTILVALALFLLAAH$^{20}$ | n.b. | n.b. | n.b. | n.b | n.b. | n.b. |
| 82 | Peptide 2 | $^{9}$ALALFLLAAHASARQQWELQ$^{28}$ | n.b. | n.b. | n.b. | n.b | n.b. | n.b. |

TABLE 5-continued

Epitope binding of exemplary human monoclonal antibodies of the present invention was evaluated in a competition ELISA with serial dilutions of linear Ara h 2 peptides (100 μM down to 0.19 nM). Antibodies 12G10 and 37D5 are binding peptides 8-11, antibody 32B10 binds to peptide 4. Antibodies 4B2, 7G6 and 2F8 do not bind any of the linear Ara h 2 peptides, "n.b.": not binding to peptide; "Binding": binding to peptide.

| SEQ ID | | Sequence/description of pool | 32B10 | 37D5 | 12G10 | 4B2 | 7G6 | 2F8 |
|---|---|---|---|---|---|---|---|---|
| 83 | Peptide 3 | $^{17}$AHASARQQWELQGDRRCQSQ$^{36}$ | n.b. | n.b. | n.b. | n.b | n.b. | n.b. |
| 84 | Peptide 4 | $^{25}$WELQGDRRCQSQLERANLRP$^{44}$ | Binding | n.b. | n.b. | n.b | n.b. | n.b. |
| 85 | Peptide 5 | $^{33}$CQSQLERANLRPCEQHLMQK$^{52}$ | n.b. | n.b. | n.b. | n.b | n.b. | n.b. |
| | POOL 2 | Combination of peptides 6 to 10 | n.b. | Binding | Binding | n.b | n.b. | n.b. |
| 86 | Peptide 6 | $^{41}$NLRPCEQHLMQKIQRDEDSY$^{60}$ | n.b. | n.b. | n.b | n.b | n.b. | n.b. |
| 87 | Peptide 7 | $^{49}$LMQKIQRDEDSYGRDPYSPS$^{68}$ | n.b. | n.b. | n.b | n.b | n.b. | n.b. |
| 88 | Peptide 8 | $^{57}$EDSYGRDPYSPSQDPYSPSQ$^{76}$ | n.b. | Binding | Binding | n.b | n.b. | n.b. |
| 89 | Peptide 9 | $^{65}$YSPSQDPYSPSQDPDRRDPY$^{84}$ | n.b. | Binding | Binding | n.b | n.b. | n.b. |
| 90 | Peptide 10 | $^{73}$SPSQDPDRRDPYSPSPYDRR$^{92}$ | n.b. | Binding | Binding | n.b | n.b. | n.b. |
| | POOL 3 | Combination of peptides 11 to 15 | n.b. | Binding | Binding | n.b | n.b. | n.b. |
| 91 | Peptide 11 | $^{81}$RDPYSPSPYDRRGAGSSQHQ$^{100}$ | n.b. | Binding | Binding | n.b | n.b. | n.b. |
| 92 | Peptide 12 | $^{89}$YDRRGAGSSQHQERCCNELN$^{108}$ | n.b. | n.b. | n.b | n.b | n.b. | n.b. |
| 93 | Peptide 13 | $^{97}$SQHQERCCNELNEFENNQRC$^{116}$ | n.b. | n.b. | n.b | n.b | n.b. | n.b. |
| 94 | Peptide 14 | $^{105}$NELNEFENNQRCMCEALQQI$^{124}$ | n.b. | n.b. | n.b | n.b | n.b. | n.b. |
| 95 | Peptide 15 | $^{113}$NQRCMCEALQQIMENQSDRL$^{132}$ | n.b. | n.b. | n.b | n.b | n.b. | n.b. |
| | POOL 4 | Combination of peptides 16 to 20 | n.b. | n.b. | n.b | n.b | n.b. | n.b. |
| 96 | Peptide 16 | $^{121}$LQQIMENQSDRLQGRQQEQQ$^{140}$ | n.b. | n.b. | n.b | n.b | n.b. | n.b. |
| 97 | Peptide 17 | $^{129}$SDRLQGRQQEQQFKRELRNL$^{180}$ | n.b. | n.b. | n.b | n.b | n.b. | n.b. |
| 98 | Peptide 18 | $^{137}$RQQEQQFKRELRNLPQQCGLRA$^{156}$ | n.b. | n.b. | n.b | n.b | n.b. | n.b. |
| 99 | Peptide 19 | $^{145}$LRNLPQQCGLRAPQRCDLEV$^{164}$ | n.b. | n.b. | n.b | n.b | n.b. | n.b. |
| 100 | Peptide 20 | $^{153}$GLRAPQRCDLEVESGGRDRY$^{172}$ | n.b. | n.b. | n.b | n.b | n.b. | n.b. |

Example 7: Validation of Peanut Antibodies in Animals

Mice C3H/HeJ, BALB/c, C57BL/6 and/or AKR/J are sensitized by intragastric (i.g.) or intraperitoneal (i.p.) administration of peanut (e.g. ground whole peanut, crude peanut extracts or whole peanut extracts) and adjuvant (e.g. cholera toxin, alum) on a weekly basis for up to 12 weeks. Control mice receive PBS with selected adjuvant. After 2-3 months of sensitization, mice are challenged by i.g. or i.p. administration of peanut (e.g. ground whole peanut, crude peanut extracts or whole peanut extracts). Treatment consists of i.p. or intravenous (i.v.) administration of different antibody doses prior challenge.

At several time points during the course of the model, blood is taken for the measurement of antibodies (total and peanut specific IgE and IgG antibodies), mMCP-1 (mast cell protease 1), histamine and leukotriene levels.

Anaphylactic symptoms are evaluated 30 minutes after the challenge dose utilizing a defined scoring system (see table below). Scoring of symptoms is performed in a blinded manner by two independent investigators. After euthanization, ear, spleen and blood samples are collected. Blood samples are analyzed as described above. Histological sections are prepared and stained with toluidine blue or Giemsa stain. Degranulated mast cells are toluidine blue- or Giemsa positive with 5 or more stained granules completely outside the cell. 400 mast cells are classified.

Anaphylaxis Scoring System (Ref Liu et al. 2016 Review or Original Papers):

| Score | Anaphylactic symptoms |
|---|---|
| 0 | no symptoms |
| 1 | scratching and rubbing around the nose and head |
| 2 | puffiness around the eyes and mouth, pilar erecti (erection of the hair of the skin), reduced activity and/or decreased activity with increased respiratory rate |
| 3 | wheezing, labored respiration, and cyanosis around the mouth and tail |
| 4 | slight or no activity after prodding, or tremor and convulsion |
| 5 | death |

Antibody effects are evaluated by comparing clinical reactions in antibody treated and control animals using the anaphylaxis scoring system (illustrated in the table above). Therapeutic efficacy of anti-peanut antibodies disclosed herein is indicated by a reduction or absence of anaphylactic symptoms in antibody treated animals compared to control animals.

Alternatively or in addition, antibody effects are evaluated by comparing serum peanut specific IgE antibodies, mMCP-1 levels and/or plasma histamine and leukotriene levels in antibody treated and control animals using ELISA-based assays. Therapeutic efficacy of anti-peanut antibodies disclosed herein is indicated by a reduction or absence of serum peanut-specific IgE antibodies and/or plasma histamine in antibody treated animals relative to control animals.

Alternatively or in addition, antibody effects are evaluated by comparing cytokine expression levels in challenged splenocytes derived from antibody treated and control animals.

Example 8: Leukotriene Release Assay

Leukotriene release assay was performed using whole blood from allergic patients, sampled in Heparin tubes (S-Monovette® 02.1065, Sarstedt, Nümbrecht, Germany).

Leukocytes were isolated by dextran sedimentation. To test the neutralizing capacity of antibodies, titrations of peanut extract (0-30 ng/ml) were preincubated with purified antibody samples (one or a combination of them, 1.2 µg/ml) for 1 h at room temperature. Afterwards, leukocytes were stimulated with titrated peanut extract (Indoor Biotechnologies, Cardiff, UK) or stimulation buffer (negative control) in the presence/absence of different anti-peanut allergen antibodies or the combination thereof (MY006 cocktail) or isotype control for 40 minutes at 37° C., 5% CO2. Supernatant was collected and activation of basophils was quantified using CAST®ELISA (Bühlmann, Schönenbuch, Switzerland). See FIG. 5 showing that human-derived anti-peanut monoclonal antibodies neutralize peanut extract mediated basophil activation.

Example 9: Passive Sensitization Leukotriene Release Assay

Passive sensitization leukotriene release assay was performed using whole blood from healthy donors, sampled in Heparin tubes. Leukocytes were isolated by dextran sedimentation. Surface IgE was removed by stripping with lactic acid, pH 3.9 (8 minutes 4° C.). Leukocytes were re-sensitized by incubation with plasma from allergic patients (1 h at 37° C.). To test the neutralizing capacity of antibodies, titrations of peanut extract (0-30 ng/ml) were preincubated with purified antibody samples (one or a combination of them, 1.2 µg/ml). Afterwards, re-sensitized leukocytes were stimulated with titrated peanut extract (Indoor Biotechnologies, Cardiff, UK) or stimulation buffer (negative control) in the presence/absence of different anti-peanut allergen antibodies or the combination thereof (MY006 cocktail) or isotype control for 40 minutes at 37° C., 5% CO2. Supernatant was collected and activation of basophils was quantified using CAST®ELISA (Bühlmann, Schönenbuch, Switzerland). See FIG. 6 showing that human-derived monoclonal antibodies decrase peanut extract mediated basophil activation.

The application further contains the following embodiments:

Embodiment 1. Antibody or binding fragment thereof capable of binding to a food allergen.

Embodiment 2. Antibody or binding fragment thereof according to embodiment 1, wherein the antibody is human-derived.

Embodiment 3. Antibody or binding fragment thereof according to embodiment 1 or 2, wherein the food allergen is a peanut allergen.

Embodiment 4. Antibody or binding fragment thereof according to embodiment 3, wherein the peanut allergen is selected from the group consisting of Ara h 1, Ara h 2, Ara h 3, Ara h 4, Ara h 5, Ara h 6/7, Ara h 8, Ara h 9 and Ara h 10/11.

Embodiment 5. Antibody or binding fragment thereof according to embodiment 4, wherein the peanut allergen is selected from the group consisting of Ara h 1, Ara h 2, Ara h 3 and Ara h 6, or a combination thereof.

Embodiment 6. Antibody or binding fragment thereof according to any one of embodiments 1 to 5, wherein the antibody is capable of binding at least one of the Ara h2 epitopes selected from the group consisting of the amino acid sequences set forth in SEQ ID NOs: 84, 88, 89, 90 and 91.

Embodiment 7. Antibody or binding fragment thereof according to any one of embodiments 3 to 5, wherein the peanut allergen is of peanut origin, recombinantly expressed or is a synthetic peanut peptide.

Embodiment 8. Antibody or binding fragment thereof according to any one of the preceding embodiments, wherein the antibody is a monoclonal antibody and/or wherein the antibody is a recombinant antibody.

Embodiment 9. Antibody or binding fragment thereof according to any one of the preceding embodiments, wherein the antibody is an IgG or IgA antibody.

Embodiment 10. Antibody or binding fragment thereof according to any one of the preceding embodiments, wherein the variable regions, portions thereof or the CDRs are human-derived.

Embodiment 11. Antibody or binding fragment thereof according to any one of the preceding embodiments, wherein the variable regions, portions thereof or the CDRs are derived from an IgE antibody and grafted in a scaffold of an IgG or IgA antibody.

Embodiment 12. Antibody or binding fragment thereof according to any one of the preceding embodiments, wherein the peptide sequence of the antibody or binding fragment thereof is identical or at least 60% identical to the sequence of the antibody extracted from the human.

Embodiment 13. Antibody or binding fragment thereof according to any one of embodiment 2 to 12, wherein the human is selected from the group of a human suffering from peanut allergy, a peanut-sensitized human without clinical relevant allergy, a human suffering from peanut allergy that underwent immunotherapy, a human that has outgrown peanut allergy and a human of unknown clinical history for peanut allergy.

Embodiment 14. Antibody or binding fragment thereof according to any one of the preceding embodiments, wherein the antibody has an EC50 of at most 270 ng/ml, preferably at most 70 ng/ml, at most 40 ng/ml, at most 25 ng/ml, at most 15 ng/ml, at most 4.9 ng/ml, at most 1.3 ng/ml for at least one of the peanuts allergens selected from the group consisting of Ara h 2, Ara h 1, Ara h 3 and Ara h 6.

Embodiment 15. Antibody or binding fragment thereof according to any one of the preceding embodiments, wherein the antibody has an EC50 of at most 10 ng/ml, preferably at most 7 ng/ml, more preferably at most 4.8 ng/ml, most preferably 2.8 ng/ml for peanut extract.

Embodiment 16. Antibody or binding fragment thereof according to any one of the preceding embodiments, wherein the antibody is capable of reducing, inhibiting or neutralizing allergen-mediated biological activity.

Embodiment 17. Antibody or binding fragment thereof according to any one of the preceding embodiments, wherein the antibody is capable of reducing or inhibiting the binding of an IgE antibody to the food allergen.

Embodiment 18. Antibody or binding fragment thereof according to any of the preceding embodiments, comprising a light chain variable region and/or a heavy chain variable region, wherein the light chain variable region comprises a CDR1 set forth in SEQ ID No: 1 or sequences at least 65% identical thereto, a CDR2 set forth in SEQ ID No: 2 or sequences at least 65% identical thereto, a CDR3 set forth in SEQ ID No: 3 or sequences at least 65% identical thereto; wherein the heavy chain variable region comprises a CDR1 set forth in SEQ ID No: 4 or sequences at least 65% identical thereto, a CDR2 set forth in SEQ ID No: 5 or sequences at least 65% identical thereto, and a CDR3 set forth in SEQ ID No: 6 or sequences at least 65% identical thereto.

Embodiment 19. Antibody or binding fragment thereof according to any one of embodiments 1 to 17, comprising a light chain variable region and/or a heavy chain variable region, wherein the light chain variable region comprises a CDR1 set forth in SEQ ID No: 15 or sequences at least 65% identical thereto, a CDR2 set forth in SEQ ID No: 16 or sequences at least 65% identical thereto, a CDR3 set forth in SEQ ID No: 17 or sequences at least 65% identical thereto; wherein the heavy chain variable region comprises a CDR1 set forth in SEQ ID No: 18 or sequences at least 65% identical thereto, a CDR2 set forth in SEQ ID No: 19 or sequences at least 65% identical thereto, a CDR3 set forth in SEQ ID No: 20 or sequences at least 65% identical thereto.

Embodiment 20. Antibody or binding fragment thereof according to any one of embodiments 1 to 17, comprising a light chain variable region and/or a heavy chain variable region, wherein the light chain variable region comprises a CDR1 set forth in SEQ ID No: 29 or sequences at least 65% identical thereto, a CDR2 set forth in SEQ ID No: 30 or sequences at least 65% identical thereto, a CDR3 set forth in SEQ ID No: 31 or sequences at least 65% identical thereto; wherein the heavy chain variable region comprises a CDR1 set forth in SEQ ID No: 32 or sequences at least 65% identical thereto, a CDR2 set forth in SEQ ID No: 33 or sequences at least 65% identical thereto, a CDR3 set forth in SEQ ID No: 34 or sequences at least 65% identical thereto.

Embodiment 21. Antibody or binding fragment thereof according to any one of embodiments 1 to 17, comprising a light chain variable region and/or a heavy chain variable region, wherein the light chain variable region comprises a CDR1 set forth in SEQ ID No: 43 or sequences at least 65% identical thereto, a CDR2 set forth in SEQ ID No: 44 or sequences at least 65% identical thereto, a CDR3 set forth in SEQ ID No: 45 or sequences at least 65% identical thereto; and/or wherein the heavy chain variable region comprises a CDR1 set forth in SEQ ID No: 46 or sequences at least 65% identical thereto, a CDR2 set forth in SEQ ID No: 47 or sequences at least 65% identical thereto, a CDR3 set forth in SEQ ID No: 48 or sequences at least 65% identical thereto.

Embodiment 22. Antibody or binding fragment thereof according to any one of embodiments 1 to 17, comprising a light chain variable region and/or a heavy chain variable region, wherein the light chain variable region comprises a CDR1 set forth in SEQ ID No: 57 or sequences at least 65% identical thereto, a CDR2 set forth in SEQ ID No: 58 or sequences at least 65% identical thereto, a CDR3 set forth in SEQ ID No: 59 or sequences at least 65% identical thereto; and/or wherein the heavy chain variable region comprises a CDR1 set forth in SEQ ID No: 60 or sequences at least 65% identical thereto, a CDR2 set forth in SEQ ID No: 61 or sequences at least 65% identical thereto, a CDR3 set forth in SEQ ID No: 62 or sequences at least 65% identical thereto.

Embodiment 23. Antibody or binding fragment thereof according to any one of embodiments 1 to 17, comprising a light chain variable region and/or a heavy chain variable region, wherein the light chain variable region comprises a CDR1 set forth in SEQ ID No: 71 or sequences at least 65% identical thereto, a CDR2 set forth in SEQ ID No: 72 or sequences at least 65% identical thereto, a CDR3 set forth in SEQ ID No: 73 or sequences at least 65% identical thereto; and/or wherein the heavy chain variable region comprises a CDR1 set forth in SEQ ID No: 74 or sequences at least 65% identical thereto, a CDR2 set forth in SEQ ID No: 75 or sequences at least 65% identical thereto, a CDR3 set forth in SEQ ID No: 76 or sequences at least 65% identical thereto.

Embodiment 24. Antibody or binding fragment thereof according to any one of embodiments 1 to 17, comprising a light chain variable region and/or a heavy chain variable region, wherein the light chain variable region comprises a CDR1 set forth in SEQ ID No: 1 or sequences at least 91% identical thereto, a CDR2 set forth in SEQ ID No: 2 or sequences at least 71% identical thereto, a CDR3 set forth in SEQ ID No: 3; wherein the heavy chain variable region comprises a CDR1 set forth in SEQ ID No: 4 or sequences at least 80% identical thereto, a CDR2 set forth in SEQ ID No: 5 or sequences at least 82% identical thereto, a CDR3 set forth in SEQ ID No: 6 or a sequence at least 94% identical thereto.

Embodiment 25. Antibody or binding fragment thereof according to any one of embodiments 1 to 17, comprising a light chain variable region and/or a heavy chain variable region, wherein the light chain variable region comprises a CDR1 set forth in SEQ ID No: 71 or sequences at least 91% identical thereto, a CDR2 set forth in SEQ ID No: 72 or sequences at least 71% identical thereto, a CDR3 set forth in SEQ ID No: 73; wherein the heavy chain variable region comprises a CDR1 set forth in SEQ ID No: 74 or sequences at least 80% identical thereto, a CDR2 set forth in SEQ ID No: 75 or sequences at least 82% identical thereto, a CDR3 set forth in SEQ ID No: 76 or sequences at least 94% identical thereto.

Embodiment 26. Antibody or binding fragment thereof according to any one of the preceding embodiments, comprising a $C_L$ and/or $C_H$ constant region comprising an amino acid sequence selected from the $C_L$ amino acid sequences SEQ ID NOS: 9, 23, 37, 51 and 65 or an amino acid sequence with at least 60% identity and an amino acid sequence selected from the $C_H$ amino acid sequences SEQ ID NOS: 10, 24, 38, 52 and 66 or an amino acid sequence with at least 60% identity.

Embodiment 27. Antibody or binding fragment thereof according to any one of the preceding embodiments, wherein the antibody is selected from the group consisting of a full length antibody, a multispecific antibody, a single chain Fv fragment (scFv), a F(ab') fragment, a F(ab')2 fragment, a F(ab)c fragment, a single domain antibody fragment (sdAB) and a multispecific antibody fragment.

Embodiment 28. Antibody or binding fragment thereof comprising a light chain variable region and/or a heavy chain variable region, wherein the light chain variable region comprises a CDR1 set forth in SEQ ID No: 1 or sequences at least 65% identical thereto, a CDR2 set forth in SEQ ID No: 2 or sequences at least 65% identical thereto, a CDR3 set forth in SEQ ID No: 3 or sequences at least 65% identical thereto; wherein the heavy chain variable region comprises a CDR1 set forth in SEQ ID No: 4 or sequences at least 65% identical thereto, a CDR2 set forth in SEQ ID No: 5 or sequences at least 65% identical thereto, and a CDR3 set forth in SEQ ID No: 6 or sequences at least 65% identical thereto.

Embodiment 29. Antibody comprising a light chain variable region and/or a heavy chain variable region, wherein the light chain variable region comprises a CDR1 set forth in SEQ ID No: 15 or sequences at least 65% identical thereto, a CDR2 set forth in SEQ ID No: 16 or sequences at least 65% identical thereto, a CDR3 set forth in SEQ ID No: 17 or sequences at least 65% identical thereto; wherein the heavy chain variable region comprises a CDR1 set forth in SEQ ID No: 18 or sequences at least 65% identical thereto, a CDR2 set forth in SEQ ID No: 19 or sequences at least 65% identical thereto, a CDR3 set forth in SEQ ID No: 20 or sequences at least 65% identical thereto.

Embodiment 30. Antibody or binding fragment thereof comprising a light chain variable region and/or a heavy chain variable region, wherein the light chain variable region comprises a CDR1 set forth in SEQ ID No: 29 or sequences at least 65% identical thereto, a CDR2 set forth in SEQ ID No: 30 or sequences at least 65% identical thereto, a CDR3 set forth in SEQ ID No: 31 or sequences at least 65% identical thereto; wherein the heavy chain variable region comprises a CDR1 set forth in SEQ ID No: 32 or sequences at least 65% identical thereto, a CDR2 set forth in SEQ ID No: 33 or sequences at least 65% identical thereto, a CDR3 set forth in SEQ ID No: 34 or sequences at least 65% identical thereto.

Embodiment 31. Antibody or binding fragment thereof, comprising a light chain variable region and/or a heavy chain variable region, wherein the light chain variable region comprises a CDR1 set forth in SEQ ID No: 43 or sequences at least 65% identical thereto, a CDR2 set forth in SEQ ID No: 44 or sequences at least 65% identical thereto, a CDR3 set forth in SEQ ID No: 45 or sequences at least 65% identical thereto; and/or wherein the heavy chain variable region comprises a CDR1 set forth in SEQ ID No: 46 or sequences at least 65% identical thereto, a CDR2 set forth in SEQ ID No: 47 or sequences at least 65% identical thereto, a CDR3 set forth in SEQ ID No: 48 or sequences at least 65% identical thereto.

Embodiment 32. Antibody or binding fragment thereof, comprising a light chain variable region and/or a heavy chain variable region, wherein the light chain variable region comprises a CDR1 set forth in SEQ ID No: 57 or sequences at least 65% identical thereto, a CDR2 set forth in SEQ ID No: 58 or sequences at least 65% identical thereto, a CDR3 set forth in SEQ ID No: 59 or sequences at least 65% identical thereto; and/or wherein the heavy chain variable region comprises a CDR1 set forth in SEQ ID No: 60 or sequences at least 65% identical thereto, a CDR2 set forth in SEQ ID No: 61 or sequences at least 65% identical thereto, a CDR3 set forth in SEQ ID No: 62 or sequences at least 65% identical thereto.

Embodiment 33. Antibody or binding fragment thereof, comprising a light chain variable region and/or a heavy chain variable region, wherein the light chain variable region comprises a CDR1 set forth in SEQ ID No: 71 or sequences at least 65% identical thereto, a CDR2 set forth in SEQ ID No: 72 or sequences at least 65% identical thereto, a CDR3 set forth in SEQ ID No: 73 or sequences at least 65% identical thereto; and/or wherein the heavy chain variable region comprises a CDR1 set forth in SEQ ID No: 74 or sequences at least 65% identical thereto, a CDR2 set forth in SEQ ID No: 75 or sequences at least 65% identical thereto, a CDR3 set forth in SEQ ID No: 76 or sequences at least 65% identical thereto.

Embodiment 34. Antibody or binding fragment thereof comprising a light chain variable region and/or a heavy chain variable region, wherein the light chain variable region comprises a CDR1 set forth in SEQ ID No: 1 or sequences at least 91% identical thereto, a CDR2 set forth in SEQ ID No: 2 or sequences at least 71% identical thereto, a CDR3 set forth in SEQ ID No: 3; wherein the heavy chain variable region comprises a CDR1 set forth in SEQ ID No: 4 or sequences at least 80% identical thereto, a CDR2 set forth in SEQ ID No: 5 or sequences at least 82% identical thereto, a CDR3 set forth in SEQ ID No: 6 or a sequence at least 94% identical thereto.

Embodiment 35. Antibody or binding fragment thereof comprising a light chain variable region and/or a heavy chain variable region, wherein the light chain variable region comprises a CDR1 set forth in SEQ ID No: 71 or sequences at least 91% identical thereto, a CDR2 set forth in SEQ ID No: 72 or sequences at least 71% identical thereto, a CDR3 set forth in SEQ ID No: 73; wherein the heavy chain variable region comprises a CDR1 set forth in SEQ ID No: 74 or sequences at least 80% identical thereto, a CDR2 set forth in SEQ ID No: 75 or sequences at least 82% identical thereto, a CDR3 set forth in SEQ ID No: 76 or sequences at least 94% identical thereto.

Embodiment 36. An antibody or binding fragment thereof which competes with an antibody according to any one of embodiments 1 to 35 for specific binding to the allergen.

Embodiment 37. A polynucleotide encoding the antibody or binding fragment thereof according to any one of embodiments 1 to 36.

Embodiment 38. A vector comprising the polynucleotide of embodiment 37.

Embodiment 39. A cell comprising the polynucleotide of embodiment 37 or the vector of embodiment 38.

Embodiment 40. A method for preparing an anti-allergen antibody or allergen-binding fragment thereof, consisting of culturing the cell of embodiment 39 and isolating the antibody or allergen binding fragment thereof from the cell or culture medium of the cell.

Embodiment 41. Antibody composition comprising at least two antibodies, wherein at least one of the antibodies is selected from the antibodies as defined in embodiments 18 to 26 or 28 to 35.

Embodiment 42. Antibody composition according to embodiment 41, wherein at least two of the antibodies are selected from the antibodies as defined in embodiments 18 to 26 or 28 to 35.

Embodiment 43. Antibody composition according to embodiment 42, wherein at least three of the antibodies are selected from the antibodies as defined in embodiments 18 to 26 or 28 to 35.

Embodiment 44. A pharmaceutical composition comprising at least one of the compounds selected from the group consisting of antibody or binding fragment of any one of embodiments 1 to 36, or the antibody composition according to embodiments 41 to 43, the polynucleotide of embodiment 37, the vector of embodiment 38 and the cell of embodiment 39.

Embodiment 45. A pharmaceutical composition according to embodiment 44, comprising the antibody or binding fragment of any one of embodiments 1 to 36 or the antibody composition according to embodiments 41 to 43.

Embodiment 46. A pharmaceutical composition according to embodiments 44 to 45, further comprising a pharmaceutical acceptable carrier.

Embodiment 47. A pharmaceutical composition according to embodiments 44 to 46, wherein the pharmaceutical composition further comprises at least one additional agent useful for treating peanut allergy.

Embodiment 48. A pharmaceutical composition according to embodiment 47 wherein the additional agent useful for treating peanut allergy is selected from the group β-adrenergic agonists, epinephrine, antihistamine, corticosteroid, anti-IgE antibody, anti-IgE antibody binding fragment, peptide vaccine and further antibodies capable of binding to a peanut allergen.

Embodiment 49. A pharmaceutical composition according to embodiments 44 to 48, wherein the composition is intended for subcutaneous, intravenous, intramuscular, intraperitoneally intranasal and/or inhalative administration.

Embodiment 50. Kit comprising (i) the pharmaceutical composition according to embodiments 44 to 46, (ii) at least one additional agent useful for treating peanut allergy selected from the group β-adrenergic agonist, antihistamine, corticosteroid, anti-IgE antibody, anti-IgE antibody binding fragment, peptide vaccine and further antibodies capable of binding to a peanut allergen.

Embodiment 51. Kit according to embodiment 50, wherein the at least one additional agent is a β-adrenergic agonist, preferably epinephrine.

Embodiment 52. Antibody or binding fragment thereof according to any one of embodiments 1 to 36, antibody composition according to embodiments 41 to 43, polynucleotide according to embodiment 37, vector according to embodiment 38, cell according to embodiment 39 or pharmaceutical composition according to embodiments 44 to 49 for use in the treatment of peanut allergy.

Embodiment 53. Antibody or binding fragment, antibody composition, polynucleotide, vector, cell or pharmaceutical composition for use in the treatment of peanut allergy according to embodiment 52, wherein the treatment is prophylactic or therapeutic.

Embodiment 54. A method of evaluating the capacity of a candidate antibody or binding fragment thereof to inhibit allergen binding/and/or allergen-induced activity in a human,
wherein the method comprises
(i) incubating the candidate antibody or binding fragment thereof with a composition comprising IgEs derived from the human and a food allergen;
(ii) evaluating whether the candidate antibody inhibits allergen binding to IgEs/ and/or allergen-induced activity in the composition comprising IgEs derived from the human.

Embodiment 55. The method of embodiment 54, further comprising the step of
(iii) determining whether the administration of the candidate antibody is a suitable treatment for a patient suffering from food allergy based on the result of step (ii).

Embodiment 56. Method according to embodiments 54 and 55, wherein the candidate antibody is an antibody as defined in embodiments 1 to 36.

Embodiment 57. Method according to embodiments 54 to 56, wherein in step (i) the composition comprising IgEs from the human comprises basophils.

Embodiment 58. Method according to embodiments 54 to 57, wherein the basophils are derived from an allergic patient.

Embodiment 59. Method according to embodiments 54 to 58, wherein the basophils are donor-derived IgE-stripped basophils.

Embodiment 60. Method according to embodiments 54 to 59, wherein the expression of CD63+at the surface of the basophil and/or the expression of CD203c is measured.

Embodiment 61. Method according to embodiments 54 to 60, wherein the basophils are identified based on the CCR3 expression.

Embodiment 62. Method according to embodiments 54 to 59, wherein the secretion of a mediator from basophils is measured.

Embodiment 63. Method according to embodiment 62, wherein the mediator is leukotriene.

Embodiment 64. Method according to embodiment 63, wherein the mediator is sulfidoleukotrine.

Embodiment 65. Method according to any one of embodiments 54 to 64, wherein the composition comprising IgEs derived from the human is plasma, sera, blood, saliva, peripheral blood mononuclear cell (PBMC), leukocytes, basophils or IgEs stripped from basophils.

Embodiment 66. Method according to any one of embodiments 54 to 65, wherein the human is suffering from food allergy.

Embodiment 67. Method according to any one of embodiments 54 to 66, wherein the human is suffering from peanut allergy.

Embodiment 68. Method according to any one of embodiments 54 to 67, wherein the food allergen is a peanut allergen.

Embodiment 69. Method according to embodiment 68, wherein the peanut allergen is selected from the group consisting of Ara h 1, Ara h 2, Ara h 3, Ara h 4, Ara h 5, Ara h 6/7, Ara h 8, Ara h 9 and Ara h 10/11.

Embodiment 70. Method according to embodiment 69, wherein the peanut allergen is selected from the group consisting of Ara h 1, Ara h 2, Ara h 3 and Ara h 6, or a combination thereof.

Embodiment 71. Method according to any one of embodiment 68 to 70, wherein the peanut allergen is recombinantly expressed, synthetically generated or is of peanut origin.

Embodiment 72. A method of detecting or quantifying whether an allergen is present in a sample comprising the following steps:
i) incubation of the sample with an antibody according to any one of embodiments 1 to 36 or with an antibody composition according to embodiments 41 to 43,
ii) detecting the antibody which is bound to allergen in the sample.

Embodiment 73. The method of embodiment 72, wherein the antibody is detectably labeled.

Embodiment 74. The method of embodiment 72, wherein the antibody is unlabeled and used in combination with a second antibody that is detectably labeled.

Embodiment 75. The method of embodiment 73 or 74, wherein the detectable label is selected from the group consisting of an enzyme, a radioisotope, a fluorophore, a peptide and a heavy metal.

The invention claimed is:

1. An antibody or binding fragment thereof capable of binding to a food allergen, wherein the antibody is selected from the group consisting of:
   a) the antibody or binding fragment thereof comprises a light chain variable region and a heavy chain variable region, wherein the light chain variable region comprises a CDR1 set forth in SEQ ID NO: 43, a CDR2 set forth in SEQ ID NO: 44, and a CDR3 set forth in SEQ ID NO: 45; and wherein the heavy chain variable region comprises a CDR1 set forth in SEQ ID NO: 46, a CDR2 set forth in SEQ ID NO: 47, and a CDR3 set forth in SEQ ID NO: 48; and
   b) the antibody or binding fragment thereof comprises a light chain variable region and a heavy chain variable region, wherein the light chain variable region comprises a CDR1 set forth in SEQ ID NO: 29, a CDR2 set forth in SEQ ID NO: 30, and a CDR3 set forth in SEQ ID NO: 31; and wherein the heavy chain variable region comprises a CDR1 set forth in SEQ ID NO: 32, a CDR2 set forth in SEQ ID NO: 33, a CDR3 set forth in SEQ ID NO: 34; and
   wherein the food allergen is a peanut allergen.

2. The antibody or binding fragment thereof according to claim 1, wherein the antibody is human-derived.

3. The antibody or binding fragment thereof according to claim 1, wherein the antibody is a monoclonal antibody and/or a recombinant antibody.

4. The antibody or binding fragment thereof according to claim 1, wherein the antibody is an IgG or IgA antibody.

5. The antibody or binding fragment thereof according to claim 2, wherein the human is selected from the group consisting of a human suffering from a peanut allergy, a peanut-sensitized human without a clinically-relevant allergy, a human suffering from a peanut allergy that underwent immunotherapy, a human that has outgrown a peanut allergy and a human of unknown clinical history for peanut allergy.

6. The antibody or binding fragment thereof according to claim 1, wherein the antibody is capable of reducing, inhibiting or neutralizing allergen-mediated biological activity.

7. The antibody or binding fragment thereof according to claim 1, wherein the antibody is capable of reducing or inhibiting the binding of an IgE antibody to the food allergen.

8. A composition comprising at least two antibodies or binding fragments thereof, wherein at least one of the antibodies or binding fragments thereof is selected from the antibodies in claim 1.

9. A pharmaceutical composition comprising the antibody or binding fragment of claim 1.

10. The pharmaceutical composition according to claim 9, further comprising a pharmaceutically acceptable carrier.

11. A kit comprising (i) the pharmaceutical composition according to claim 9, (ii) at least one additional agent useful for treating peanut allergy selected from the group consisting of β-adrenergic agonist, antihistamine, corticosteroid, anti-IgE antibody, anti-IgE antibody binding fragment, peptide vaccine and a further antibody capable of binding to a peanut allergen.

12. A kit according to claim 11, wherein the β-adrenergic agonist is epinephrine.

13. A method of treating a peanut allergy comprising administering an antibody or binding fragment thereof according to claim 1.

* * * * *

SEQUENCE LISTING

```
<160> NUMBER OF SEQ ID NOS: 100

<210> SEQ ID NO 1
<211> LENGTH: 11
<212> TYPE: PRT
<213> ORGANISM: Homo sapiens

<400> SEQUENCE: 1

Arg Ala Ser Gln Thr Ile Asp Asn Trp Leu Ala
1               5                   10

<210> SEQ ID NO 2
<211> LENGTH: 7
<212> TYPE: PRT
```

```
<213> ORGANISM: Homo sapiens

<400> SEQUENCE: 2

Gln Ala Ser Ser Leu Gln Ser
1               5

<210> SEQ ID NO 3
<211> LENGTH: 9
<212> TYPE: PRT
<213> ORGANISM: Homo sapiens

<400> SEQUENCE: 3

Gln Lys Ser Asn Gly Tyr Ser Arg Thr
1               5

<210> SEQ ID NO 4
<211> LENGTH: 5
<212> TYPE: PRT
<213> ORGANISM: Homo sapiens

<400> SEQUENCE: 4

Asp Phe Gly Met Ala
1               5

<210> SEQ ID NO 5
<211> LENGTH: 17
<212> TYPE: PRT
<213> ORGANISM: Homo sapiens

<400> SEQUENCE: 5

Gly Ile Asn Trp Ser Gly His Ser Thr Gly Phe Val Asp Ser Met Lys
1               5                   10                  15

Gly

<210> SEQ ID NO 6
<211> LENGTH: 18
<212> TYPE: PRT
<213> ORGANISM: Homo sapiens

<400> SEQUENCE: 6

Val Gly Arg Leu Cys Ser Gly Asp Ile Cys Asp Ser Met Gly Ala Phe
1               5                   10                  15

Asp Leu

<210> SEQ ID NO 7
<211> LENGTH: 107
<212> TYPE: PRT
<213> ORGANISM: Homo sapiens

<400> SEQUENCE: 7

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Thr Ile Asp Asn Trp
                20                  25                  30

Leu Ala Trp Tyr Gln Gln Arg Pro Gly Lys Ala Pro Lys Leu Leu Ile
            35                  40                  45

Tyr Gln Ala Ser Ser Leu Gln Ser Gly Val Ser Ser Arg Phe Arg Gly
        50                  55                  60

Ser Gly Ser Gly Thr Glu Phe Thr Leu Thr Ile Thr Ser Leu Gln Pro
65                  70                  75                  80

Asp Asp Phe Ala Thr Tyr Tyr Cys Gln Lys Ser Asn Gly Tyr Ser Arg
```

```
                        85                   90                   95
Thr Phe Gly Gln Gly Thr Lys Val Glu Ile Lys
                100                 105

<210> SEQ ID NO 8
<211> LENGTH: 127
<212> TYPE: PRT
<213> ORGANISM: Homo sapiens

<400> SEQUENCE: 8

Glu Glu Gln Leu Val Glu Ser Gly Gly Arg Leu Leu Arg Pro Gly Glu
1               5                   10                  15

Ser Leu Ser Leu Ser Cys Ala Ala Val Gly Phe Asn Phe Gly Asp Phe
            20                  25                  30

Gly Met Ala Trp Val Arg Gln Pro Pro Gly Lys Gly Leu Glu Trp Val
        35                  40                  45

Ala Gly Ile Asn Trp Ser Gly His Ser Thr Gly Phe Val Asp Ser Met
    50                  55                  60

Lys Gly Arg Leu Thr Ile Ser Arg Asp Ser Ala Lys Ser Ser Leu Phe
65                  70                  75                  80

Leu Gln Met Asn Ser Leu Arg Gly Glu Asp Thr Ala Val Tyr Tyr Cys
                85                  90                  95

Ala Arg Val Gly Arg Leu Cys Ser Gly Asp Ile Cys Asp Ser Met Gly
            100                 105                 110

Ala Phe Asp Leu Trp Gly Gln Gly Thr Met Val Thr Val Ser Ser
        115                 120                 125

<210> SEQ ID NO 9
<211> LENGTH: 107
<212> TYPE: PRT
<213> ORGANISM: Homo sapiens

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 330
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 321
<212> TYPE: DNA
<213> ORGANISM: Homo sapiens

<400> SEQUENCE: 11
gacatccaga tgacccagtc tccttccacc ctgtctgcat ctataggaga cagagtcacc    60
atcacttgtc gggccagtca gaccattgac aactggttgg cctggtatca acagagacca   120
gggaaagccc ctaaactcct gatctatcag gcgtctagtc tacaaagtgg ggtctcatca   180
aggttcagag gcagtggatc tggcacagaa ttcactctca ccatcaccag cctgcagcct   240
gatgactttg ctacttatta ttgtcagaag tctaatggct attctcgtac tttcggccag   300
gggaccaagg tggagatcaa a                                             321

```
<210> SEQ ID NO 12
<211> LENGTH: 381
<212> TYPE: DNA
<213> ORGANISM: Homo sapiens

<400> SEQUENCE: 12
gaggaacagc tggtggagtc tgggggacgt ttattacggc ctggggagtc cctgagcctc      60
tcctgtgcag ccgttggatt caacttcggt gattttggca tggcctgggt ccgccaacct    120
ccagggaagg ggctggagtg ggtcgctggc atcaattgga gtggccatag tacaggtttt    180
gtagactcca tgaagggtcg actcaccatc tccagagaca cgccaagag ttccctgttt     240 ctgcaaatga acagtctgcg aggcgaggac acggccgtgt attactgtgc gagagtcggg    300
agactttgta gtggagatat ttgcgactca atgggtgctt ttgatctgtg gggccagggg    360
acaatggtca ccgtctcttc a                                              381

<210> SEQ ID NO 13
<211> LENGTH: 324
<212> TYPE: DNA
<213> ORGANISM: Homo sapiens

<400> SEQUENCE: 13
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                           324

<210> SEQ ID NO 14
<211> LENGTH: 993
<212> TYPE: DNA
<213> ORGANISM: Homo sapiens

<400> SEQUENCE: 14
gcctccacca agggcccatc ggtcttcccc ctggcaccct cctccaagag cacctctggg      60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctggggga     360 ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggatgag    720
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
```

-continued

```
cagcagggga acgtcttctc atgctccgtg atgcatgagg ctctgcacaa ccactacacg    960
cagaagagcc tctccctgtc tccgggtaaa tga                                 993
```

<210> SEQ ID NO 15
<211> LENGTH: 17
<212> TYPE: PRT
<213> ORGANISM: Homo sapiens

<400> SEQUENCE: 15

```
Lys Ser Ser Gln Ser Ile Leu Asp Asn Ser Asn Asn Lys Asn Phe Ile
1               5                   10                  15

Ala
```

<210> SEQ ID NO 16
<211> LENGTH: 7
<212> TYPE: PRT
<213> ORGANISM: Homo sapiens

<400> SEQUENCE: 16

```
Trp Ala Ser Ala Arg Glu Ser
1               5
```

<210> SEQ ID NO 17
<211> LENGTH: 9
<212> TYPE: PRT
<213> ORGANISM: Homo sapiens

<400> SEQUENCE: 17

```
Tyr Gln Tyr Tyr Ser Thr Pro His Thr
1               5
```

<210> SEQ ID NO 18
<211> LENGTH: 5
<212> TYPE: PRT
<213> ORGANISM: Homo sapiens

<400> SEQUENCE: 18

```
Asn Phe Asp Ile Asn
1               5
```

<210> SEQ ID NO 19
<211> LENGTH: 17
<212> TYPE: PRT
<213> ORGANISM: Homo sapiens

<400> SEQUENCE: 19

```
Trp Met Ser Pro Lys Ser Gly Asp Thr Gly Tyr Ala Gln Lys Phe Gln
1               5                   10                  15

Gly
```

<210> SEQ ID NO 20
<211> LENGTH: 6
<212> TYPE: PRT
<213> ORGANISM: Homo sapiens

<400> SEQUENCE: 20

```
Gly Val Asp Gly Thr Asn
1               5
```

<210> SEQ ID NO 21
<211> LENGTH: 113
<212> TYPE: PRT
<213> ORGANISM: Homo sapiens

<400> SEQUENCE: 21

Asp Ile Val Met Thr Gln Ser Pro Asp Ser Leu Gly Val Ser Leu Gly
1               5                   10                  15

Glu Arg Ala Thr Ile Ser Cys Lys Ser Ser Gln Ser Ile Leu Asp Asn
            20                  25                  30

Ser Asn Asn Lys Asn Phe Ile Ala Trp Phe Gln Gln Lys Pro Gly Gln
        35                  40                  45

Pro Pro Lys Leu Leu Ile Tyr Trp Ala Ser Ala Arg Glu Ser Gly Val
    50                  55                  60

Pro Asp Arg Phe Ser Gly Ser Gly Ser Gly Thr Glu Phe Thr Leu Thr
65                  70                  75                  80

Ile Asn Ser Leu Gln Ala Glu Asp Val Ala Val Tyr Tyr Cys Tyr Gln
                85                  90                  95

Tyr Tyr Ser Thr Pro His Thr Phe Gly Gln Gly Thr Lys Leu Asp Leu
            100                 105                 110

Arg

<210> SEQ ID NO 22
<211> LENGTH: 115
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Ile Phe Arg Asn Phe
            20                  25                  30

Asp Ile Asn Trp Val Arg Gln Ala Thr Gly Gln Gly Leu Glu Trp Met
        35                  40                  45

Gly Trp Met Ser Pro Lys Ser Gly Asp Thr Gly Tyr Ala Gln Lys Phe
    50                  55                  60

Gln Gly Arg Val Thr Met Thr Arg Asp Thr Ser Ile Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Val Asp Gly Thr Asn Trp Gly Gln Gly Thr Arg Val Thr
            100                 105                 110

Val Ser Ser
        115

<210> SEQ ID NO 23
<211> LENGTH: 107
<212> TYPE: PRT
<213> ORGANISM: Homo sapiens

<400> SEQUENCE: 23

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu

```
                65                  70                  75                  80
            Lys His Lys Val Tyr Ala Cys Glu Val Thr His Gln Gly Leu Ser Ser
                            85                  90                  95

Pro Val Thr Lys Ser Phe Asn Arg Gly Glu Cys
                        100                 105
```

<210> SEQ ID NO 24
<211> LENGTH: 326
<212> TYPE: PRT
<213> ORGANISM: Homo sapiens

<400> SEQUENCE: 24

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Ala
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 25
<211> LENGTH: 339
<212> TYPE: DNA
<213> ORGANISM: Homo sapiens

<400> SEQUENCE: 25

```
gacatcgtga tgacccagtc tccagactcc ctgggtgtgt ctctgggcga gagggccacc      60
atcagctgca agtccagcca gagtatttta gataactcca acaataagaa cttcatagct     120
tggttccagc agaaaccagg acagcccct aagctgctca tttactgggc atctgcccgg     180
gaatccgggg tccctgaccg attcagtggc agcgggtctg ggacagaatt cactctcacc     240
atcaacagcc tgcaggctga agatgtggca gtttattact gttaccaata ctattctact     300
cctcacactt ttggccaggg gaccaagctg gatctcaga                            339
```

<210> SEQ ID NO 26
<211> LENGTH: 345
<212> TYPE: DNA
<213> ORGANISM: Homo sapiens

<400> SEQUENCE: 26

```
caggtgcagc tggtgcagtc tggggctgag gtgaagaagc ctggggcctc agtgaaggtc      60
tcctgcaggg cttctggata catcttccgc aactttgata tcaactgggt gcgacaggcc     120
actggacaag gcttgagtg gatgggatgg atgagcccta agagtggtga caccggctat     180
gctcagaagt ccagggcag ggtcaccatg accagggaca cctccataaa cacagcctac     240
atggaactga gcagcctgac atctgaggat tcggccgtct attactgtgc gagaggtgtc     300
gacgggacca actggggcca gggaacccgg gtcaccgtct cctca                     345
```

<210> SEQ ID NO 27
<211> LENGTH: 324
<212> TYPE: DNA
<213> ORGANISM: Homo sapiens

<400> SEQUENCE: 27

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                            324
```

<210> SEQ ID NO 28
<211> LENGTH: 981
<212> TYPE: DNA
<213> ORGANISM: Homo sapiens

<400> SEQUENCE: 28

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgctctgac cagcggcgtg cacaccttcc cggctgtcct acagtcctca     180
ggactctact ccctcagcag cgtggtgacc gtgacctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
```

-continued

```
ctcttccccc caaaacccaa ggacaccctc atgatctccc ggaccctga ggtcacgtgc      420 gtggtggtgg acgtgagcca cgaagacccc gaggtccagt tcaactggta cgtggacggc      480
gtggaggtgc ataatgcaaa gacaaagcca cgggaggagc agttcaacag cacgttccgt      540
gtggtcagcg tcctcaccgt tgtgcaccag gactggctga acggcaagga gtacaagtgc      600
aaggtctcca caaaggcct cccagccccc atcgagaaaa ccatctccaa aaccaaaggg      660
cagccccgag aaccacaggt gtacaccctg cccccatccc gggaggagat gaccaagaac      720
caggtcagcc tgacctgcct ggtcaaaggc ttctaccca gcgacatcgc cgtggagtgg      780
gagagcaatg ggcagccgga gaacaactac aaggccacac ctcccatgct ggactccgac      840
ggctccttct tcctctacag caagctcacc gtggacaaga gcaggtggca gcaggggaac      900
gtcttctcat gctccgtgat gcatgaggct ctgcacaacc actacacgca gaagagcctc      960
tccctgtctc cgggtaaatg a                                                981
```

<210> SEQ ID NO 29
<211> LENGTH: 12
<212> TYPE: PRT
<213> ORGANISM: Homo sapiens

<400> SEQUENCE: 29

Arg Ala Ser Gln Ser Val Ser Asn Met Phe Leu Val
1               5                   10

<210> SEQ ID NO 30
<211> LENGTH: 7
<212> TYPE: PRT
<213> ORGANISM: Homo sapiens

<400> SEQUENCE: 30

Gly Ala Ser Thr Arg Ala Thr
1               5

<210> SEQ ID NO 31
<211> LENGTH: 9
<212> TYPE: PRT
<213> ORGANISM: Homo sapiens

<400> SEQUENCE: 31

Gln Gln Asn Gly Asn Ser Pro Tyr Thr
1               5

<210> SEQ ID NO 32
<211> LENGTH: 5
<212> TYPE: PRT
<213> ORGANISM: Homo sapiens

<400> SEQUENCE: 32

Asp Tyr Asn Met Asn
1               5

<210> SEQ ID NO 33
<211> LENGTH: 17
<212> TYPE: PRT
<213> ORGANISM: Homo sapiens

<400> SEQUENCE: 33

Ser Ile Thr Arg Ser Ser Arg Thr Ile Tyr Tyr Ala Asp Ser Val Lys
1               5                   10                  15

Gly

<210> SEQ ID NO 34
<211> LENGTH: 14
<212> TYPE: PRT
<213> ORGANISM: Homo sapiens

<400> SEQUENCE: 34

Glu Asp Phe Asp Val Ser Thr Gly Pro Tyr Tyr Met Asp Val
1               5                   10

<210> SEQ ID NO 35
<211> LENGTH: 108
<212> TYPE: PRT
<213> ORGANISM: Homo sapiens

<400> SEQUENCE: 35

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Met
            20                  25                  30

Phe Leu Val Trp Tyr Gln Gln Lys Pro Gly Gln Ala Pro Arg Leu Leu
        35                  40                  45

Met Tyr Gly Ala Ser Thr Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asn Gly Asn Ser Pro
                85                  90                  95

Tyr Thr Phe Gly Gln Gly Thr Lys Leu Glu Ile Lys
            100                 105

<210> SEQ ID NO 36
<211> LENGTH: 123
<212> TYPE: PRT
<213> ORGANISM: Homo sapiens

<400> SEQUENCE: 36

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Asn Met Asn Trp Val Arg Gln Ala Pro Gly Lys Gly Leu Glu Trp Val
        35                  40                  45

Ser Ser Ile Thr Arg Ser Ser Arg Thr Ile Tyr Tyr Ala Asp Ser Val
    50                  55                  60

Lys Gly Arg Phe Thr Ile Ser Arg Asp Asn Ala Lys Asn Ser Leu His
65                  70                  75                  80

Leu Gln Met Asn Ser Leu Arg Asp Ala Asp Thr Ala Val Tyr Tyr Cys
                85                  90                  95

Ala Arg Glu Asp Phe Asp Val Ser Thr Gly Pro Tyr Tyr Met Asp Val
            100                 105                 110

Trp Gly Asn Gly Thr Thr Val Ile Val Ser Ser
        115                 120

<210> SEQ ID NO 37
<211> LENGTH: 107
<212> TYPE: PRT
<213> ORGANISM: Homo sapiens

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 38
<211> LENGTH: 330
<212> TYPE: PRT
<213> ORGANISM: Homo sapiens

<400> SEQUENCE: 38

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 39
<211> LENGTH: 324
<212> TYPE: DNA
<213> ORGANISM: Homo sapiens

<400> SEQUENCE: 39
gaaattgtgt tgacgcagtc tccaggcacc ctgtctttgt ctccagggga aagagccacc      60
ctctcctgca gggccagtca gagtgttagc aacatgttct tagtctggta tcagcagaaa     120
cctggccagg ctcccaggct cctcatgtat ggtgcatcta ccagggccac tgacatccca     180
gacaggttca gtggcagtgg gtctgggaca gacttcactc tcaccatcag cagactggag     240
cctgaagatt ttgcagtgta ttactgtcag cagaatggta actcaccata cacttttggc     300
caggggacca agctggagat caaa                                             324

<210> SEQ ID NO 40
<211> LENGTH: 384
<212> TYPE: DNA
<213> ORGANISM: Homo sapiens

<400> SEQUENCE: 40
gaagatgtcc agtgtgaggt gcagctggtg gagtctgggg gaggcttggt caagccgggg      60
gggtcgctga gactctcctg tgcagcgtct ggattcatct tcagcgatta taacatgaat     120
tgggtccgcc aggctccagg aaggggctg agtgggttt catccattac tagaagtagt     180
aggaccattt actacgcaga ctctgtgaag ggccgattca ccatatccag agacaatgcc     240
aagaactcac tgcatctgca aatgaacagt ctcagagacg cggacacggc tgtgtattat     300
tgtgcgagag aggatttcga tgtttcgact ggcccctact acatggacgt ctggggcaac     360
gggaccacgg tcatcgtctc ctca                                             384

<210> SEQ ID NO 41
<211> LENGTH: 324
<212> TYPE: DNA
<213> ORGANISM: Homo sapiens

<400> SEQUENCE: 41
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg ttag                                             324

<210> SEQ ID NO 42
```

<211> LENGTH: 993
<212> TYPE: DNA
<213> ORGANISM: Homo sapiens

<400> SEQUENCE: 42

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc cccgggtaaa tga                                993
```

<210> SEQ ID NO 43
<211> LENGTH: 16
<212> TYPE: PRT
<213> ORGANISM: Homo sapiens

<400> SEQUENCE: 43

```
Arg Ser Ser Gln Ser Leu Val His Arg Asn Gly Tyr Asn Tyr Leu Asp
1               5                   10                  15
```

<210> SEQ ID NO 44
<211> LENGTH: 7
<212> TYPE: PRT
<213> ORGANISM: Homo sapiens

<400> SEQUENCE: 44

```
Met Ala Ser Lys Arg Ala Ser
1               5
```

<210> SEQ ID NO 45
<211> LENGTH: 8
<212> TYPE: PRT
<213> ORGANISM: Homo sapiens

<400> SEQUENCE: 45

```
Met Gln Ala Leu Gln Thr Trp Thr
1               5
```

<210> SEQ ID NO 46
<211> LENGTH: 5
<212> TYPE: PRT
<213> ORGANISM: Homo sapiens

<400> SEQUENCE: 46

Asp Tyr Thr Met His
1               5

<210> SEQ ID NO 47
<211> LENGTH: 17
<212> TYPE: PRT
<213> ORGANISM: Homo sapiens

<400> SEQUENCE: 47

Ala Ile Ser Tyr Gly Gly Thr Asn Lys Tyr Tyr Ala Asp Ser Val Lys
1               5                   10                  15

Gly

<210> SEQ ID NO 48
<211> LENGTH: 9
<212> TYPE: PRT
<213> ORGANISM: Homo sapiens

<400> SEQUENCE: 48

Asp Ser Gly Tyr Arg Ser Leu Leu His
1               5

<210> SEQ ID NO 49
<211> LENGTH: 111
<212> TYPE: PRT
<213> ORGANISM: Homo sapiens

<400> SEQUENCE: 49

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Val His Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Met Ala Ser Lys Arg Ala Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Trp Thr Phe Gly Gln Gly Thr Lys Val Glu Val Asn
            100                 105                 110

<210> SEQ ID NO 50
<211> LENGTH: 118
<212> TYPE: PRT
<213> ORGANISM: Homo sapiens

<400> SEQUENCE: 50

Gln Val Gln Leu Val Glu Ser Gly Gly Val Val Gln Pro Gly Arg
1               5                   10                  15

Ser Leu Arg Leu Ser Cys Ala Ala Ser Gly Ile Ala Phe Asn Asp Tyr
            20                  25                  30

Thr Met His Trp Val Arg Arg Ser Pro Asp Lys Gly Leu Glu Trp Val
        35                  40                  45

Ala Ala Ile Ser Tyr Gly Gly Thr Asn Lys Tyr Tyr Ala Asp Ser Val
    50                  55                  60

Lys Gly Arg Phe Thr Ile Ser Arg Asp Ser Ser Lys Asn Thr Leu Phe

```
                65                  70                  75                  80
Leu Gln Met Asp Ser Leu Arg Val Glu Asp Thr Ala Val Tyr Tyr Cys
                    85                  90                  95

Ala Arg Asp Ser Gly Tyr Arg Ser Leu Leu His Trp Gly Gln Gly Thr
                    100                 105                 110

Leu Val Thr Val Ser Ser
            115

<210> SEQ ID NO 51
<211> LENGTH: 107
<212> TYPE: PRT
<213> ORGANISM: Homo sapiens

<400> SEQUENCE: 51

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 52
<211> LENGTH: 327
<212> TYPE: PRT
<213> ORGANISM: Homo sapiens

<400> SEQUENCE: 52

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                   165                 170                 175
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325
```

<210> SEQ ID NO 53
<211> LENGTH: 333
<212> TYPE: DNA
<213> ORGANISM: Homo sapiens

<400> SEQUENCE: 53

```
gagattgtgt tgactcagtc tccactctcc ctgcccgtca cccctggtga gccggcctcc    60
atctcctgca ggtcgagtca gagcctcgtg catagaaatg gatacaacta tttagattgg   120
tacctgcaga agccagggca gtctccacag ctcctgatct atatggcttc taaacgggcc   180
tccggggtcc ctgacaggtt cagtggcagt gggtcaggca cagaatttac actgaaaatc   240
agcagagtgg aggctgagga tgttggaatt tattactgca tgcaagctct acaaacttgg   300
acgttcggcc aagggaccaa ggtggaagtc aac                               333
```

<210> SEQ ID NO 54
<211> LENGTH: 354
<212> TYPE: DNA
<213> ORGANISM: Homo sapiens

<400> SEQUENCE: 54

```
caggtgcagc tggtggagtc tgggggaggc gtggtgcagc ctgggaggtc cctgagactc    60
tcatgtgcag cctctggcat cgccttcaat gactacacta tgcactgggt ccgccggtct   120
ccagacaagg gcctggagtg ggtggcagct atatcatatg gtgggactaa taaatactac   180
gcagattccg tgaagggccg attcaccatc tccagagaca gttccaagaa caccctgttt   240
ctgcagatgg acagcctgag agttgaggac acggctgtgt attactgtgc gagagattct   300
ggttatcgga gtcttttgca ctggggccag ggaaccctgg tcaccgtctc ctca         354
```

<210> SEQ ID NO 55
<211> LENGTH: 324
<212> TYPE: DNA
<213> ORGANISM: Homo sapiens

<400> SEQUENCE: 55

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                          324
```

<210> SEQ ID NO 56
<211> LENGTH: 984
<212> TYPE: DNA
<213> ORGANISM: Homo sapiens

<400> SEQUENCE: 56

```
gcttccacca agggcccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc ccccatgccc atcatgccca gcacctgagt tcctgggggg accatcagtc   360
ttcctgttcc ccccaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggag   780
tgggagagca atgggcagcc ggagaacaac tacaagacca cgcctcccgt gctggactcc   840
gacggctcct tcttcctcta cagcaggcta accgtggaca agagcaggtg gcaggagggg   900
aatgtcttct catgctccgt gatgcatgag gctctgcaca accactacac acagaagagc   960
ctctccctgt ctctgggtaa atga                                          984
```

<210> SEQ ID NO 57
<211> LENGTH: 11
<212> TYPE: PRT
<213> ORGANISM: Homo sapiens

<400> SEQUENCE: 57

Gln Ala Asn Gln Asp Ile Val Asn Ser Leu Asn
1               5                   10

<210> SEQ ID NO 58
<211> LENGTH: 7
<212> TYPE: PRT
<213> ORGANISM: Homo sapiens

<400> SEQUENCE: 58

Asp Ala Ser Lys Leu Glu Thr
1               5

<210> SEQ ID NO 59

<211> LENGTH: 9
<212> TYPE: PRT
<213> ORGANISM: Homo sapiens

<400> SEQUENCE: 59

Gln Gln Tyr Glu Asn Leu Pro His Thr
1               5

<210> SEQ ID NO 60
<211> LENGTH: 7
<212> TYPE: PRT
<213> ORGANISM: Homo sapiens

<400> SEQUENCE: 60

Ile Gly Gly Tyr Tyr Trp Ser
1               5

<210> SEQ ID NO 61
<211> LENGTH: 16
<212> TYPE: PRT
<213> ORGANISM: Homo sapiens

<400> SEQUENCE: 61

Tyr Ile Tyr Ser Asn Gly Arg Thr Tyr Tyr Asn Pro Ser Leu Lys Ser
1               5                   10                  15

<210> SEQ ID NO 62
<211> LENGTH: 7
<212> TYPE: PRT
<213> ORGANISM: Homo sapiens

<400> SEQUENCE: 62

Glu Ala Trp Glu Thr Pro Leu
1               5

<210> SEQ ID NO 63
<211> LENGTH: 107
<212> TYPE: PRT
<213> ORGANISM: Homo sapiens

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Gln Ala Asn Gln Asp Ile Val Asn Ser
                20                  25                  30

Leu Asn Trp Phe Gln His Lys Pro Gly Thr Ala Pro Lys Val Leu Ile
            35                  40                  45

Tyr Asp Ala Ser Lys Leu Glu Thr Gly Val Pro Ser Arg Phe Ser Gly
        50                  55                  60

Ser Gly Ser Gly Thr His Phe Thr Phe Thr Ile Ser Gly Leu Gln Pro
65                  70                  75                  80

Glu Asp Phe Ala Thr Tyr Phe Cys Gln Gln Tyr Glu Asn Leu Pro His
                85                  90                  95

Thr Phe Gly Gln Gly Thr Lys Leu Glu Ile Arg
            100                 105

<210> SEQ ID NO 64
<211> LENGTH: 117
<212> TYPE: PRT
<213> ORGANISM: Homo sapiens

<400> SEQUENCE: 64

Gln Val Gln Leu Gln Glu Ala Gly Pro Arg Leu Val Lys Pro Ser Gln
1               5                   10                  15

Thr Leu Ser Val Thr Cys Thr Val Ser Gly Ala Ser Ile Thr Ile Gly
            20                  25                  30

Gly Tyr Tyr Trp Ser Trp Ile Arg Gln His Pro Gly Lys Gly Leu Glu
        35                  40                  45

Trp Met Gly Tyr Ile Tyr Ser Asn Gly Arg Thr Tyr Tyr Asn Pro Ser
    50                  55                  60

Leu Lys Ser Arg Ile Ala Met Ser Ile Asp Thr Ser Lys Asn Gln Phe
65                  70                  75                  80

Ser Leu Lys Leu Thr Ser Val Thr Ala Ala Asp Thr Ala Ile Tyr Phe
                85                  90                  95

Cys Ala Arg Glu Ala Trp Glu Thr Pro Leu Trp Gly Gln Gly Thr Leu
            100                 105                 110

Ile Thr Val Ser Ser
            115

<210> SEQ ID NO 65
<211> LENGTH: 107
<212> TYPE: PRT
<213> ORGANISM: Homo sapiens

<400> SEQUENCE: 65

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 66
<211> LENGTH: 330
<212> TYPE: PRT
<213> ORGANISM: Homo sapiens

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Gly Leu His Asn His Tyr Thr
305                 310                 315                 320
Gln Lys Ser Leu Ser Leu Ser Pro Gly Lys
                325                 330

<210> SEQ ID NO 67
<211> LENGTH: 321
<212> TYPE: DNA
<213> ORGANISM: Homo sapiens

<400> SEQUENCE: 67
gacatccaga tgactcagtc tccatcctcc ctgtctgctt ctgtaggaga cagagtcacc      60
atcacttgcc aggcgaatca ggacattgtc aactctttaa attggtttca acacaaacca     120
gggacagccc ctaaagtcct gatctacgat gcatccaaat tggaaacagg ggtcccatct     180
aggttcagtg gaagtgggtc tgggacacat tttactttca ccataagtgg cctgcagcct     240
gaagattttg caacatattt ctgtcaacaa tatgagaatc ttccgcacac ttttggccag     300
gggaccaagt tggagatcag a                                                321

<210> SEQ ID NO 68
<211> LENGTH: 351
<212> TYPE: DNA
<213> ORGANISM: Homo sapiens

<400> SEQUENCE: 68
caggtgcagc tgcaggaggc gggcccacga ctggtgaagc cttcacagac cctgtcagtc      60
acctgcactg tctctggtgc ctccatcacc attggcggtt actactggag ttggatccgc     120
cagcacccag ggaagggcct ggaatggatg ggtacatct attccaatgg gaggacctac     180
```

```
tacaatccgt ccctcaagag tcgaattgcc atgtcaatag acacgtctaa aaaccagttc      240
tccctgaagc tgacttctgt gacagccgcg gacacggcca tatatttctg tgcgcgggag      300
gcgtgggaga cgccactgtg gggccaggga accctgatca ccgtctcctc c               351

<210> SEQ ID NO 69
<211> LENGTH: 324
<212> TYPE: DNA
<213> ORGANISM: Homo sapiens

<400> SEQUENCE: 69
cgaactgtgg ctgcaccatc tgtcttcatc ttcccgccat ctgatgagca gttgaaatct       60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg ttag                                            324

<210> SEQ ID NO 70
<211> LENGTH: 993
<212> TYPE: DNA
<213> ORGANISM: Homo sapiens

<400> SEQUENCE: 70
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag gcagccccg agaaccacag gtgtacaccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg gtctgcacaa ccactacacg      960
cagaagagcc tctccctgtc tccgggtaaa tga                                  993

<210> SEQ ID NO 71
<211> LENGTH: 11
<212> TYPE: PRT
<213> ORGANISM: Homo sapiens

<400> SEQUENCE: 71

Arg Ala Ser Gln Asn Ile Asp Asn Trp Leu Ala
1               5                   10
```

<210> SEQ ID NO 72
<211> LENGTH: 7
<212> TYPE: PRT
<213> ORGANISM: Homo sapiens

<400> SEQUENCE: 72

Lys Ala Ser Ser Leu Gly Ser
1               5

<210> SEQ ID NO 73
<211> LENGTH: 9
<212> TYPE: PRT
<213> ORGANISM: Homo sapiens

<400> SEQUENCE: 73

Gln Lys Ser Asn Gly Tyr Ser Arg Thr
1               5

<210> SEQ ID NO 74
<211> LENGTH: 5
<212> TYPE: PRT
<213> ORGANISM: Homo sapiens

<400> SEQUENCE: 74

Asp Phe Gly Met Ser
1               5

<210> SEQ ID NO 75
<211> LENGTH: 17
<212> TYPE: PRT
<213> ORGANISM: Homo sapiens

<400> SEQUENCE: 75

Gly Ile Asp Trp Ser Gly Arg Ser Thr Gly Tyr Val Asp Ser Met Lys
1               5                   10                  15

Gly

<210> SEQ ID NO 76
<211> LENGTH: 18
<212> TYPE: PRT
<213> ORGANISM: Homo sapiens

<400> SEQUENCE: 76

Val Gly Arg Leu Cys Ser Gly Asp Ser Cys Asp Ser Met Gly Ala Phe
1               5                   10                  15

Asp Leu

<210> SEQ ID NO 77
<211> LENGTH: 107
<212> TYPE: PRT
<213> ORGANISM: Homo sapiens

<400> SEQUENCE: 77

Asp Ile Gln Leu Thr Gln Ser Pro Ser Thr Leu Ser Ala Ser Ile Gly
1               5                   10                  15

Asp Ser Val Thr Ile Thr Cys Arg Ala Ser Gln Asn Ile Asp Asn Trp
            20                  25                  30

Leu Ala Trp Tyr Gln Gln Lys Pro Gly Lys Ala Pro Arg Leu Leu Ile
        35                  40                  45

Tyr Lys Ala Ser Ser Leu Gly Ser Gly Val Ser Ser Lys Phe Arg Gly
    50                  55                  60

```
Ser Gly Phe Gly Thr Glu Phe Thr Leu Thr Ile Thr Ser Leu Gln Pro
 65                  70                  75                  80

Asp Asp Phe Ala Thr Tyr Tyr Cys Gln Lys Ser Asn Gly Tyr Ser Arg
                 85                  90                  95

Thr Phe Gly Gln Gly Thr Lys Val Asp Ile Lys
            100                 105

<210> SEQ ID NO 78
<211> LENGTH: 127
<212> TYPE: PRT
<213> ORGANISM: Homo sapiens

<400> SEQUENCE: 78

Glu Val Gln Leu Leu Glu Ser Gly Arg Leu Leu Arg Pro Gly Gly
 1               5                   10                  15

Ser Leu Ser Leu Ser Cys Val Ala Ser Gly Phe Tyr Phe Gly Asp Phe
                 20                  25                  30

Gly Met Ser Trp Val Arg Gln Val Pro Gly Lys Gly Leu Glu Trp Val
             35                  40                  45

Ser Gly Ile Asp Trp Ser Gly Arg Ser Thr Gly Tyr Val Asp Ser Met
         50                  55                  60

Lys Gly Arg Leu Thr Ile Ser Arg Asp Asn Asp Lys Ser Ser Leu Tyr
 65                  70                  75                  80

Leu Gln Met Asn Asp Leu Arg Gly Glu Asp Thr Ala Val Tyr Tyr Cys
                 85                  90                  95

Ala Arg Val Gly Arg Leu Cys Ser Gly Asp Ser Cys Asp Ser Met Gly
                100                 105                 110

Ala Phe Asp Leu Trp Gly Gln Gly Thr Met Val Thr Val Ser Ser
            115                 120                 125

<210> SEQ ID NO 79
<211> LENGTH: 321
<212> TYPE: DNA
<213> ORGANISM: Homo sapiens

<400> SEQUENCE: 79
gacatccagt tgacccagtc tccttccacc ctgtctgcat ctataggaga cagcgtcacc     60
atcacttgcc gggccagtca gaatattgat aactggttgg cctggtatca acagaaacca    120
gggaaagccc ctagactcct gatctacaag gcgtctagtc taggaagtgg ggtctcatca    180
aagttcagag gcagtggatt tgggacagag ttcactctca ccatcaccag cctgcagcct    240
gatgactttg caacctatta ttgtcagaag tctaatggct attctcgtac ttttggccag    300
gggaccaaag tggatatcaa a                                              321

<210> SEQ ID NO 80
<211> LENGTH: 381
<212> TYPE: DNA
<213> ORGANISM: Homo sapiens

<400> SEQUENCE: 80
gaggtgcagc tgttggagtc tgggggacgt ttattacggc cggggggggtc cctgagcctc     60 tcctgtgtag cctctggatt ctacttcggt gattttggca tgagctgggt ccgccaggtt    120
ccagggaagg ggctggagtg ggtctctggc attgactgga gtggccgtag tacaggttat    180
gtagactcca tgaagggccg actcaccatc tccagagaca cgacaagag ttccctgtat     240 ttgcaaatga acgatctgcg cggcgaggac acggccgtct attactgtgc gagggtcggg    300
```

```
agactctgta gtggtgattc ttgcgactca atgggcgctt tgacctgtgt gggccagggg    360
acaatggtca ccgtctcttc a                                              381
```

<210> SEQ ID NO 81
<211> LENGTH: 20
<212> TYPE: PRT
<213> ORGANISM: Arachis hypogaea

<400> SEQUENCE: 81

Ala Met Ala Leu Lys Leu Thr Ile Leu Val Ala Leu Ala Leu Phe Leu
1               5                   10                  15

Leu Ala Ala His
            20

<210> SEQ ID NO 82
<211> LENGTH: 20
<212> TYPE: PRT
<213> ORGANISM: Arachis hypogaea

<400> SEQUENCE: 82

Ala Leu Ala Leu Phe Leu Leu Ala Ala His Ala Ser Ala Arg Gln Gln
1               5                   10                  15

Trp Glu Leu Gln
            20

<210> SEQ ID NO 83
<211> LENGTH: 20
<212> TYPE: PRT
<213> ORGANISM: Arachis hypogaea

<400> SEQUENCE: 83

Ala His Ala Ser Ala Arg Gln Gln Trp Glu Leu Gln Gly Asp Arg Arg
1               5                   10                  15

Cys Gln Ser Gln
            20

<210> SEQ ID NO 84
<211> LENGTH: 20
<212> TYPE: PRT
<213> ORGANISM: Arachis hypogaea

<400> SEQUENCE: 84

Trp Glu Leu Gln Gly Asp Arg Arg Cys Gln Ser Gln Leu Glu Arg Ala
1               5                   10                  15

Asn Leu Arg Pro
            20

<210> SEQ ID NO 85
<211> LENGTH: 20
<212> TYPE: PRT
<213> ORGANISM: Arachis hypogaea

<400> SEQUENCE: 85

Cys Gln Ser Gln Leu Glu Arg Ala Asn Leu Arg Pro Cys Glu Gln His
1               5                   10                  15

Leu Met Gln Lys
            20

<210> SEQ ID NO 86
<211> LENGTH: 20
<212> TYPE: PRT
<213> ORGANISM: Arachis hypogaea

```
<400> SEQUENCE: 86

Asn Leu Arg Pro Cys Glu Gln His Leu Met Gln Lys Ile Gln Arg Asp
1               5                   10                  15

Glu Asp Ser Tyr
            20

<210> SEQ ID NO 87
<211> LENGTH: 20
<212> TYPE: PRT
<213> ORGANISM: Arachis hypogaea

<400> SEQUENCE: 87

Leu Met Gln Lys Ile Gln Arg Asp Glu Asp Ser Tyr Gly Arg Asp Pro
1               5                   10                  15

Tyr Ser Pro Ser
            20

<210> SEQ ID NO 88
<211> LENGTH: 20
<212> TYPE: PRT
<213> ORGANISM: Arachis hypogaea

<400> SEQUENCE: 88

Glu Asp Ser Tyr Gly Arg Asp Pro Tyr Ser Pro Ser Gln Asp Pro Tyr
1               5                   10                  15

Ser Pro Ser Gln
            20

<210> SEQ ID NO 89
<211> LENGTH: 20
<212> TYPE: PRT
<213> ORGANISM: Arachis hypogaea

<400> SEQUENCE: 89

Tyr Ser Pro Ser Gln Asp Pro Tyr Ser Pro Ser Gln Asp Pro Asp Arg
1               5                   10                  15

Arg Asp Pro Tyr
            20

<210> SEQ ID NO 90
<211> LENGTH: 20
<212> TYPE: PRT
<213> ORGANISM: Arachis hypogaea

<400> SEQUENCE: 90

Ser Pro Ser Gln Asp Pro Asp Arg Arg Asp Pro Tyr Ser Pro Ser Pro
1               5                   10                  15

Tyr Asp Arg Arg
            20

<210> SEQ ID NO 91
<211> LENGTH: 20
<212> TYPE: PRT
<213> ORGANISM: Arachis hypogaea

<400> SEQUENCE: 91

Arg Asp Pro Tyr Ser Pro Ser Pro Tyr Asp Arg Arg Gly Ala Gly Ser
1               5                   10                  15

Ser Gln His Gln
            20
```

```
<210> SEQ ID NO 92
<211> LENGTH: 20
<212> TYPE: PRT
<213> ORGANISM: Arachis hypogaea

<400> SEQUENCE: 92

Tyr Asp Arg Arg Gly Ala Gly Ser Ser Gln His Gln Glu Arg Cys Cys
1               5                   10                  15

Asn Glu Leu Asn
            20

<210> SEQ ID NO 93
<211> LENGTH: 20
<212> TYPE: PRT
<213> ORGANISM: Arachis hypogaea

<400> SEQUENCE: 93

Ser Gln His Gln Glu Arg Cys Cys Asn Glu Leu Asn Glu Phe Glu Asn
1               5                   10                  15

Asn Gln Arg Cys
            20

<210> SEQ ID NO 94
<211> LENGTH: 20
<212> TYPE: PRT
<213> ORGANISM: Arachis hypogaea

<400> SEQUENCE: 94

Asn Glu Leu Asn Glu Phe Glu Asn Asn Gln Arg Cys Met Cys Glu Ala
1               5                   10                  15

Leu Gln Gln Ile
            20

<210> SEQ ID NO 95
<211> LENGTH: 20
<212> TYPE: PRT
<213> ORGANISM: Arachis hypogaea

<400> SEQUENCE: 95

Asn Gln Arg Cys Met Cys Glu Ala Leu Gln Gln Ile Met Glu Asn Gln
1               5                   10                  15

Ser Asp Arg Leu
            20

<210> SEQ ID NO 96
<211> LENGTH: 20
<212> TYPE: PRT
<213> ORGANISM: Arachis hypogaea

<400> SEQUENCE: 96

Leu Gln Gln Ile Met Glu Asn Gln Ser Asp Arg Leu Gln Gly Arg Gln
1               5                   10                  15

Gln Glu Gln Gln
            20

<210> SEQ ID NO 97
<211> LENGTH: 20
<212> TYPE: PRT
<213> ORGANISM: Arachis hypogaea

<400> SEQUENCE: 97

Ser Asp Arg Leu Gln Gly Arg Gln Gln Glu Gln Gln Phe Lys Arg Glu
```

```
-continued
                 1               5              10              15

Leu Arg Asn Leu
                20

<210> SEQ ID NO 98
<211> LENGTH: 22
<212> TYPE: PRT
<213> ORGANISM: Arachis hypogaea

<400> SEQUENCE: 98

Arg Gln Gln Glu Gln Gln Phe Lys Arg Glu Leu Arg Asn Leu Pro Gln
1               5                   10                  15

Gln Cys Gly Leu Arg Ala
                20

<210> SEQ ID NO 99
<211> LENGTH: 20
<212> TYPE: PRT
<213> ORGANISM: Arachis hypogaea

<400> SEQUENCE: 99

Leu Arg Asn Leu Pro Gln Gln Cys Gly Leu Arg Ala Pro Gln Arg Cys
1               5                   10                  15

Asp Leu Glu Val
                20

<210> SEQ ID NO 100
<211> LENGTH: 20
<212> TYPE: PRT
<213> ORGANISM: Arachis hypogaea

<400> SEQUENCE: 100

Gly Leu Arg Ala Pro Gln Arg Cys Asp Leu Glu Val Glu Ser Gly Gly
1               5                   10                  15

Arg Asp Arg Tyr
                20
```